(12) United States Patent
Yamamoto et al.

(10) Patent No.: US 9,656,969 B2
(45) Date of Patent: May 23, 2017

(54) POLYMER FILM, RETARDATION FILM, POLARIZING PLATE, LIQUID CRYSTAL DISPLAY, AND COMPOUND

(71) Applicant: FUJIFILM Corporation, Tokyo (JP)

(72) Inventors: Aiko Yamamoto, Kanagawa (JP); Satoshi Tanaka, Kanagawa (JP); Teruki Niori, Kanagawa (JP); Masato Nagura, Kanagawa (JP); Masaki Noro, Kanagawa (JP); Aiko Yoshida, Kanagawa (JP); Nobutaka Fukagawa, Kanagawa (JP); Yasukazu Kuwayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/045,789

(22) Filed: Feb. 17, 2016

(65) Prior Publication Data

US 2016/0159750 A1 Jun. 9, 2016

Related U.S. Application Data

(60) Division of application No. 14/470,249, filed on Aug. 27, 2014, now Pat. No. 9,296,877, which is a division
(Continued)

(30) Foreign Application Priority Data

Dec. 1, 2010 (JP) .................................. 2010-268491
Mar. 25, 2011 (JP) .................................. 2011-066949
(Continued)

(51) Int. Cl.
*C07D 413/00* (2006.01)
*C07D 239/48* (2006.01)
(Continued)

(52) U.S. Cl.
CPC ......... *C07D 239/48* (2013.01); *C07D 213/73* (2013.01); *C07D 213/75* (2013.01);
(Continued)

(58) Field of Classification Search
CPC .. C07D 239/42; C07D 239/48; C07D 239/50; C07D 239/52; C07D 239/69;
(Continued)

(56) References Cited

U.S. PATENT DOCUMENTS 6,630,973 B1 10/2003 Matsuoka et al.
8,158,220 B2 4/2012 Nagura et al.
(Continued)

FOREIGN PATENT DOCUMENTS

CN 102666704 A 9/2012
JP 2001-166144 A 6/2001
(Continued)

OTHER PUBLICATIONS

Notification of Reasons for Refusal issued by the Japanese Patent Office (JPO) on Apr. 26, 2016 in connection with Japanese Patent Application No. 2015-094239.
(Continued)

*Primary Examiner* — Ruiyun Zhang
(74) *Attorney, Agent, or Firm* — Edwards Neils LLC; Jean C. Edwards, Esq.

(57) ABSTRACT

Provided is a polymer film containing at least one of a compound represented by formula (1) of hydrates, solvates, or salts thereof. Y is a methine group or nitrogen atom. $Q^a$, $Q^b$, and $Q^c$ are a single bond or a divalent linking group. $R^a$, $R^b$, and $R^c$, are hydrogen atom, alkyl group, alkenyl group, alkynyl group, aryl group, cyano group, halogen group, or heterocyclic group. $X^2$ is a single bond or a divalent linking group. $X^1$ is a single bond or a predetermined divalent
(Continued)

linking group. $R^1$ and $R^2$ are a hydrogen atom, alkyl group, alkenyl group, alkynyl group, aryl group, or heterocyclic group

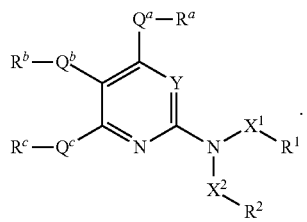

Formula (1)

7 Claims, 1 Drawing Sheet

Related U.S. Application Data of application No. 13/907,357, filed on May 31, 2013, now Pat. No. 8,871,314, which is a continuation of application No. PCT/JP2011/077796, filed on Dec. 1, 2011.

(30) Foreign Application Priority Data

| Mar. 25, 2011 | (JP) | 2011-066950 |
| Nov. 25, 2011 | (JP) | 2011-257364 |
| Nov. 25, 2011 | (JP) | 2011-257365 |

(51) Int. Cl.

| C08K 5/3462 | (2006.01) |
| G02B 1/04 | (2006.01) |
| C07D 213/73 | (2006.01) |
| C07D 213/75 | (2006.01) |
| C07D 239/47 | (2006.01) |
| C07D 239/50 | (2006.01) |
| C07D 239/95 | (2006.01) |
| C07D 401/12 | (2006.01) |
| C07D 403/04 | (2006.01) |
| C08K 5/3432 | (2006.01) |
| C07D 239/42 | (2006.01) |
| C07D 239/52 | (2006.01) |
| C07D 239/69 | (2006.01) |
| C07D 401/14 | (2006.01) |
| G02B 5/30 | (2006.01) |

(52) U.S. Cl.
CPC ......... *C07D 239/42* (2013.01); *C07D 239/47* (2013.01); *C07D 239/50* (2013.01); *C07D 239/52* (2013.01); *C07D 239/69* (2013.01); *C07D 239/95* (2013.01); *C07D 401/12* (2013.01); *C07D 401/14* (2013.01); *C07D 403/04* (2013.01); *C08K 5/3432* (2013.01); *C08K 5/3462* (2013.01); *G02B 1/04* (2013.01); *G02B 5/305* (2013.01); *G02B 5/3083* (2013.01); *G02B 5/30* (2013.01); *Y10T 428/10* (2015.01); *Y10T 428/1036* (2015.01); *Y10T 428/1041* (2015.01)

(58) Field of Classification Search
CPC .. C07D 239/95; C07D 401/12; C07D 401/14; C07D 403/04; C08K 5/3462
USPC ........ 544/122, 253, 296, 321, 323, 325, 332
See application file for complete search history.

(56) References Cited

U.S. PATENT DOCUMENTS

| 8,871,314 | B2 | 10/2014 | Yamamoto et al. |
| 8,906,475 | B2 | 12/2014 | Fukagawa et al. |
| 9,151,883 | B2 | 10/2015 | Fukagawa et al. |
| 9,296,877 | B2 | 3/2016 | Yamamoto et al. |
| 2008/0027001 | A1 | 1/2008 | Wood et al. |
| 2008/0175139 | A1* | 7/2008 | DiPietro ............... B82Y 10/00 369/284 |
| 2011/0076423 | A1 | 3/2011 | Nagura et al. |
| 2012/0180697 | A1 | 7/2012 | Fukagawa et al. |
| 2012/0204757 | A1 | 8/2012 | Nagura et al. |
| 2013/0266744 | A1 | 10/2013 | Yamamoto et al. |
| 2014/0053755 | A1 | 2/2014 | Nagura et al. |
| 2014/0318413 | A1 | 10/2014 | Fukagawa et al. |
| 2014/0363588 | A1 | 12/2014 | Yamamoto et al. |

FOREIGN PATENT DOCUMENTS

| JP | 2001-249223 A | 9/2001 |
| JP | 2003-315551 A | 11/2003 |
| JP | 2003-344655 A | 12/2003 |
| JP | 2004-109410 A | 4/2004 |
| JP | 2007-217519 A | 8/2007 |
| JP | 2007-297606 A | 11/2007 |
| JP | 2009-116346 A | 5/2009 |
| JP | 2010-015157 A | 1/2010 |
| JP | 2011-094114 A | 5/2011 |
| JP | 2012-082235 A | 4/2012 |
| JP | 2012-214682 A | 11/2012 |
| JP | 2012-214683 A | 11/2012 |
| JP | 5427738 B2 | 2/2014 |
| JP | 5543309 B2 | 7/2014 |
| WO | 2008/006103 A2 | 1/2008 |
| WO | 2011/040468 A1 | 4/2011 |

OTHER PUBLICATIONS

Notification of Reasons for Refusal issued by the Japanese Patent Office (JPO) on Apr. 26, 2016 in connection with Japanese Patent Application No. 2015-094240.
International Search Report issued in International Patent Application No. PCT/JP2011/077796 on Feb. 14, 2012.
Written Opinion issued in International Patent Application No. PCT/JP2011/077796 on Feb. 14, 2012.
International Preliminary Report on Patentability issued in International Patent Application No. PCT/JP2011/077796 on Jun. 4, 2013.
Non-Final Office Action issued in U.S. Appl. No. 14/470,249 on Mar. 18, 2015.
Final Office Action issued in U.S. Appl. No. 14/470,249 on Jul. 16, 2015.
Notice of Allowance issued in U.S. Appl. No. 14/470,249 on Nov. 17, 2015.
Notification of 2nd Office Action issued by the State Intellectual Property Office (SIPO) on Oct. 27, 2015 in connection with Chinese Patent Application No. 201180057939.6.
Notification of Reasons for Refusal issued by the Japanese Patent Office on Oct. 25, 2016, in connection with corresponding Japanese Patent Application No. 2011-257364.
Notification of Reasons for Refusal issued by the Japanese Patent Office on Oct. 25, 2016, in connection with corresponding Japanese Patent Application No. 2011-257365.
Jia-Jun Jiao et al.; Preparation and Liquid Cyrstalline Phase of T-Shaped Hydrogen-Bonded Liquid Crystal Complexes; Journal of Functional Polymers, 2007; pp. 209-215; vol. 19-20, No. 2.
Geetanjali; Molecular recognition studies of selected isoalloxazines with 2,6-diamindopyridine derivatives; Journal of Chemical Research; Nov. 2005; pp. 719-723; Issue11; Science Reviews.
Dongzhong Chem et al.; Supramolecular Liquid Crystals with Hydrogen-Bonding Self-Assembled T-Shaped Mesogens; Chemistry Letters; 2001; pp. 1156-1157; No. 11; The Chemical Society of Japan.

(56) References Cited

OTHER PUBLICATIONS

Norio Tamura et al.; Synthesis of 2,6-Diamidopyridine Derivatives and their Functions as Flavin Receptors in Choloroform; Journal of the Chemical Society, Perkin Transactions 2; 1994; Issue 10; pp. 2229-2237; The Royal Society of Chemistry.

* cited by examiner

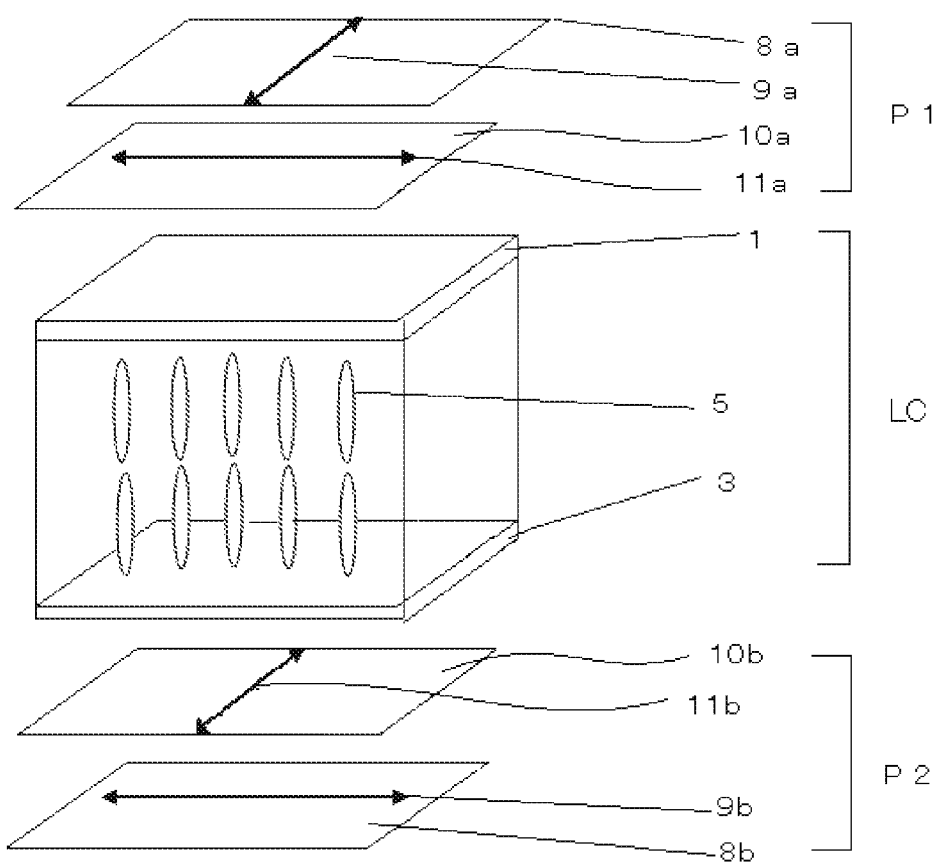

POLYMER FILM, RETARDATION FILM, POLARIZING PLATE, LIQUID CRYSTAL DISPLAY, AND COMPOUND

CROSS-REFERENCE TO RELATED APPLICATIONS

The present application is a divisional application of U.S. patent application Ser. No. 14/470,249, filed Aug. 27, 2014, which is a divisional application of U.S. patent application Ser. No. 13/907,357, filed May 31, 2013, which is a continuation of PCT/JP2011/077796 filed on Dec. 1, 2011, and claims priority under 35 U.S.C. §119 to Japanese Patent Application No. 2010/268491, filed on Dec. 1, 2010, Japanese Patent Application No. 2011/066949, filed on Mar. 25, 2011, Japanese Patent Application No. 2011/066950, filed on Mar. 25, 2011, Japanese Patent Application No. 2011/257364, filed on Nov. 25, 2011, and Japanese Patent Application No. 2011/257365, filed on Nov. 25, 2011, the content of all of which are herein incorporated by reference in their entirety.

TECHNICAL FIELD

The present invention relates to a polymer film that can be used in various purposes such as a retardation film and a polarizing plate protective film, and relates to a retardation film, a polarizing plate, and a liquid crystal display that include the polymer film. The invention also relates to a novel compound useful in various purposes such as an additive for the polymer film.

BACKGROUND ART

The display characteristics of a liquid crystal display have been progressively improved in recent years. The viewing angle characteristics of a liquid crystal display are known to be notably improved by a retardation film displaced between a polarizing plate and a liquid crystal cell. For compensation of the viewing angle, it is preferable to control the optical characteristics of the retardation film used, specifically, the in-plane retardation (Re) and/or thickness direction retardation (Rth) within appropriate ranges depending on the display mode.

A method disclosed for controlling the Re and Rth of a retardation film involves addition of a retardation enhancer to a polymer film (see Japanese Patent Laid-Open No. 2004-109410). The retardation enhancer disclosed in this document is a compound capable of forming a molecular complex having a keto-enol tautomeric structure as a constituent element, and a typical example thereof is a compound containing a 1,3,5-triazine ring such as a guanamine skeleton. Other retardation enhancers are also disclosed, such as disk-shaped compounds and compounds having other 1,3,5-triazine ring-containing structures (see Japanese Patent Laid-Open No. 2001-166144 and Japanese Patent Laid-Open No. 2003-344655).

[Patent Literature 1] Japanese Patent Laid-Open No. 2004-109410

[Patent Literature 2] Japanese Patent Laid-Open No. 2001-166144

[Patent Literature 3] Japanese Patent Laid-Open No. 2003-344655

SUMMARY OF INVENTION

Technical Problem

The present inventors, who have investigated such conventional polymer films containing retardation enhancers, have revealed that the Re and the Rth significantly vary depending on a change in humidity of the operating environment (which change may be referred to as humidity dependency of Re and Rth).

It is an object of the present invention to provide a polymer film having reduced variations in Re and Rth caused by a change in humidity of the operating environment and to provide a retardation film, a polarizing plate, and a liquid crystal display that include the polymer film.

It is another object of the present invention to provide a novel compound showing high solution stability and being useful in various purposes, such as an additive for polymer films.

Solution to Problem

The present inventors have intensively investigated various compounds for usefulness as additives to achieve an effect of enhancing Re and Rth. As a result, the inventors have found that a group of compounds each having a pyrimidine ring or a pyridine ring and having a prescribed substituent at a prescribed position on the ring enhances the retardation (Re and/or Rth) of a polymer film and have unexpectedly found that in a polymer film containing a compound belonging to the compound group and thereby having controlled Re and/or Rth, the fluctuations in Re and Rth caused by a change in humidity of the operating environment are notably reduced compared to those of polymer films having controlled Re and/or Rth by conventional retardation enhancers. The present invention was accomplished by further investigation based on these findings.

The retardation-enhancing function of a compound belonging to the compound group containing a pyrimidine ring or pyridine ring having a prescribed substituent at a prescribed position, i.e., the function of a compound used in the present invention, differs from the function of the retardation enhancer disclosed in Japanese Patent Laid-Open No. 2004-109410 in that the compound of the present invention does not need to form a molecular complex having a triazine ring, and differs from the function of the retardation enhancer disclosed in Japanese Patent Laid-Open No. 2001-166144 in that the compound of the present invention does not need to have a disk-like shape. The compound of the present invention also differs from the retardation enhancer disclosed in Patent Literature 3 in that the compound does not contain a 1,3,5-triazine ring.

[1] A polymer film comprising at least one kind of compounds represented by Formula (1), hydrates of the compounds, solvates of the compounds, and salts of the compounds:

[Chem. 1]

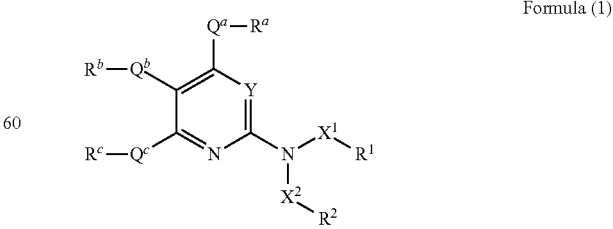

Formula (1)

wherein in Formula (1), Y represents —N— or —C(-$Q^d$-$R^d$)—; $Q^a$, $Q^b$, $Q^c$, and $Q^d$ each independently represent a single bond or a divalent linking group; $R^a$, $R^b$, $R^c$, and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring; $X^2$ represents a single bond or a divalent linking group; $X^1$ represents a single bond or a divalent group selected from a divalent linking group $G^1$:

[Chem. 2]

divalent linking group $G^1$

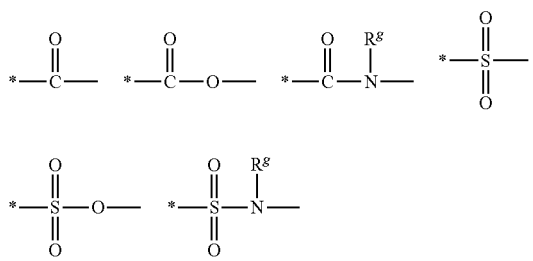

(in each formula, the side indicated by symbol * is a bonding site to the nitrogen atom introduced into the pyrimidine ring or pyridine ring in the compound represented by the each formula; and $R^g$ represents a hydrogen atom, an alkyl group, an alkenyl group, an alkynyl group, an aryl group, or a heterocyclic group); and $R^1$ and $R^2$ each independently represent a hydrogen atom, an alkyl group, an alkenyl group, an alkynyl group, an aryl group, or heterocyclic group, wherein $R^1$ and $R^2$ are optionally bonded to each other to forma ring, provided that compounds in which only one of -$Q^c$-$R^c$ and —N($X^1R^1$)$X^2R^2$ is —NH$_2$ and compounds in which Y is a nitrogen atom, both -$Q^c$-$R^c$ and —N($X^1R^1$)$X^2R^2$ are not —NH$_2$, and -$Q^a$-$R^a$ is —NH$_2$ are excluded.

[2] The polymer film according to [1], wherein the at least one kind of compounds represented by Formula (1) are added in the form of hydrates of the compounds, solvates of the compounds, or salts of the compounds.

[3] wherein Formula (1) is Formula (2):

[Chem. 3]

Formula (2)

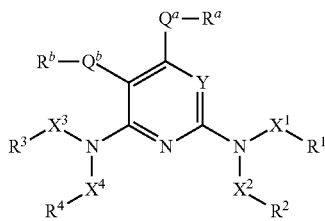

wherein symbols in Formula (2) are each synonymous with those in Formula (1); $X^4$ represents a single bond or a divalent linking group; $X^3$ represents a single bond or a divalent group selected from a divalent linking group $G^1$:

[Chem. 4]

divalent linking group $G^1$

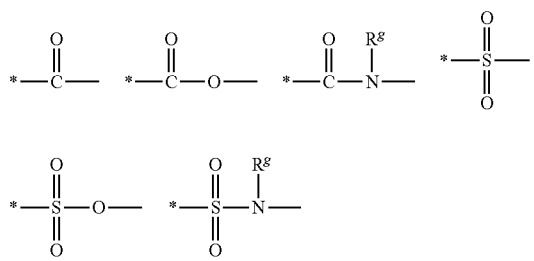

(in each formula, the side indicated by symbol * is a bonding site to the nitrogen atom introduced into the pyrimidine ring or pyridine ring in the compound represented by the formula; and $R^g$ represents a hydrogen atom, an alkyl group, an alkenyl group, an alkynyl group, an aryl group, or a heterocyclic group); and $R^3$ and $R^4$ each independently represent a hydrogen atom, an alkyl group, an alkenyl group, an alkynyl group, an aryl group, or a heterocyclic group, wherein $R^3$ and $R^4$ are optionally bonded to each other to form a ring.

[4] The polymer film according to [1] or [2], wherein Formula (1) is Formula (3) or (4):

[Chem. 5]

Formula (3)

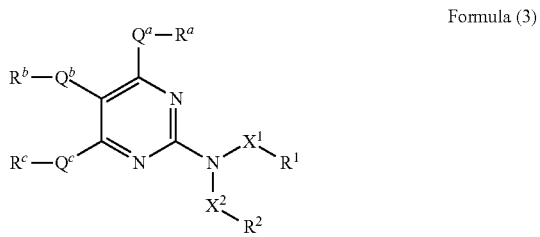

wherein symbols in Formula (3) are each synonymous with those in Formula (1);

[Chem. 6]

Formula (4)

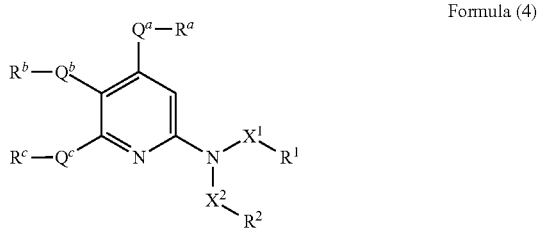

wherein symbols in Formula (4) are each synonymous with those in Formula (1).

[5] The polymer film according to [1] or [2], wherein Formula (1) is Formula (5-1):

[Chem. 7]

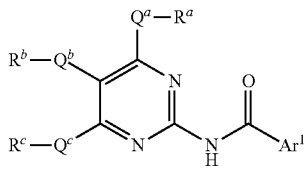

Formula (5-1)

wherein symbols in Formula (5-1) are each synonymous with those in Formula (1); and $Ar^1$ represents an aryl group.

[6] The polymer film according to [1] or [2], wherein Formula (1) is Formula (5-2):

[Chem. 8]

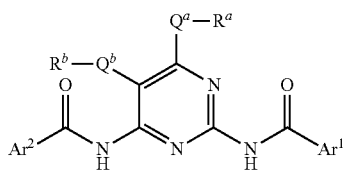

Formula (5-2)

wherein symbols in Formula (5-2) are each synonymous with those in Formulae (1) and (3); and $Ar^1$ and $Ar^2$ each independently represent an aryl group.

[7] The polymer film according to [1] or [2], wherein Formula (1) is Formula (6):

[Chem. 9]

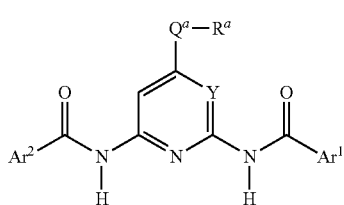

Formula (6)

wherein symbols in Formula (6) are each synonymous with those in Formula (1); and $Ar^1$ and $Ar^2$ each independently represent an aryl group.

[8] The polymer film according to any one of [1] to [7], wherein $Q^a$ represents a single bond or —O—, —S—, —NH—, or —N(R)— (wherein R is an alkyl group having 1 to 8 carbon atoms); and $R^a$ represents a hydrogen atom, a halogen atom, or an alkyl group having 1 to 8 carbon atoms.

[9] The polymer film according to [1] or [2], wherein Formula (1) is Formula (7-1):

[Chem. 10]

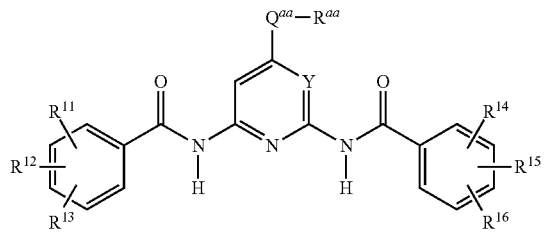

Formula (7-1)

wherein symbols in Formula (7-1) are each synonymous with those in Formula (1); $Q^{aa}$ represents a single bond or —O—, —S—, —NH—, or —N(R)— (wherein R is an alkyl group having 1 to 8 carbon atoms); $R^{aa}$ represents a hydrogen atom, a halogen atom, or an alkyl group having 1 to 8 carbon atoms; $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms.

[10] The polymer film according to [1] or [2], wherein Formula (1) is Formula (7-2):

[Chem. 11]

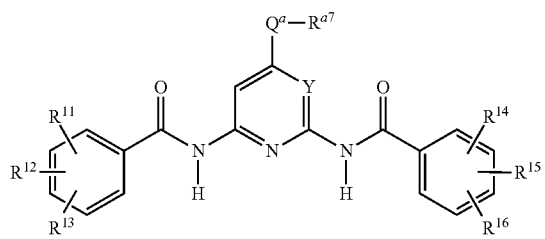

Formula (7-2)

wherein symbols in Formula (7-2) are each synonymous with those in Formula (1); $R^{a7}$ represents an alkyl group having 1 to 8 carbon atoms; and $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms.

[11] The polymer film according to [10], wherein Formula (7-2) is Formula (8), (9), or (10):

[Chem. 12]

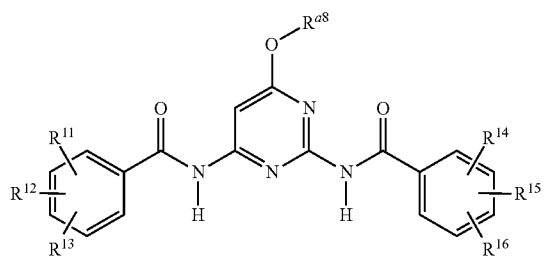

Formula (8)

-continued

Formula (9)

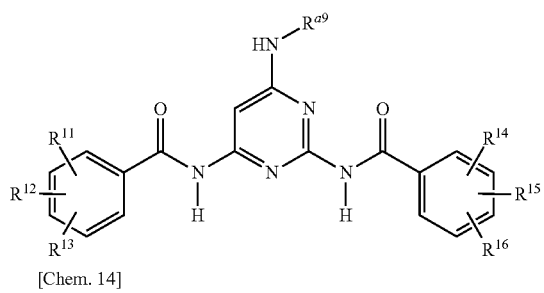

[Chem. 14]

Formula (10)

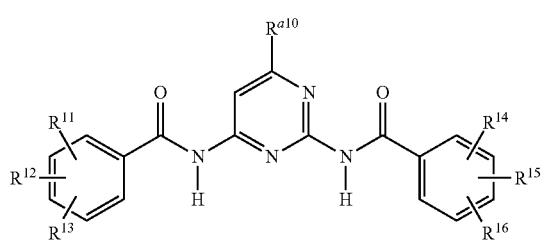

wherein symbols in each formula are each synonymous with those in Formula (7-2); and $R^{a8}$, $R^{a9}$, and $R^{a10}$ each independently represent an alkyl group having 1 to 8 carbon atoms.

[12] The polymer film according to [1] or [2], wherein Formula (1) is Formula (11a):

[Chem. 15]

Formula (11a)

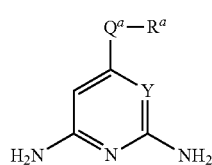

wherein symbols in Formula (11a) are each synonymous with those in Formula (1).

[13] The polymer film according to anyone of [1] to [12], further comprising at least one kind of compound represented by anyone of Formulae (IIIe), (IVe), and (Ve) or hydrate of any one of Formulae (IIIe), (IVe), and (Ve), solvate of Formulae (IIIe), (IVe), and (Ve), and salt of any one of Formulae (IIIe), (IVe), and (Ve):

[Chem. 16]

Formula (IIIe)

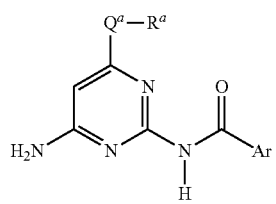

Formula (IVe)

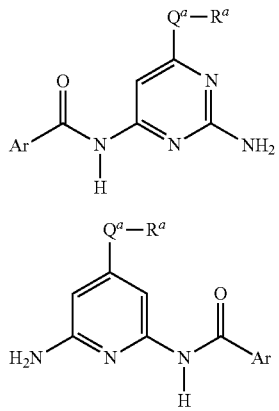

Formula (Ve)

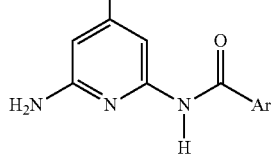

wherein symbols in each formula are each synonymous with those in Formula (1); and Ar's each independently represent an aryl group.

[14] A polymer film comprising at least one kind of compounds represented by Formula (I), hydrates of the compounds, solvates of the compounds, and salts of the compounds:

[Chem. 17]

Formula (I)

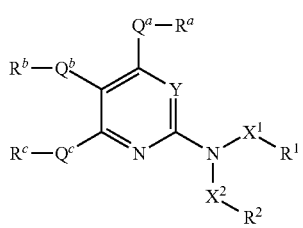

wherein in Formula (I), Y represents —N— or —C(-$Q^d$-$R^d$)—; $Q^a$, $Q^b$, $Q^c$, and $Q^d$ each independently represent a single bond or a divalent linking group; $R^a$, $R^b$, $R^c$, and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring; $X^2$ represents a single bond or a divalent linking group; $X^1$ represents a single bond or a divalent group selected from a divalent linking group $G^1$:

[Chem. 18]

divalent linking group $G^1$

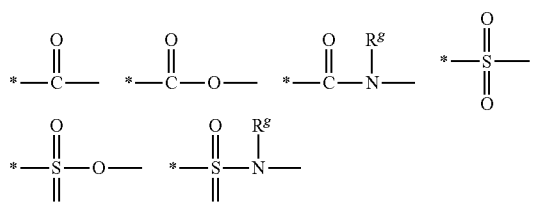

(in each formula, the side indicated by symbol * is a bonding site to the nitrogen atom introduced into the pyrimidine ring or pyridine ring in the compound represented by the formula; and $R^g$ represents a hydrogen atom, an alkyl group, an alkenyl group, an alkynyl group, an aryl group, or a heterocyclic group); and $R^1$ and $R^2$ each independently represent a hydrogen atom, an alkyl group, an alkenyl group, an alkynyl group, an aryl group, or a heterocyclic group, wherein $R^1$ and $R^2$ are optionally bonded to each other to form a ring, provided that one of -$Q^c$-$R^c$ and $N(X^1R^1)X^2R^2$ is —$NH_2$ and both are not simultaneously —$NH_2$ and that when Y is a nitrogen atom and when $N(X^1R^1)X^2R^2$ is —$NH_2$, -$Q^a$-$R^a$ is not —$NH_2$.

[15] The polymer film according to [14], wherein Formula (I) is Formula (II):

[Chem. 19]

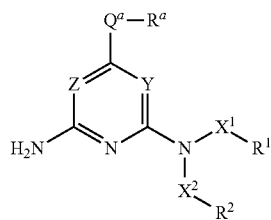

Formula (II)

wherein symbols in Formula (II) are each synonymous with those in Formula (I); Y represents —N— or —C(-$Q^d$-$R^d$)—, and Z represents —N— or —C(-$Q^b$-$R^b$)—, provided that Y and Z are not simultaneously —N—; $X^1$ represents a single bond or a linking group selected from the group consisting of divalent linking groups represented by a divalent linking group $G^2$; $X^2$ represents a single bond or a divalent linking group; $R^1$ and $R^2$ each independently represent a hydrogen atom, an alkyl group, an alkenyl group, an alkynyl group, an aryl group, or a heterocycle, and at least one of —$X^1$—$R^1$ and —$X^2$—$R^2$ is a substituent other than a hydrogen atom; $Q^a$, $Q^b$, and $Q^d$ each independently represent a single bond or —O—, —S—, or —NR'—, wherein R' represents a hydrogen atom, an alkyl group, an alkenyl group, an alkynyl group, an aryl group, or a heterocycle, and $Q^a$ and $R^a$, $Q^d$ and $R^d$, or $Q^b$ and $R^b$ are optionally bonded to each other to form a ring, or -$Q^a$-$R^a$—$R^d$-$Q^d$- or -$Q^a$-$R^a$—$R^b$-$Q^b$ optionally forms a ring; and $R^a$ represents a hydrogen atom, a halogen, an alkyl group, an alkenyl group, an alkynyl group, an aryl group, or a heterocycle, provided that when Z is —N—, -$Q^a$-$R^a$ represents a substituent other than an amino group and that $R^b$ and $R^d$ each independently represent a hydrogen atom, an alkyl group, an alkenyl group, an alkynyl group, an aryl group, or a heterocycle;

[Chem. 20]

divalent linking group $G^2$:

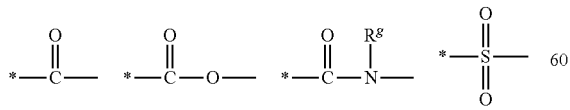

wherein symbols in the divalent linking group $G^2$ are each synonymous with those in the divalent linking group $G^1$.

[16] The polymer film according to [15], wherein Formula (II) is Formula (III), Formula (IV), or Formula (V):

[Chem. 21]

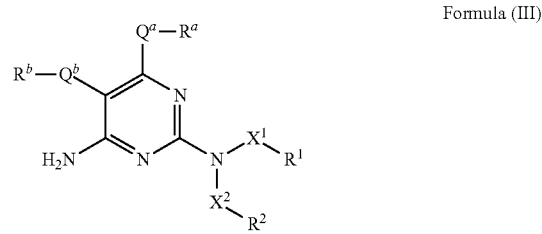

Formula (III)

wherein symbols in Formula (III) are each synonymous with those in Formula (II);

[Chem. 22]

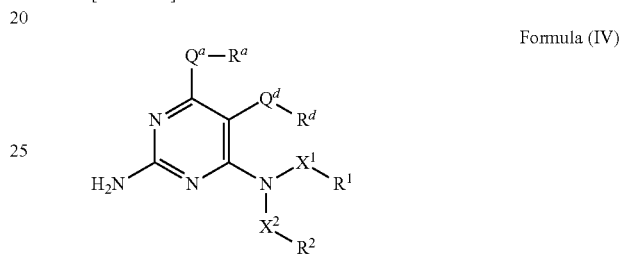

Formula (IV)

wherein symbols in Formula (IV) are each synonymous with those in Formula (II);

[Chem. 23]

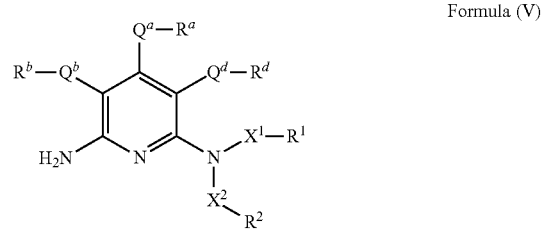

Formula (V)

wherein symbols in Formula (V) are each synonymous with those in Formula (II).

[17] The polymer film according to [15], wherein Formula (II) is Formula (IIIa), (IVa), or (Va):

[Chem. 24]

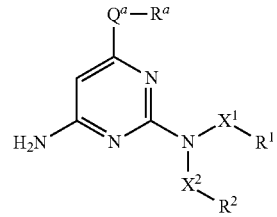

Formula (IIIa)

wherein symbols in Formula (IIIa) are each synonymous with those in Formula (II);

[Chem. 25]

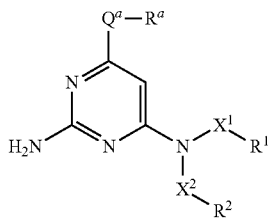

Formula (IVa)

wherein symbols in Formula (IVa) are each synonymous with those in Formula (II);

[Chem. 26]

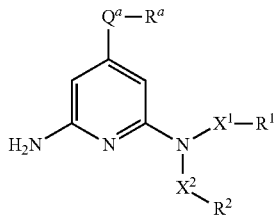

Formula (Va)

wherein symbols in Formula (Va) are each synonymous with those in Formula (II).

[18] The polymer film according to [15], wherein Formula (II) is Formula (IIIb), Formula (IVb), or Formula (Vb):

[Chem. 27]

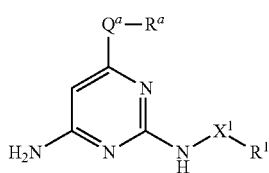

Formula (IIIb)

wherein symbols in Formula (IIIb) are each synonymous with those in Formula (II);

[Chem. 28]

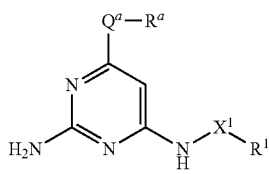

Formula (IVb)

wherein symbols in Formula (IVb) are each synonymous with those in Formula (II);

[Chem. 29]

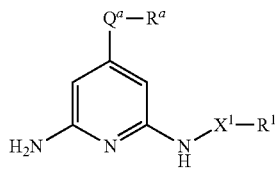

Formula (Vb)

wherein symbols in Formula (Vb) are each synonymous with those in Formula (II).

[19] The polymer film according to [15], wherein Formula (II) is Formula (IIIc), Formula (IVc), or Formula (Vc):

[Chem. 30]

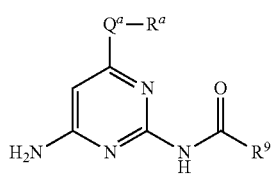

Formula (IIIc)

wherein symbols in Formula (IIIc) are each synonymous with those in Formula (II); and $R^9$ represents —O—Ar, an alkyl group, an alkenyl group, an alkynyl group, an aryl group, or a heterocyclic group, wherein Ar represents an aryl group;

[Chem. 31]

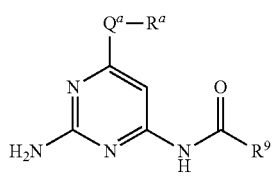

Formula (IVc)

wherein symbols in Formula (IVc) are each synonymous with those in Formula (II); and $R^9$ represents —O—Ar, an alkyl group, an alkenyl group, an alkynyl group, an aryl group, or a heterocyclic group, wherein Ar represents an aryl group;

[Chem. 32]

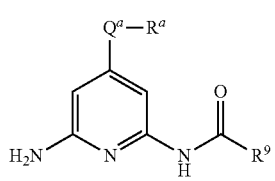

Formula (Vc)

wherein symbols in Formula (Vc) are each synonymous with those in Formula (II); and $R^9$ represents —O—Ar, an alkyl group, an alkenyl group, an alkynyl group, an aryl group, or a heterocyclic group, and Ar represents an aryl group.

[20] The polymer film according to [15], wherein Formula (II) is Formula (IIId), Formula (IVd), or Formula (Vd):

[Chem. 33]

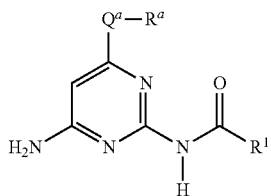

Formula (IIId)

wherein symbols in Formula (IIId) are each synonymous with those in Formula (II);

[Chem. 34]

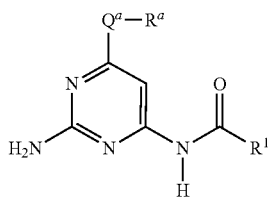

Formula (IVd)

wherein symbols in Formula (IVd) are each synonymous with those in Formula (II);

[Chem. 35]

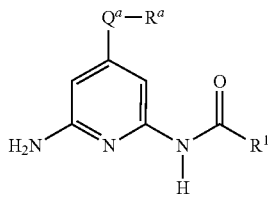

Formula (Vd)

wherein symbols in Formula (Vd) are each synonymous with those in Formula (II).

[21] The polymer film according to [15], wherein Formula (II) is Formula (IIIe), (IVe), or (Ve):

[Chem. 36]

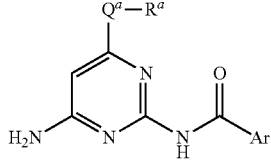

Formula (IIIe)

wherein symbols in Formula (IIIe) are each synonymous with those in Formula (II); and Ar represents an aryl group;

[Chem. 37]

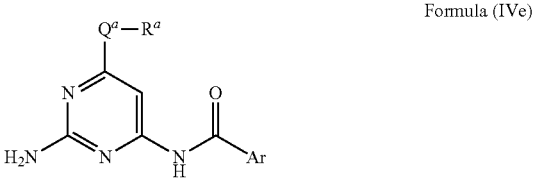

Formula (IVe)

wherein symbols in Formula (IVe) are each synonymous with those in Formula (II); and Ar represents an aryl group;

[Chem. 38]

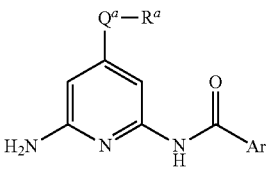

Formula (Ve)

wherein symbols in Formula (Ve) are each synonymous with those in Formula (II); and Ar represents an aryl group.

[22] The polymer film according to any one of [14] to [21], wherein $Q^a$ represents a single bond or —O—, —NH—, or —N(R)— (wherein R is an alkyl group having 1 to 8 carbon atoms); and $R^a$ represents a hydrogen atom, a halogen atom, or an alkyl group having 1 to 8 carbon atoms.

[23] The polymer film according to [15], wherein Formula (II) is Formula (IIIf), (IIIg), (IIIh), (IVf), (IVg), (IVh), or (Vf):

[Chem. 39]

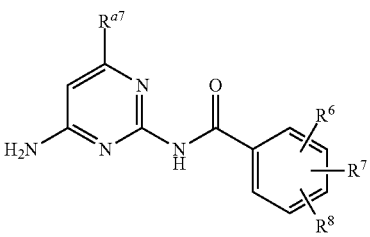

Formula (IIIf)

wherein in Formula (IIIf), $R^{a7}$ represents an alkyl group having 1 to 8 carbon atoms; and $R^6$, $R^7$ and $R^8$ each independently represent a hydrogen atom, a halogen atom, a nitro group, a cyano group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms;

[Chem. 40]

Formula (IIIg)

wherein symbols in Formula (IIIg) are each synonymous with those in Formula (IIIf);

[Chem. 41]

Formula (IIIh)

wherein symbols in Formula (IIIh) are each synonymous with those in Formula (IIIf);

[Chem. 42]

Formula (IVf)

wherein symbols in Formula (IVf) are each synonymous with those in Formula (IIIf);

[Chem. 43]

Formula (IVg)

wherein symbols in Formula (IVg) are each synonymous with those in Formula (IIIf);

[Chem. 44]

Formula (IVh)

wherein symbols in Formula (IVh) are each synonymous with those in Formula (IIIf);

[Chem. 45]

Formula (Vf)

wherein symbols in Formula (Vf) are each synonymous with those in Formula (IIIf).

[24] The polymer film according to any one of [14] to [23], wherein at least one kind of the compounds are added in the form of hydrates of the compounds, solvates of the compounds, or salts of the compounds.

[25] The polymer film according to anyone of [1] to [24], comprising a hydroxyl group-containing polymer as a main component.

[26] The polymer film according to [25], wherein the hydroxyl group-containing polymer is a cellulose acylate resin.

[27] The polymer film according to [26], wherein the cellulose acylate resin is a cellulose acetate resin.

[28] The polymer film according to anyone of [1] to [27], being formed by a solution-casting method.

[29] The polymer film according to [28], wherein the hydrates of the compounds or solvate of the compounds is used.

[30] A retardation film consisting of the polymer film according to any one of [1] to [29] or comprising the polymer film according to any one of [1] to [29].

[31] A polarizing plate comprising a polarizer and the polymer film according to any one of [1] to [29].

[32] A liquid crystal display comprising the polymer film according to any one of [1] to [29] and/or the polarizing plate according to [31].

[33] A compound represented by Formula (7-1) or a hydrate of the compound, a solvate of the compound, or a salt of the compound:

[Chem. 46]

Formula (7-1)

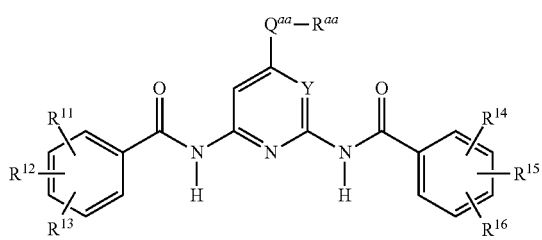

wherein in Formula (7-1), Y represents —N— or —C(-$Q^d$-$R^d$)—, $Q^d$ represents a single bond or a divalent linking group, and $R^d$ represents a hydrogen atom, an alkyl group, an alkenyl group, an alkynyl group, an aryl group, a cyano group, a halogen group, or a heterocyclic group; $Q^{aa}$ represents a single bond or —O—, —S—, —NH—, or —N(R)— (wherein R is an alkyl group having 1 to 8 carbon atoms); $R^{aa}$ represents a hydrogen atom, a halogen atom, or an alkyl group having 1 to 8 carbon atoms, and $R^d$ and $R^{aa}$ are optionally bonded to each other to form a ring structure; and $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms.

[34] A compound represented by Formula (7-2) or a hydrate of the compound, a solvate of the compound, or a salt of the compound:

[Chem. 47]

Formula (7-2)

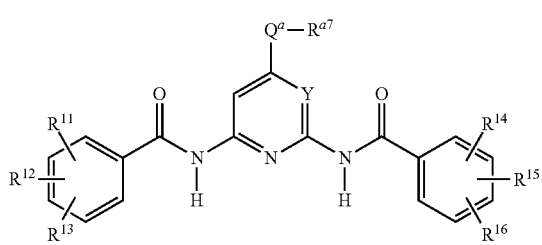

wherein in Formula (7-2), Y represents —N— or —C(-$Q^d$-$R^d$)—, $Q^d$ represents a single bond or a divalent linking group, and $R^d$ represents a hydrogen atom, an alkyl group, an alkenyl group, an alkynyl group, an aryl group, a cyano group, a halogen group, or a heterocyclic group; $Q^a$ represents a single bond or a divalent linking group; $R^{a7}$ represents an alkyl group having 1 to 8 carbon atoms, and $R^d$ and $R^{a7}$ are optionally bonded to each other to form a ring; and $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms.

[35] The compound or a hydrate of the compound, a solvate of the compound, or a salt of the compound according to [33] or [34], the compound being represented by Formula (8), Formula (9), or Formula (10):

[Chem. 48]

Formula (8)

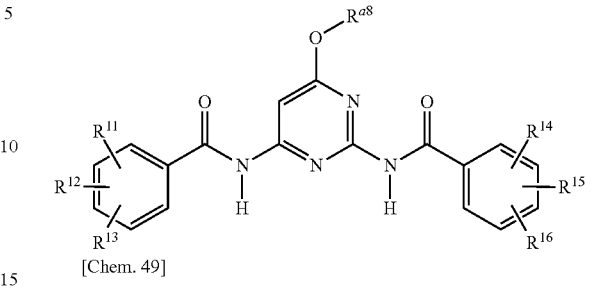

[Chem. 49]

Formula (9)

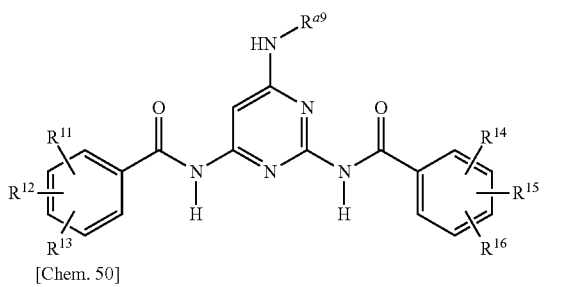

[Chem. 50]

Formula (10)

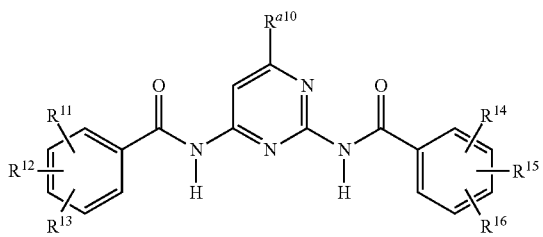

wherein $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms; and $R^{a8}$, $R^{a9}$, and $R^{a10}$ each independently represent an alkyl group having 1 to 8 carbon atoms.

[36] The compound or a hydrate of the compound, a solvate of the compound, or a salt of the compound according to [35], $R^{a8}$, $R^{a9}$, and $R^{a10}$ each independently represent an alkyl group having 1 to 4 carbon atoms.

[37] A compound represented by Formula (IIIc), Formula (IVc), or Formula (Vf) or a hydrate of the compound, a solvate of the compound, or a salt of the compound:

[Chem. 51]

Formula (IIIc)

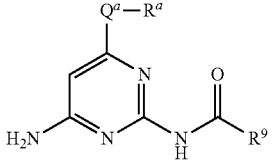

wherein in Formula (IIIc), $Q^a$ represents a single bond or a divalent linking group; $R^a$ represents a hydrogen atom, an alkyl group, an alkenyl group, an alkynyl group, an aryl group, a cyano group, a halogen group, or a heterocyclic group; and $R^9$ represents —O—Ar, an alkyl group, an alkenyl group, an alkynyl group, an aryl group, or a heterocyclic group, wherein Ar represents an aryl group;

[Chem. 52]

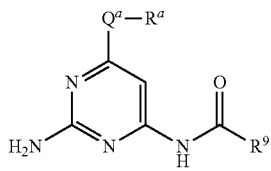

Formula (IVc)

wherein symbols in Formula (IVc) are each synonymous with those in Formula (IIIc);

[Chem. 53]

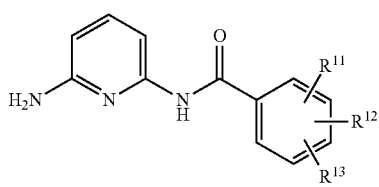

Formula (Vf')

wherein $R^{11}$, $R^{12}$, and $R^{13}$ each independently represent a hydrogen atom, a nitro group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms, provided that at least one of $R^{11}$, $R^{12}$, and $R^{13}$ represents a substituent other than a hydrogen atom.

[38] The compound or a hydrate of the compound, a solvate of the compound, or a salt of the compound according to [37], wherein $Q^a$ represents a single bond or —O—, —NH—, or —N(R)— (wherein R is an alkyl group having 1 to 8 carbon atoms); and $R^a$ represents a hydrogen atom, a halogen atom, or an alkyl group having 1 to 8 carbon atoms.

[39] A compound represented by Formula (IIIf), Formula (IIIg), Formula (IIIh), Formula (IVf), Formula (IVg), or Formula (IVh) or a hydrate of the compound, a solvate of the compound, or a salt of the compound:

[Chem. 54]

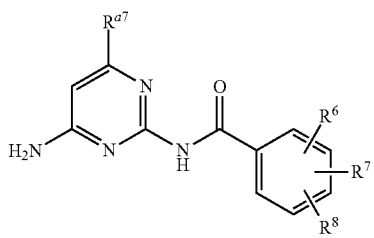

Formula (IIIf)

wherein in Formula (IIIf), $R^{a7}$ represents an alkyl group having 1 to 8 carbon atoms; and $R^6$, $R^7$, and $R^8$ each independently represent a hydrogen atom, a halogen atom, a nitro group, a cyano group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms;

[Chem. 55]

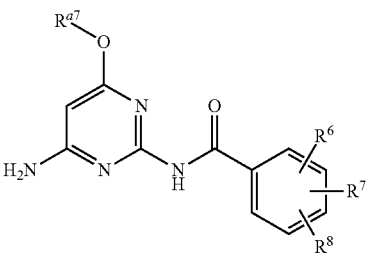

Formula (IIIg)

wherein symbols in Formula (IIIg) are each synonymous with those in Formula (IIIf);

[Chem. 56]

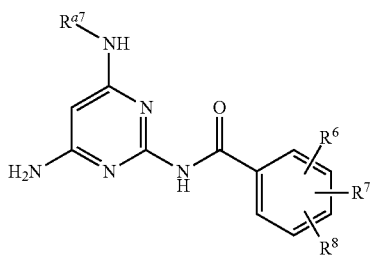

Formula (IIIh)

wherein symbols in Formula (IIIh) are each synonymous with those in Formula (IIIf);

[Chem. 57]

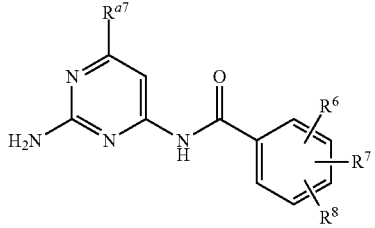

Formula (IVf)

wherein symbols in Formula (IVf) are each synonymous with those in Formula (IIIf);

[Chem. 58]

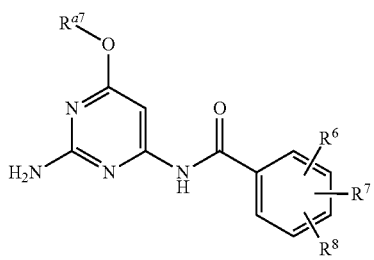

Formula (IVg)

wherein symbols in Formula (IVg) are each synonymous with those in Formula (IIIf);

[Chem. 59]

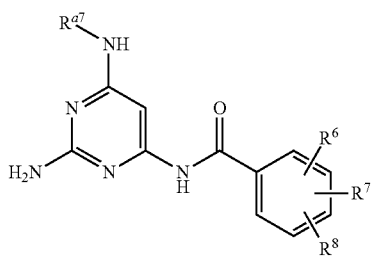

Formula (IVh)

wherein symbols in Formula (IVg) are each synonymous with those in Formula (IIIf).

[40] A hydrate of the compound or a solvate of the compound according to any one of [33] to [39].

[41] A hydrate of the compound according to any one of [33] to [39].

[42] A method of producing a compound represented by Formula (7-1) or a salt of the compound, a hydrate of the compound, or a solvate of the compound, which comprises reacting with a compound represented by Formula (7a), a compound represented by a scheme, and represented by Formula (7b):

[Chem. 60]

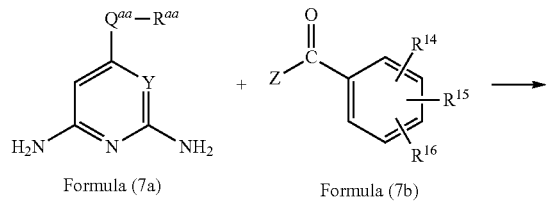

Formula (7a)     Formula (7b)

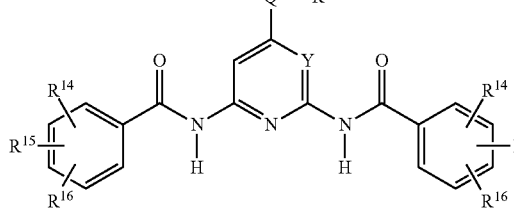

Formula (7-1)

wherein in Formula (7a) and Formula (7b), $Q^{aa}$ represents a single bond or —O—, —S—, —NH—, or —N(R)— (wherein R is an alkyl group having 1 to 8 carbon atoms); $R^{aa}$ represents a hydrogen atom, a halogen atom, or an alkyl group having 1 to 8 carbon atoms; $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms; and Z represents a halogen atom, a hydroxy group, an alkoxy group, aryloxy group, or an acyloxy group.

[43] The method according to [42], further comprising:
crystallizing the compound represented by Formula (7-2) from water or an organic solvent to yield the hydrate of the compound represented by Formula (7-1) or solvate of the compound.

Advantageous Effects of Invention

The present invention can provide a polymer film showing reduced fluctuations in Re and Rth caused by a change in humidity of the operating environment and a retardation film, a polarizing plate, and a liquid crystal display that include the polymer film.

The invention can also provide a novel compound showing high solution stability and being useful in various purposes, such as an additive for polymer films.

BRIEF DESCRIPTION OF DRAWING

FIG. 1 is a schematic diagram showing the structure of an example liquid crystal display of the present invention.

DESCRIPTION OF EMBODIMENTS

The present invention will now be described in detail. The constituent requirement described below may be based on a typical embodiment of the present invention; however, the present invention should not be limited thereto. Throughout the specification, a numerical range defined with "to" is meant to include the numbers preceding and following the "to" as the lower limit and the upper limit, respectively.

Terms used in the specification will now be described.
(Retardation (Re and Rth))

In this description, Re (λ) and Rth (λ) are retardation (nm) in plane and retardation (nm) along the thickness direction, respectively, at a wavelength of λ. Re(λ) is measured by applying light having a wavelength of λ nm to a film in the normal direction of the film, using KOBRA 21ADH or WR (by Oji Scientific Instruments). The selection of the measurement wavelength may be conducted according to the manual-exchange of the wavelength-selective-filter or according to the exchange of the measurement value by the program.

When a film to be analyzed is expressed by a monoaxial or biaxial index ellipsoid, Rth(λ) of the film is calculated as follows.

Rth (λ) is calculated by KOBRA 21ADH or WR on the basis of the six Re(λ) values which are measured for incoming light of a wavelength λ nm in six directions which are decided by a 10° step rotation from 0° to 50° with respect to the normal direction of a sample film using an in-plane slow axis, which is decided by KOBRA 21ADH, as an inclination axis (a rotation axis; defined in an arbitrary in-plane direction if the film has no slow axis in plane), a value of hypothetical mean refractive index, and a value entered as a thickness value of the film.

In the above, when the film to be analyzed has a direction in which the retardation value is zero at a certain inclination angle, around the in-plane slow axis from the normal direction as the rotation axis, then the retardation value at the inclination angle larger than the inclination angle to give a zero retardation is changed to negative data, and then the Rth(λ) of the film is calculated by KOBRA 21ADH or WR.

Around the slow axis as the inclination angle (rotation angle) of the film (when the film does not have a slow axis, then its rotation axis may be in any in-plane direction of the film), the retardation values are measured in any desired inclined two directions, and based on the data, and the estimated value of the mean refractive index and the inputted film thickness value, Rth may be calculated according to formulae (X) and (XI):

(X)

[Math. 1]

$$Re(\theta) = \left[ nx - \frac{(ny \times nz)}{\sqrt{\left(ny \sin\left(\sin^{-1}\left(\frac{\sin(-\theta)}{nx}\right)\right)\right)^2 + \left(nz \cos\left(\sin^{-1}\left(\frac{\sin(-\theta)}{nx}\right)\right)\right)^2}} \right] \times \frac{d}{\cos\left(\sin^{-1}\left(\frac{\sin(-\theta)}{nx}\right)\right)}$$

Re(θ) represents a retardation value in the direction inclined by an angle θ from the normal direction; nx represents a refractive index in the in-plane slow axis direction; ny represents a refractive index in the in-plane direction perpendicular to nx; and nz represents a refractive index in the direction perpendicular to nx and ny. And "d" is a thickness of the film.

$$Rth=\{(nx+ny)/2-nz\} \times d \qquad (XI):$$

In the formula, nx represents a refractive index in the in-plane slow axis direction; ny represents a refractive index in the in-plane direction perpendicular to nx; and nz represents a refractive index in the direction perpendicular to nx and ny. And "d" is a thickness of the film.

When the film to be analyzed is not expressed by a monoaxial or biaxial index ellipsoid, or that is, when the film does not have an optical axis, then Rth(λ) of the film may be calculated as follows:

Re(λ) of the film is measured around the slow axis (judged by KOBRA 21ADH or WR) as the in-plane inclination axis (rotation axis), relative to the normal direction of the film from −50 degrees up to +50 degrees at intervals of 10 degrees, in 11 points in all with a light having a wavelength of λ nm applied in the inclined direction; and based on the thus-measured retardation values, the estimated value of the mean refractive index and the inputted film thickness value, Rth(λ) of the film may be calculated by KOBRA 21ADH or WR.

In the above-described measurement, the hypothetical value of mean refractive index is available from values listed in catalogues of various optical films in Polymer Handbook (John Wiley & Sons, Inc.). Those having the mean refractive indices unknown can be measured using an Abbe refract meter. Mean refractive indices of some main optical films are listed below:

cellulose acylate (1.48), cycloolefin polymer (1.52), polycarbonate (1.59), polymethylmethacrylate (1.49) and polystyrene (1.59). KOBRA 21ADH or WR calculates nx, ny and nz, upon enter of the hypothetical values of these mean refractive indices and the film thickness. On the basis of thus-calculated nx, ny and nz, Nz=(nx−nz)/(nx−ny) is further calculated.

In the present invention, the "slow axis" of, for example, a retardation film represents the direction showing a maximum refractive index. The term "visible light region" covers 380 to 780 nm. The refractive index is measured at a wavelength λ of 589 nm in a visible light region, unless specifically mentioned.

Throughout the specification, numerical values, numerical ranges, and qualitative expressions (expressions such as "equivalent" and "equal") showing the optical characteristics of each component such as a retardation film and a liquid crystal layer are interpreted to be numerical values, numerical ranges, and characteristics including errors generally acceptable for liquid crystal displays and components thereof.

1. Polymer Film

The polymer film of the present invention contains at least one kind of the compounds represented by Formula (0) shown below, hydrates of the compounds, solvates of the compounds, and salts of the compounds. The compound represented by Formula (0) or a hydrate of the compound, solvate of the compound, or salt of the compound functions as a retardation enhancer, and the polymer film containing such a compound has higher Re and/or Rth compared to a polymer film produced by the same materials and the same process except that the compound is not contained. In addition, the variation in at least one of the Re and Rth caused by a change in humidity of the operating environment is reduced in the polymer film having controlled Re and/or Rth by a compound represented by Formula (0) or a hydrate of the compound, solvate of the compound, or salt of the compound, compared to the polymer film having controlled Re and/or Rth by any other retardation enhancer (e.g., disk-shaped compound having a triazine ring as the central core).

Furthermore, in an embodiment of producing a polymer film by a liquid film forming process, i.e., formation of a polymer film from a dope prepared by dissolving a polymer material (which is a term including both resin and polymer) as a main component and a component represented by Formula (0) in an organic solvent, the compound represented by Formula (0) is preferably in a hydrate, solvate, or salt form, more preferably in a hydrate or solvate form, from the viewpoint of quality stabilization of the produced film.

Various materials and methods that can be used for producing the polymer film of the present invention will now be described in detail.

(1-1) Compound represented by Formula (0) or hydrate of the compound, solvate of the compound, or salt of the compound.

The polymer film of the present invention contains at least one of compounds represented by Formula (0) shown below and hydrates of the compounds, solvates of the compounds, and salts of the compounds (hereinafter, may be referred to as "inventive compound"). The compound represented by Formula (0) or a hydrate of the compound, solvate of the compound, or a salt of the compound has an enhancing effect on the Re and/or Rth of a polymer film, in other words, the compound functions as a retardation enhancer. A polymer film containing a hydrophilic polymer, in particular, a hydroxyl group-containing polymer, as a main component tends to increase the fluctuations in Re and Rth caused by a change in humidity of operating environment. The compound represented by Formula (0) or a hydrate of the compound, solvate of the compound, or salt of the compound has a function of reducing at least one of the fluctuations in Re and Rth caused by a change in humidity of operating environment, in other words, the compound also functions as a humidity-dependency reducer for polymer films.

In the present invention, the "humidity-dependency reducer for polymer film" is an agent that can reduce the fluctuations in Re and/or Rth of a polymer film containing the agent, where the fluctuations depend on the moisture of the polymer film. Specifically, an agent-free polymer film to be tested and an agent-containing polymer film are prepared; the Re and the Rth (also referred to as Re [25° C., RH10%] and Rth [25° C., RH10%], respectively) of these polymer films humidified at a relative humidity of 10% at 25° C. for 12 hours and the Re and the Rth (also referred to as Re [25° C., RH80%] and Rth [25° C., RH80%], respectively) of the polymer films humidified at a relative humidity of 80% at 25° C. for 12 hours are measured and compared to each other. If the fluctuation in the Re and/or Rth of the agent-containing polymer film is smaller than that of the agent-free polymer film, the agent is termed a humidity-dependency reducer.

In addition, the compound represented by Formula (0) or a hydrate of the compound, solvate of the compound, or salt of the compound is highly stable in a state dissolved in an organic solvent. Accordingly, use of such a compound contributes to an improvement in stability in production of a polymer film, in particular, production by a solution-casting method.

Throughout the specification, the terms "alkyl group", "alkenyl group", and "alkynyl group" each include both linear and branched groups.

[Chem. 61]

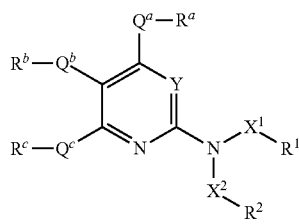

Formula (0)

In Formula (0), Y represents —N— or —C(-$Q^d$-$R^d$)—; $Q^a$, $Q^b$, $Q^c$, and $Q^d$ each independently represent a single bond or a divalent linking group; $R^a$, $R^b$, $R^c$, and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring; $X^2$ represents a single bond or a divalent linking group; $X^1$ represents a single bond or a divalent group selected from a divalent linking group $G^1$ shown below; and $R^1$ and $R^2$ each independently represent a hydrogen atom, an alkyl group, an alkenyl group, an alkynyl group, an aryl group, or a heterocyclic group, wherein $R^1$ and $R^2$ are optionally bonded to each other to form a ring.

The compounds represented by Formula (0) are classified into a compound group A and a compound group B. The compound group A excludes compounds in which only one of -$Q^c$-$R^c$ and —N($X^1R^1$)$X^2R^2$ is —$NH_2$ and compounds in which Y is a nitrogen atom, both -$Q^c$-$R^c$ and —N($X^1R^1$)$X^2R^2$ are not —$NH_2$, and -$Q^a$-$R^a$ is —$NH_2$, i.e., excludes monoamines having the partial structures shown below; and the compound group B includes monoamines having the partial structures shown below. Compounds belonging to the compound group A and the compound group B will now be separately described.

[Chem. 62]

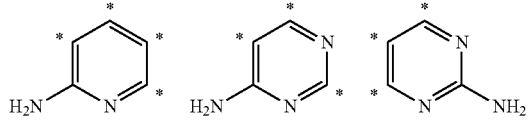

In the formulae, the symbol * each denotes a position to which any one of $Q^a$-$R^a$, -$Q^b$-$R^b$, -$Q^c$-$R^c$, -$Q^d$-$R^d$, and —N($X^1R^1$)$X^2R^2$ bonds and represents a substituent other than $NH_2$.

(1a-1) the Compound Group A

Compounds belonging to the compound group A are represented by Formula (1) and are preferably represented by Formula (2).

[Chem. 63]

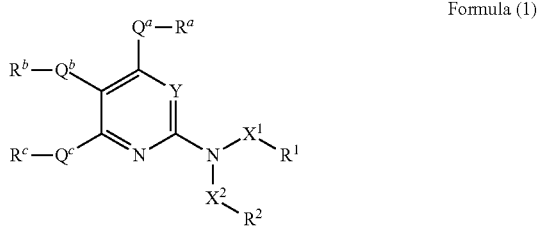

Formula (1)

In Formula (1), Y represents —N— or —C(-$Q^d$-$R^d$)—; $Q^a$, $Q^b$, $Q^c$, and $Q^d$ each independently represent a single bond or a divalent linking group; $R^a$, $R^b$ and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, $R^a$ and $R^d$ are optionally bonded to each other to form a ring; $X^2$ represents a single bond or a divalent linking group; $X^1$ represents a single bond or a divalent group selected from the divalent linking group $G^1$ shown below; and $R^1$ and $R^2$ each independently represent a hydrogen atom, an alkyl group, an alkenyl group, an alkynyl group, an aryl group, or a heterocyclic group, wherein $R^1$ and $R^2$ are optionally bonded to each other to form a ring.

In the compounds mentioned above, compounds in which only one of -$Q^c$-$R^c$ and —N($X^1R^1$)$X^2R^2$ is —$NH_2$ and compounds in which Y is a nitrogen atom, both -$Q^c$-$R^c$ and —N($X^1R^1$) $X^2R^2$ are not —$NH_2$, and -$Q^a$-$R^a$ is —$NH_2$ are excluded, that is, monoamines having the partial structures shown below are excluded.

[Chem. 64]

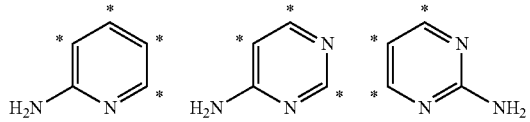

In the formulae, the symbol * each denotes a position to which any one of -$Q^a$-$R^a$, -$Q^b$-$R^b$, -$Q^c$-$R^c$, -$Q^d$-$R^d$, and —N($X^1R^1$)$X^2R^2$ bonds and represents a substituent other than NH$_2$.

[Chem. 65]

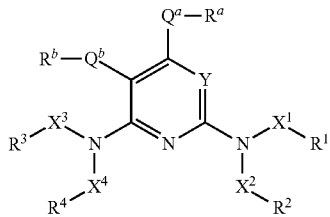

Formula (2)

Symbols in Formula (2) are each synonymous with those in Formula (1); $X^4$ represents a single bond or a divalent linking group; $X^3$ represents a single bond or a divalent group selected from the divalent linking group $G^1$ shown below; and $R^3$ and $R^4$ each independently represent a hydrogen atom, an alkyl group, an alkenyl group, an alkynyl group, an aryl group, or a heterocyclic group, wherein $R^3$ and $R^4$ are optionally bonded to each other to forma ring, provided that compounds in which only one of —N($X^3R^3$)$X^4R^4$ and —N($X^1R^1$)$X^2R^2$ is —NH$_2$ and compounds in which Y is a nitrogen atom, both -$Q^c$-$R^c$ and —N($X^1R^1$)$X^2R^2$ are not —NH$_2$, and -$Q^a$-$R^a$ is —NH$_2$ are excluded.

In Formulae (1) and (2), the 6-membered ring is a pyridine ring when Y represents —C(-$Q^d$-$R^d$)— and is a pyrimidine ring when Y represents —N—.

In Formulae (1) and (2), examples of the each divalent linking group represented by $Q^a$, $Q^b$, $Q^c$, or $Q^d$ include —O—, —S—, —N($X^a$—$R^h$)—, and —N($X^a$—$R^h$)—$X^h$—. Herein, $X^a$ and $X^b$ each independently represent a single bond or a divalent linking group. Examples of the divalent liner represented by $X^a$ or $X^b$ include —CO—, —COO—, and —CONH—. $R^h$ represents a hydrogen atom, an alkyl group having 1 to 8 carbon atoms, an alkenyl group having 2 to 8 carbon atoms, an alkynyl group having 2 to 8 carbon atoms, an aryl group having 6 to 10 carbon atoms, or a heterocyclic group having 2 to 10 carbon atoms. Preferred examples of the each divalent linking group represented by $Q^a$, $Q^b$, $Q^c$ or $Q^d$ include single bonds, —O—, —S—, —N($X^a$—$R^h$)—, and —N($X^a$—$R^h$)—$X^b$—; and the divalent linking group is more preferably a single bond, —O—, —N($X^a$—$R^h$)—, or —N($X^a$—$R^h$)—$X^b$—, and most preferably a single bond, —O—, —NH—, or —NH—$X^b$—. Preferred examples of —NH—$X^b$— include —NH—CO—, —NH—COO—, —NH—CONH—, and —NH—SO$_2$—; and —NH—$X^b$— is more preferably —NH—CO— or —NH—COO—. $Q^d$ preferably represents a single bond.

In Formulae (1) and (2), $R^a$, $R^b$, $R^c$, and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring.

When $R^a$, $R^b$, $R^c$, or $R^d$ each represents the alkyl group, the alkyl group preferably has 1 to 20 carbon atoms, more preferably 1 to 8 carbon atoms, and most preferably 1 to 4 carbon atoms. When $R^a$, $R^b$, $R^c$, or $R^d$ each represents the alkyl group, one carbon atom or non-adjacent two or more carbon atoms are each optionally replaced by a hetero atom selected from oxygen, sulfur, and nitrogen atoms (including —NH— and —N(R)— (R: alkyl group)). For example, $R^a$, $R^b$, $R^c$, and $R^d$ may each be an alkylene (e.g., ethylene or propylene) oxy group.

When $R^a$, $R^b$, $R^c$, or $R^d$ each represents the alkenyl group, the alkenyl group preferably has 2 to 20 carbon atoms, more preferably 2 to 8 carbon atoms, and most preferably 2 to 4 carbon atoms.

When $R^a$, $R^b$, $R^c$, or $R^d$ each represents the alkynyl group, the alkynyl group preferably has 2 to 20 carbon atoms, more preferably 2 to 8 carbon atoms, and most preferably 2 to 4 carbon atoms.

When $R^a$, $R^b$, $R^c$, or $R^d$ each represents the aryl group, the aryl group preferably has 6 to 24 carbon atoms, more preferably 6 to 18 carbon atoms, and most preferably 6 to 10 carbon atoms, from the viewpoint of reducing humidity dependency. Specifically, the aryl group is preferably a benzene ring or a naphthalene ring and most preferably a benzene ring.

When $R^a$, $R^b$, $R^c$, or $R^d$ each represents the heterocyclic group, the heterocyclic group preferably has 4 to 20 carbon atoms, more preferably 4 to 10 carbon atoms, and most preferably 4 to 6 carbon atoms, from the viewpoint of reducing humidity dependency. Specific examples of the heterocyclic group include pyrrolyl group, pyrrolidino group, pyrazolyl group, pyrazolidino group, imidazolyl group, piperazino group, and morpholino group.

$R^a$ and $R^b$, and $R^a$ and $R^d$ are optionally bonded to each other to form a ring. The ring to be formed may be a hydrocarbon ring or a heterocycle and is preferably a 5-membered or 6-membered ring.

$R^a$, $R^b$, $R^c$, and $R^d$ each optionally further have one or more substituents, if possible. Examples of the substituent optionally possessed by $R^a$, $R^b$, $R^c$, or $R^d$ include the following substituent group T.

Substituent Group T:

Alkyl groups (those preferably having 1 to 20 carbon atoms, more preferably 1 to 12 carbon atoms, and most preferably 1 to 8 carbon atoms, and examples thereof include methyl group, ethyl group, isopropyl group, tert-butyl group, n-octyl group, n-decyl group, n-hexadecyl group, cyclopropyl group, cyclopentyl group, and cyclohexyl group); alkenyl groups (those preferably having 2 to 20 carbon atoms, more preferably 2 to 12 carbon atoms, and most preferably 2 to 8 carbon atoms, and examples thereof include vinyl group, allyl group, 2-butenyl group, and 3-pentenyl group), alkynyl groups (those preferably having 2 to 20 carbon atoms, more preferably 2 to 12 carbon atoms, and most preferably 2 to 8 carbon atoms, and examples thereof include propargyl group and 3-pentynyl group), aryl groups (those preferably having 6 to 30 carbon atoms, more preferably 6 to 20 carbon atoms, and most preferably 6 to 12 carbon atoms, and examples thereof include phenyl group, biphenyl group, and naphthyl group), amino groups (those preferably having 0 to 20 carbon atoms, more preferably 0 to 10 carbon atoms, and most preferably 0 to 6 carbon atoms, and examples thereof include amino group, methylamino group, dimethylamino group, diethylamino group, and dibenzylamino group), alkoxy group (those preferably having 1 to 20 carbon atoms, more preferably 1 to 12 carbon atoms, and most preferably 1 to 8 carbon atoms, and examples thereof include methoxy group, ethoxy group, and butoxy group), aryloxy groups (those preferably having 6 to 20 carbon atoms, more preferably 6 to 16 carbon atoms, and most preferably 6 to 12 carbon atoms, and examples thereof include phenyloxy group and 2-naphthyloxy group), acyl groups (those preferably having 1 to 20 carbon atoms, more preferably 1 to 16 carbon atoms, and most preferably 1 to 12 carbon atoms, and examples thereof include acetyl group, benzoyl group, formyl group, and pivaloyl group), alkoxycarbonyl groups (those preferably having 2 to 20 carbon atoms, more preferably 2 to 16 carbon atoms, and most preferably 2 to 12 carbon atoms, and examples thereof include methoxycarbonyl group and ethoxycarbonyl group), aryloxycarbonyl groups (those preferably having 7 to 20 carbon atoms, more preferably 7 to 16 carbon atoms, and most preferably 7 to 10 carbon atoms, and examples thereof include phenyloxycarbonyl group), acyloxy groups (those preferably having 2 to 20 carbon atoms, more preferably 2 to 16 carbon atoms, and most preferably 2 to 10 carbon atoms, and examples thereof include acetoxy group and benzoyloxy group), acylamino groups (those preferably having 2 to 20 carbon atoms, more preferably 2 to 16 carbon atoms, and most preferably 2 to 10 carbon atoms, and examples thereof include acetylamino group and benzoylamino group), alkoxycarbonylamino groups (those preferably having 2 to 20 carbon atoms, more preferably 2 to 16 carbon atoms, and most preferably 2 to 12 carbon atoms, and examples thereof include methoxycarbonylamino group), aryloxycarbonylamino groups (those preferably having 7 to 20 carbon atoms, more preferably 7 to 16 carbon atoms, and most preferably 7 to 12 carbon atoms, and examples thereof include phenyloxycarbonylamino group), sulfonylamino groups (those preferably having 1 to 20 carbon atoms, more preferably 1 to 16 carbon atoms, and most preferably 1 to 12 carbon atoms, and examples thereof include methanesulfonylamino group and benzenesulfonylamino group), sulfamoyl groups (those preferably having 0 to 20 carbon atoms, more preferably 0 to 16 carbon atoms, and most preferably 0 to 12 carbon atoms, and examples thereof include sulfamoyl group, methylsulfamoyl group, dimethylsulfamoyl group, and phenylsulfamoyl group), carbamoyl groups (those preferably having 1 to 20 carbon atoms, more preferably 1 to 16 carbon atoms, and most preferably 1 to 12 carbon atoms, and examples thereof include carbamoyl group, methylcarbamoyl group, diethylcarbamoyl group, and phenylcarbamoyl group), alkylthio groups (those preferably having 1 to 20 carbon atoms, more preferably 1 to 16 carbon atoms, and most preferably 1 to 12 carbon atoms, and examples thereof include methylthio group and ethylthio group), arylthio groups (those preferably having 6 to 20 carbon atoms, more preferably 6 to 16 carbon atoms, and most preferably 6 to 12 carbon atoms, and examples thereof include phenylthio group), sulfonyl groups (those preferably having 1 to 20 carbon atoms, more preferably 1 to 16 carbon atoms, and most preferably 1 to 12 carbon atoms, and examples thereof include mesyl group and tosyl group), sulfinyl groups (those preferably having 1 to 20 carbon atoms, more preferably 1 to 16 carbon atoms, and most preferably 1 to 12 carbon atoms, and examples thereof include methanesulfinyl group and benzenesulfinyl group), ureido groups (those preferably having 1 to 20 carbon atoms, more preferably 1 to 16 carbon atoms, and most preferably 1 to 12 carbon atoms, and examples thereof include ureido group, methylureido group, and phenylureido group), phosphoric amido groups (those preferably having 1 to 20 carbon atoms, more preferably 1 to 16 carbon atoms, and most preferably 1 to 12 carbon atoms, and examples thereof include diethylphosphoric amide and phenylphosphoric amide), a hydroxyl group, a mercapto group, halogen atoms (e.g., fluorine atom, chlorine atom, bromine atom, and iodine atom), a cyano group, a sulfo group, a carboxyl group, a nitro group, a hydroxamic acid group, a sulfino group, a hydrazino group, an imino group, heterocycles (those preferably having 1 to 30 carbon atoms and more preferably 1 to 12 carbon atoms, examples of the hetero atom include nitrogen atom, oxygen atom, sulfur atom, and specific examples of the heterocycle include imidazolyl group, pyridyl group, quinolyl group, furyl group, piperidyl group, morpholino group, benzoxazolyl group, benzimidazolyl group, and benzthiazolyl group), and silyl groups (those preferably having 3 to 40 carbon atoms, more preferably 3 to 30 carbon atoms, and most preferably 3 to 24 carbon atoms, and examples thereof include trimethylsilyl group and triphenylsilyl group).

These substituents may further have substituents. When the substituent belonging to the substituent group T has two or more substituents, the substituents may be the same or different and may be bonded to each other to form a ring, if possible.

In Formulae (1) and (2), $R^a$ and $R^b$ are each preferably a hydrogen atom or a substituted or unsubstituted alkyl group. In Formula (1), $R^c$ is preferably a hydrogen atom, a substituted or unsubstituted alkyl group, a substituted or unsubstituted aryl group, or a substituted or unsubstituted heterocyclic group. It is preferable that $R^d$ is a hydrogen atom and $Q^d$ is a single bond, in other words, Y represented by —C(-$Q^d$-$R^d$)— is preferably unsubstituted methine.

Examples of the compound represented by Formula (1) and (2) include compounds in which Y is a nitrogen atom, and -$Q^a$-$R^a$ and -$Q^c$-$R^c$ each are groups other than —OH and —SH.

Examples of the compound represented by Formula (1) or (2) are not limited to those having structures specified by Formula (1) or (2) and include those having resonance structures of the heterocyclic skeletons specified by Formula (1) or (2). Furthermore, examples of the compound represented by Formula (1) or (2) include those having structures of which the heterocyclic skeletons resonating with -$Q^a$-$R^a$ or -$Q^c$-$R^c$. The same applies to compounds represented by Formulae (3) to (12) described below.

In Formulae (1) and (2), $R^1$, $R^2$, $R^3$, and $R^4$ each independently represent a hydrogen atom, an alkyl group, an alkenyl group, an alkynyl group, an aryl group, or a heterocyclic group, wherein any two of $R^1$, $R^2$, $R^3$, and $R^4$ are optionally bonded to each other to form a ring.

When $R^1$, $R^2$, $R^3$, or $R^4$ each represents the alkyl group, the alkyl group preferably has 1 to 20 carbon atoms, more preferably 1 to 8 carbon atoms, and most preferably 1 to 4 carbon atoms. when $R^1$, $R^2$, $R^3$, or $R^4$ each represents the alkyl group, one carbon atom or non-adjacent two or more carbon atoms are each optionally replaced by a hetero atom selected from oxygen atom, sulfur atom, and nitrogen atom (including —NH— and —N(R)— (R: alkyl group)). For example, $R^1$, $R^2$, $R^3$, and $R^4$ may each be an alkylene (e.g., ethylene or propylene) oxy group.

When $R^1$, $R^2$, $R^3$, or $R^4$ each represents the alkenyl group, the alkenyl group preferably has 2 to 20 carbon atoms, more preferably 2 to 8 carbon atoms, and most preferably 2 to 4 carbon atoms.

When $R^1$, $R^2$, $R^3$, or $R^4$ each represents the alkynyl group, the alkynyl group preferably has 2 to 20 carbon atoms, more preferably 2 to 8 carbon atoms, and most preferably 2 to 4 carbon atoms.

When $R^1$, $R^2$, $R^3$, or $R^4$ each represents the aryl group, the aryl group preferably has 6 to 24 carbon atoms, more preferably 6 to 18 carbon atoms, and most preferably 6 to 10 carbon atoms, from the viewpoint of reducing humidity dependency. Specifically, the aryl group is preferably a benzene ring or a naphthalene ring and most preferably a benzene ring.

When $R^1$, $R^2$, $R^3$, or $R^4$ each represents the heterocyclic group, the heterocyclic group preferably has 4 to 20 carbon atoms, more preferably 4 to 10 carbon atoms, and most preferably 4 to 6 carbon atoms, from the viewpoint of reducing humidity dependency. Specific examples of the heterocyclic group include pyrrolyl group, pyrrolidino group, pyrazolyl group, pyrazolidino group, imidazolyl group, piperazino group, and morpholino group.

In Formulae (1) and (2), it is preferable that $R^1$, $R^2$, $R^3$ and $R^4$ be each independently a hydrogen atom, an alkyl group, an aryl group, or a heterocyclic group.

$R^1$, $R^2$, $R^3$, and $R^4$ each optionally further have one or more substituents, if possible. Examples of the substituent optionally possessed by $R^1$, $R^2$, $R^3$, or $R^4$ include those belonging to the substituent group T mentioned above.

In Formulae (1) and (2), it is preferable that $R^1$, $R^2$, $R^3$, and $R^4$ be each independently a hydrogen atom, a substituted or unsubstituted alkyl group, a substituted or unsubstituted aryl group, or a substituted or unsubstituted heterocyclic group.

Either $R^1$ or $R^2$ and either $R^3$ or $R^4$ are each preferably a hydrogen atom or a substituted or unsubstituted alkyl group, and most preferably a hydrogen atom. The other substituents are preferably substituted or unsubstituted aryl groups from the viewpoint of reducing humidity dependency.

In Formulae (1) and (2), $X^2$ and $X^4$ each independently represent a single bond or a divalent linking group; $X^1$ and $X^3$ each represent a single bond or a group selected from the divalent linking group $G^1$ shown below.

Examples of the each divalent linking groups represented by $X^2$ or $X^4$ include alkylene groups (preferably having 1 to 30 carbon atoms, more preferably 1 to 3 carbon atoms, and most preferably two carbon atoms) and arylene groups (preferably having 6 to 30 carbon atoms and more preferably 6 to 10 carbon atoms). Examples of the divalent linking groups represented by $X^1$ or $X^3$ include those belonging to the divalent linking group $G^1$.

[Chem. 66]

Divalent linking group $G^1$

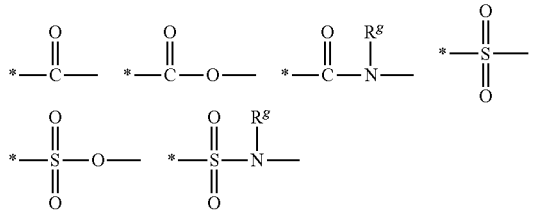

In each formula, the side indicated by symbol * is a bonding site to the nitrogen atom introduced into the pyrimidine ring or pyridine ring in the compound represented by each formula; and $R^g$ represents a hydrogen atom, an alkyl group, an alkenyl group, an alkynyl group, an aryl group, or a heterocyclic group. The preferred range of the number of carbon atoms in each group is the same as the preferred range of the number of carbon atoms in each group represented by $X^a$ or $X^b$.

Preferably, $X^1$ and $X^3$ are each independently selected from a divalent linking group $G^2$.

[Chem. 67]

Divalent linking group $G^2$

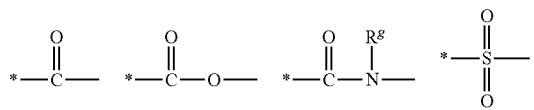

Symbols in the divalent linking group $G^2$ are synonymous with those in the divalent linking group $G^1$.

Preferably, $X^1$ and $X^3$ are each independently a single bond or a group selected from the divalent linking group $G^1$. More preferably, $X^2$ is a single bond, $X^1$ represents a group selected from the divalent linking group $G^1$, $X^4$ is a single bond, and $X^3$ represents a group selected from the divalent linking group $G^1$.

More preferably, in such a case, $X^1$ and $X^3$ are each independently any one of —CO—, —COO—, and —CO(NR$^g$)— and most preferably —CO—.

For example, when $X^1$ is a prescribed divalent linking group (most preferably —CO—) and when $X^2$ is a single bond, $R^1$ is preferably a substituted or unsubstituted alkyl group, a substituted or unsubstituted aryl group, or a substituted or unsubstituted heterocyclic group (preferably a substituted or unsubstituted aryl group, from the viewpoint of reducing humidity dependency), and $R^2$ is preferably a hydrogen atom. Similarly, when $X^3$ is a prescribed divalent linking group (preferably —CO—) and when $X^4$ is a single bond, $R^3$ is preferably a substituted or unsubstituted alkyl group, a substituted or unsubstituted aryl group, or a substituted or unsubstituted heterocyclic group (preferably a substituted or unsubstituted aryl group, from the viewpoint of reducing humidity dependency) and $R^4$ is preferably a hydrogen atom.

Furthermore, in Formula (1), when $X^1$ is a prescribed divalent linking group, $R^1$ is preferably an aryl group, in particular, a substituted or unsubstituted phenyl group. The aryl group optionally has one or more substituents selected from the substituent group T. The substituent may be introduced into any position and may be introduced into one of the ortho-, meta-, and para-positions relative to $X^1$. Preferred examples of the substituent include halogen atoms, a hydroxyl group, a carbamoyl group, a sulfamoyl group, alkyl groups (preferably alkyl group having 1 to 8 carbon atoms), alkoxy groups (preferably alkoxy group having 1 to 8 carbon atom), alkylamino groups (preferably alkylamino groups having 1 to 8 carbon atoms), and dialkylamino groups (preferably dialkylamino groups having 1 to 8 carbon atoms). Alkyl groups (preferably alkyl groups having 1 to 8 carbon atoms) and alkoxy groups (preferably alkoxy groups having 1 to 8 carbon atoms) are more preferred, and alkyl groups and alkoxy groups having 1 to 4 carbon atoms are most preferred.

In Formula (2), when $X^1$ and $X^3$ are divalent linking groups, $R^1$ and $R^3$ are preferably aryl groups, in particular, substituted or unsubstituted phenyl groups. The aryl group optionally has one or more substituents selected from the substituent group T. The substituent may be introduced into any position and may be introduced into one of the ortho-, meta-, and para-positions relative to $X^1$ or $X^3$. Preferred examples of the substituent include halogen atoms, a hydroxyl group, a carbamoyl group, a sulfamoyl group, alkyl groups (preferably alkyl groups having 1 to 8 carbon atoms), alkoxy groups (preferably alkoxy groups having 1 to 8 carbon atoms), alkylamino groups (preferably alkylamino groups having 1 to 8 carbon atoms), and dialkylamino groups (preferably dialkylamino groups having 1 to 8 carbon atoms). Alkyl groups (preferably alkyl groups having 1 to 8 carbon atoms) and alkoxy groups (preferably alkoxy groups having 1 to 8 carbon atoms) are more preferred, and alkyl groups and alkoxy groups having 1 to 4 carbon atoms are most preferred.

In Formulae (1) and (2), when all of $X^1$, $X^2$, $X^3$, and $X^4$ are not any of the divalent linking groups belonging to the divalent linking group $G^1$, $X^1$, $X^2$, $X^3$, and $X^4$ are preferably single bonds, and $R^1$, $R^2$, $R^3$, and $R^4$ respectively bonding to $X^1$, $X^2$, $X^3$, $X^4$ are preferably hydrogen atoms. In Formula (2), however, when $X^1$ and $X^2$ are single bonds and when $R^1$ and $R^2$ are hydrogen atoms, $X^3$ and $X^4$ are single bonds, and $R^3$ and $R^4$ are hydrogen atoms. In Formula (1), when $X^1$ and $X^2$ are single bonds and when $R^1$ and $R^2$ are hydrogen atoms, -$Q^c$-$R^c$ is —$NH_2$.

Examples of the compound represented by Formula (1) include compounds represented by Formula (3).

[Chem. 68]

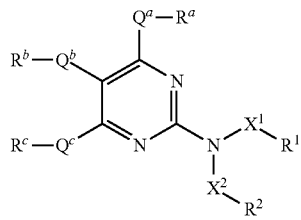

Formula (3)

Symbols in Formula (3) are each synonymous with those in Formula (1), and the preferred ranges and specific examples are also the same. Examples of the compound represented by Formula (3) include compounds of which -$Q^a$-$R^a$ is a group other than —OH and —SH, provided that compounds where only one of -$Q^c$-$R^c$ and —N($X^1R^1$)$X^2R^2$ is —$NH_2$ and compounds where both -$Q^c$-$R^c$ and —N($X^1R^1$)$X^2R^2$ are not —$NH_2$ and -$Q^a$-$R^a$ is —$NH_2$ are excluded.

Examples of the compound represented by Formula (1) include compounds represented by Formula (4).

[Chem. 69]

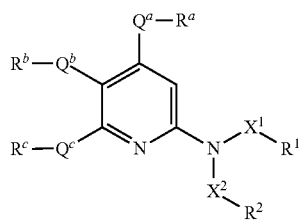

Formula (4)

Symbols in Formula (4) are each synonymous with those in Formula (1), and the preferred ranges and specific examples are also the same, provided that compounds where only one of -$Q^c$-$R^c$ and —N($X^1R^1$)$X^2R^2$ is —$NH_2$ are excluded.

Examples of the compound represented by Formula (1) include compounds represented by Formula (3a).

[Chem. 70]

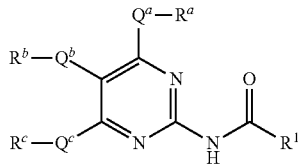

Formula (3a)

Symbols in Formula (3a) are each synonymous with those in Formula (1), and the preferred ranges and specific examples are also the same.

Examples of the compound represented by Formula (1) include compounds represented by Formula (3b).

[Chem. 71]

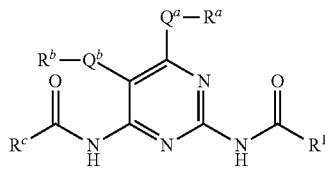

Formula (3b)

Symbols in Formula (3b) are each synonymous with those in Formula (1), and the preferred ranges and specific examples are also the same.

Examples of the compound represented by Formula (1) include compounds represented by Formula (3c).

[Chem. 72]

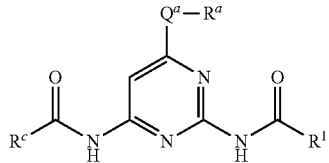

Formula (3c)

Symbols in Formula (3c) are each synonymous with those in Formula (1), and the preferred ranges and specific examples are also the same.

In Formula (1), $Q^a$ is preferably a single bond or a divalent linking group represented by —O—, —S—, —N($X^a$—$R^h$)—, or —N($X^a$—$R^h$)—$X^b$—; more preferably a single bond or —O—, —S—, —NH—, or —N(R)— (wherein R is an alkyl group having 1 to 8 carbon atoms and preferably 1 to 4 carbon atoms); and most preferably a single bond or —O—. $R^a$ is preferably a hydrogen atom, a halogen atom, an alkyl group having 1 to 8 carbon atoms, an alkenyl group having 2 to 8 carbon atoms, an alkynyl group having 2 to 8 carbon atoms, an aryl group having 6 to 18 carbon atoms (e.g., a benzene ring or naphthalene ring group), or a heterocyclic group having 4 to 10 carbon atoms (e.g., a pyrrolyl group, a pyrrolidino group, a pyrazolyl group, a pyrazolidino group, an imidazolyl group, a piperazino group, or a morpholino group); more preferably a hydrogen atom or an alkyl group having 1 to 8 carbon atoms; and most preferably an alkyl group having 1 to 4 carbon atoms. The alkyl group may be substituted, but is preferably unsubstituted. Examples of the substituent include a hydroxyl group, a cyano group, alkoxy groups, alkoxycarbonyl groups, and an amino group. When $Q^a$ is —N(R)—, $R^a$ is optionally bonded to R to form a ring (e.g., 5- or 6-membered ring). Examples of the compound represented by Formula (1) include compounds of which -$Q^a$-$R^a$ is a group other than —OH and —SH.

Preferred examples of -$Q^a$-$R^a$ include —Cl, —CH$_3$, -(t)C$_4$H$_9$, —OH, —OCH$_3$, —OC$_2$H$_5$, —NH$_2$, —NHCH$_3$, NHC$_2$H$_5$, —NHC$_3$H$_7$, —NHC$_4$H$_9$, —N(CH$_3$)$_2$, and —N(C$_2$H$_5$)$_2$. More preferred examples are —Cl, —CH$_3$, —OH, —OCH$_3$, NH$_2$, —NHCH$_3$, and NHC$_2$H$_5$; and most preferred examples are —CH$_3$ and —OCH$_3$.

Examples of the compound represented by Formula (1) include compounds represented by Formula (5-1).

[Chem. 73]

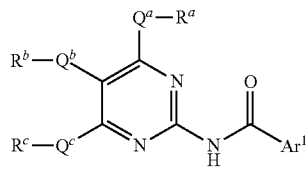

Formula (5-1)

Symbols in Formula (5-1) are each synonymous with those in Formula (1), and the preferred ranges and specific examples are also the same, provided that compounds where only one of -$Q^c$-$R^c$ and -$Q^a$-$R^a$ is NH$_2$ are excluded.

Ar$^1$ represents an aryl group. The aryl group is preferably a substituted or unsubstituted phenyl or naphthyl group and more preferably a substituted or unsubstituted phenyl group. The aryl group represented by Ar$^1$ optionally has one or more substituents. Examples of the substituent include those belonging to the substituent group T, and preferred examples of the substituent are each the same as those possessed by R$^1$ or R$^3$ in Formula (2).

Examples of the compound represented by Formula (1) include compounds represented by Formula (5-2).

[Chem. 74]

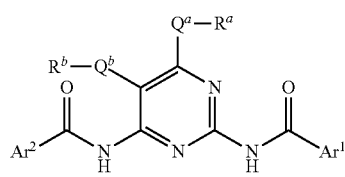

Formula (5-2)

Symbols in Formula (5-2) are each synonymous with those in Formula (1), and the preferred ranges and specific examples are also the same. Ar$^2$ represents an aryl group.

Preferred examples of the compound represented by Formula (1) or (2) include compounds represented by Formula (6).

[Chem. 75]

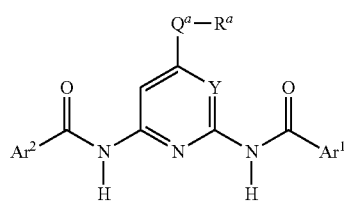

Formula (6)

Symbols in Formula (6) are each synonymous with those in Formula (2). Ar$^1$ and Ar$^2$ each represent an aryl group. Preferred examples of $Q^a$ and $R^a$ are the same as those of each group in Formula (3c).

The aryl group represented by Ar$^1$ or Ar$^2$ is preferably a substituted or unsubstituted phenyl or naphthyl group and more preferably a substituted or unsubstituted phenyl group. The aryl group represented by Ar$^1$ or Ar$^2$ optionally has one or more substituents. Examples of the substituent include those belonging to the substituent group T, and preferred examples of the substituent are the same as those possessed by R$^1$ or R$^3$ in Formula (2). Ar$^1$ and Ar$^2$ may be the same or different from each other. For example, one of them may be an unsubstituted aryl group, and the other may be the same aryl group having one or more substituents. Alternatively, both of them may be the same aryl groups having different substituents.

In an example of synthesizing a compound having Ar$^1$ and Ar$^2$ different from each other in Formula (6) using the respective reagents for introducing Ar$^1$ and Ar$^2$, a mixture of three or four compounds, i.e., a compound having two Ar$^1$s, a compound having two Ar$^2$s, and one or two compounds having Ar$^1$ and Ar$^2$ (when Y is a nitrogen atom, two compounds are specified), may be prepared. In the present invention, such a mixture may be directly used as an additive for polymer films. That is, a mixture of compounds represented by Formulae (6a) to (6d) (or Formulae (6a) to (6c) when Y is a methine group) may be used as an additive.

[Chem. 76]

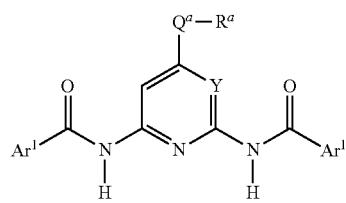

(6a)

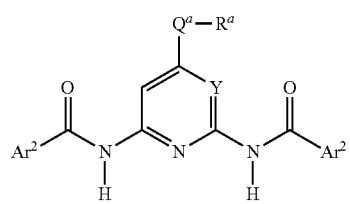

(6b)

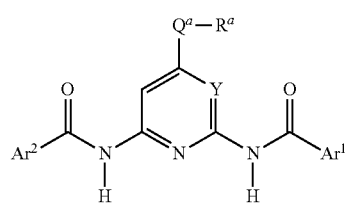

(6c)

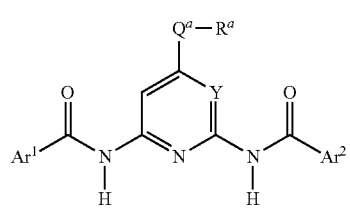

(6d)

Symbols in Formulae (6a) to (6d) are each synonymous with those in Formula (2), provided that Ar$^1$ and Ar$^2$ represent different groups from each other.

$Q^a$ is preferably a single bond or a divalent linking group represented by —O—, —S—, —N($X^a$—$R^h$)—, or —N($X^a$—$R^h$)—$X^b$—; more preferably a single bond or —O—, —S—, —NH—, or —N(R)— (wherein R is an alkyl group having 1 to 8 carbon atoms and preferably 1 to 4 carbon atoms); and most preferably a single bond or —O—.

$R^a$ is preferably a hydrogen atom, a halogen atom, an alkyl group having 1 to 8 carbon atoms, an alkenyl group having 2 to 8 carbon atoms, an alkynyl group having 2 to 8 carbon atoms, an aryl group having 6 to 18 carbon atoms (e.g., a benzene ring or naphthalene ring group), a heterocyclic group having 4 to 10 carbon atoms (e.g., a pyrrolyl group, a pyrrolidino group, a pyrazolyl group, a pyrazolidino group, an imidazolyl group, a piperazino group, or a morpholino group); and more preferably a hydrogen atom, a halogen atom, or an alkyl group having 1 to 8 carbon atoms (more preferably an alkyl group having 1 to 4 carbon atoms). The alkyl group may be substituted, but is preferably unsubstituted. Examples of the substituent include a hydroxyl group, a cyano group, alkoxy groups, alkoxycarbonyl groups, and an amino group. When $Q^a$ is —N(R)—, $R^a$ is optionally bonded to R to form a ring (e.g., 5- or 6-membered ring). Examples of the compound represented by Formula (6) include compounds of which -$Q^a$-$R^a$ is a group other than —OH and —SH.

Preferred examples of -$Q^a$-$R^a$ include —Cl, —$CH_3$, -(t)$C_4H_9$, —OH, —$OCH_3$, —$OC_2H_5$, —$NH_2$, —$NHCH_3$, $NHC_2H_5$, —$NHC_3H_7$, —$NHC_4H_9$, —$N(CH_3)_2$, and —$N(C_2H_5)_2$. More preferred examples are —Cl, —$CH_3$, —OH, —$OCH_3$, $NH_2$, —$NHCH_3$, and $NHC_2H_5$; and most preferred examples are —$CH_3$ and —$OCH_3$.

Preferred examples of the compound represented by Formula (6) include compounds represented by Formula (6-1).

[Chem. 77]

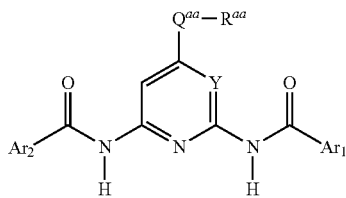

Formula (6-1)

Symbols in Formula (6-1) are each synonymous with those in Formula (6); and $Ar^1$ and $Ar^2$ represent aryl groups.

$Q^{aa}$ represents a single bond or —O—, —NH—, or —N(R)— (wherein R is an alkyl group having 1 to 8 carbon atoms).

$R^{aa}$ represents a hydrogen atom, a halogen atom, or an alkyl group having 1 to 8 carbon atoms.

The preferred ranges of $Ar^1$ and $Ar^2$ are the same as those shown in Formula (6).

The preferred ranges of $Q^{aa}$ and $R^{aa}$ are respectively the same as those of $Q^a$ and $R^a$ in Formula (6).

The compounds represented by Formula (6) and Formulae (7-1), (7-2), and (8) to (10) described below have high retardation-enhancing effects. Polymer films containing these compounds and thereby having controlled Re and/or Rth are characterized by further reduced fluctuations in Re and/or Rth depending on humidity.

Preferred examples of the compound represented by Formula (2) include compounds represented by Formula (7-1).

[Chem. 78]

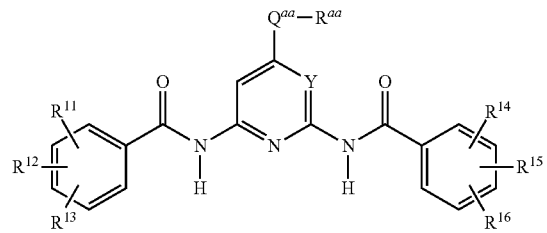

Formula (7-1)

Symbols, Y, $Q^{aa}$, and $R^{aa}$, in Formula (7-1) are each synonymous with those in Formula (6-1); and $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms.

$R^{11}$, $R^{12}$, $R^{13}$, $R^{14}$, $R^{15}$, and $R^{16}$ are each preferably a hydrogen atom, an alkyl group having 1 to 8 carbon atoms, or an alkoxy group having 1 to 8 carbon atoms; and most preferably a hydrogen atom, an alkyl group having 1 to 4 carbon atoms, or an alkoxy group having 1 to 4 carbon atoms. $R^{11}$ to $R^{16}$ may be the same as or different from each other. For example, all of $R^{11}$ to $R^{13}$ are hydrogen atoms, and at least one of $R^{14}$ to $R^{16}$ is a substituent mentioned above; all of $R^{14}$ to $R^{16}$ are hydrogen atoms, and at least one of $R^{11}$ to $R^{13}$ is a substituent mentioned above; or at least one of $R^{11}$ to $R^{13}$ and at least one of $R^{14}$ to $R^{16}$ are substituents mentioned above and different from each other.

The sites into which $R^{11}$, $R^{12}$, $R^{13}$, $R^{14}$, $R^{15}$ and $R^{16}$ are introduced may be any of the ortho-, meta-, and para-positions relative to —C(=O)—, but from the viewpoint of the effect of improving the humidity dependency, the site of the substitution is preferably a position other than the ortho-position.

Preferred examples of -$Q^{aa}$-$R^{aa}$ in Formula (7-1) include —Cl, —$CH_3$, -(t)$C_4H_9$, —OH, —$OCH_3$, —$OC_2H_5$, —$NH_2$, —$NHCH_3$, $NHC_2H_5$, —$NHC_3H_7$, —$NHC_4H_9$, —$N(CH_3)_2$, and —$N(C_2H_5)_2$. More preferred examples are —Cl, —$CH_3$, —OH, —$OCH_3$, $NH_2$, —$NHCH_3$, and $NHC_2H_5$; and most preferred examples are —$CH_3$ and —$OCH_3$.

Furthermore, $R^{11}$, $R^{12}$, $R^{13}$, $R^{14}$, $R^{15}$, and $R^{16}$ in Formula (7-1) are each preferably a hydrogen atom, an alkyl group having 1 to 8 carbon atoms, or an alkoxy group having 1 to 8 carbon atoms and most preferably a hydrogen atom, an alkyl group having 1 to 4 carbon atoms, or an alkoxy group having 1 to 4 carbon atoms.

Preferred examples of the compound represented by Formula (2) include compounds represented by Formula (7-2).

[Chem. 79]

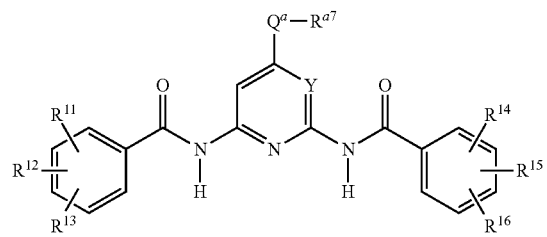

Formula (7-2)

Symbols in Formula (7-2) are each synonymous with those in Formula (2); $Q^a$ represents a single bond or a divalent linking group; $R^{a7}$ represents an alkyl group having 1 to 8 carbon atoms; and $R^{11}$, $R^{12}$, $R^{13}$, $R^{14}$, $R^{15}$ and $R^{16}$ each represent a hydrogen atom, a halogen atom, a carbamoyl group, a sulfamoyl group, an alkyl group having 1 to 8 carbon atoms, or an alkoxy group having 1 to 8 carbon atoms.

$R^{11}$, $R^{12}$, $R^{13}$, $R^{14}$, $R^{15}$, and $R^{16}$ are each preferably a hydrogen atom, an alkyl group having 1 to 8 carbon atoms, or an alkoxy group having 1 to 8 carbon atoms and more preferably a hydrogen atom, an alkyl group having 1 to 4 carbon atoms, or an alkoxy group having 1 to 4 carbon atoms. $R^{11}$ to $R^{16}$ may be the same as or different from each other. For example, all of $R^{11}$ to $R^{13}$ are hydrogen atoms, and at least one of $R^{14}$ to $R^{16}$ is a substituent mentioned above; all of $R^{14}$ to $R^{16}$ are hydrogen atoms, and at least one of $R^{11}$ to $R^{13}$ is a substituent mentioned above; or at least one of $R^{11}$ to $R^{13}$ and at least one of $R^{14}$ to $R^{16}$ are substituents mentioned above and different from each other.

$Q^a$ is preferably a single bond or a divalent linking group represented by —O—, —S—, —N($X^a$—$R^h$)—, or —N($X^a$—$R^h$)—$X^b$—, more preferably a single bond or —O—, —S—, —NH—, or —N(R)— (wherein R is an alkyl group having 1 to 8 carbon atoms and preferably 1 to 4 carbon atoms), and most preferably a single bond or —O— or —NH—.

Preferred examples of the compound represented by Formula (7-1) or (7-2) include compounds represented by Formulae (8) to (10).

[Chem. 80]

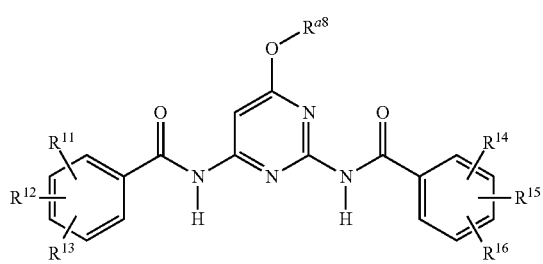

Formula (8)

[Chem. 81]

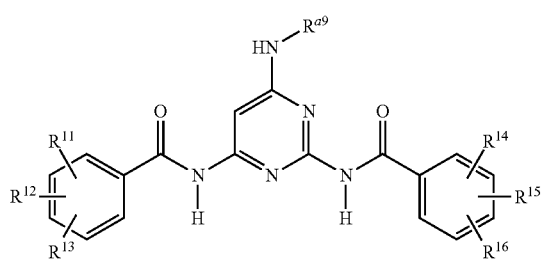

Formula (9)

[Chem. 82]

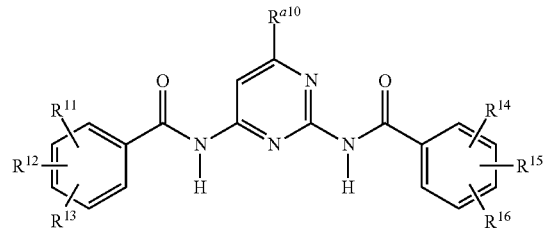

Formula (10)

Symbols in Formulae (8) to (10) are each synonymous with those in Formulae (7-1) and (7-2), and $R^{a8}$, $R^{a9}$, and $R^{a10}$ each represent an alkyl group having 1 to 8 carbon atoms (preferably 1 to 4 carbon atoms).

Examples of the compound represented by Formula (1) include compounds having —NH$_2$ as each of -$Q^c$-$R^c$ and —N($X^1R^1$)$X^2R^2$, i.e., compounds represented by Formula (11). Though the effect of the compounds represented by Formula (11) (preferably represented by Formula (11a)) on enhancing the Re and the Rth is lower than those of compounds represented by Formulae (6) to (10), such compounds are preferably used in application that needs relatively low Re and Rth.

[Chem. 83]

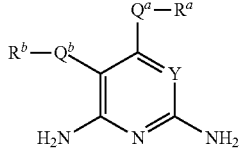

Formula (11)

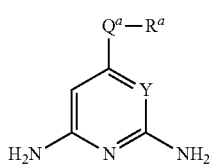

Formula (11a)

Symbols in Formulae are each synonymous with those in Formula (2), and the preferred ranges and preferred examples are also the same. Examples of the compound represented by Formula (11) or (11a) include compounds of which -$Q^a$-$R^a$ is a group other than —OH and —SH.

The compounds represented by Formula (12) also have high retardation-enhancing effects as in the compounds represented by Formulae (6), (7-1), (7-2), and (8) to (10).

[Chem. 84]

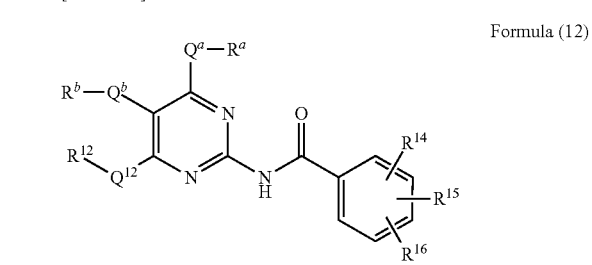

Formula (12)

The groups in the formula are each synonymous with those in Formulae (1) to (6), (7-1), (7-2), and (8) to (10), and the preferred ranges are also the same. $Q^{12}$ is a single bond or —NH—, —O—, or —S—; and $R^{12}$ is a hydrogen atom, an alkyl group having 1 to 8 carbon atoms, an aryl group having 6 to 18 carbon atoms (e.g., a benzene ring or naphthalene ring group), or a heterocyclic group having 4 to 10 carbon atoms (e.g., a pyrrolyl group, a pyrrolidino group, a pyrazolyl group, a pyrazolidino group, an imidazolyl group, a piperazino group, or a morpholino group), preferably an alkyl group having 1 to 8 carbon atoms or an aryl group having 6 to 18 carbon atoms. When $Q^{12}$ is a single bond or —O— or —S—, $R^{12}$ is preferably a hydrogen atom or an alkyl group having 1 to 8 carbon atoms; and when $Q^{12}$ is —NH—, $R^{12}$ is preferably an alkyl group having 1 to 8 carbon atoms and more preferably an aryl group having 6 to 18 carbon atoms (more preferably a benzene ring group). Examples of the compound represented by Formula (12) include compounds of which -$Q^a$-$R^a$ is a group other than —OH and —SH, provided that compounds where only one of -$Q^{12}$-$R^{12}$ and -$Q^a$-$R^a$— is —NH$_2$ are excluded.

The compound of the present invention is characterized by a pyrimidine ring or a pyridine ring having a prescribed substituent at a prescribed position thereon. Among the compounds of the present invention, compounds represented by partial structure Formula (A) have particularly high effects of reducing the dependency of Re and Rth on humidity. Such compounds are more preferably represented by partial structure Formula (B) and most preferably by partial structure Formula (C). Y in Formulae (A) to (C) is synonymous with Y in Formula (1), in other words, Y is —N— or —C(-$Q^d$-$R^d$)— (definitions of $Q^d$ and $R^d$ are as described above).

[Chem. 85]

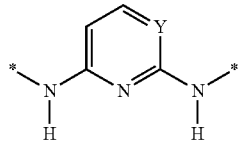

Partial structure (A)

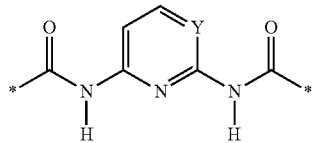

Partial structure (B)

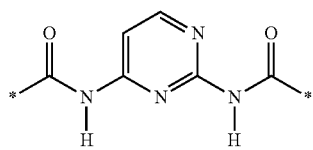

Partial structure (C)

These partial structures are characterized in that a hydrogen-bond donor site and a hydrogen-bond acceptor site are located sterically close to each other. Such a structure allows formation of hydrogen bonds with water or hydroxyl groups at multiple points. In particular, compounds having partial structure (B) or (C) can have a conformation capable of forming a circular hydrogen-bond pair with water or a hydroxyl group. These structural characteristics are likely to cause capture of water molecules in a polymer film or cause strong interaction with hydroxyl groups in a polymer or water bonded to a polymer through a hydrogen bond and thereby to express the effect of reducing the fluctuation in Re and Rth caused by a change in humidity of the operating environment.

The steric structure of the compound represented by Formula (1) used in the present invention is also important.

In order to express the effect of enhancing the retardation (Re and/or Rth) of a polymer film, a compound having high flatness and a rod structure is preferred. In order to express the effect of reducing the fluctuation in Re and Rth caused by a change in humidity of the operating environment of a polymer film, similarly, a compound having high flatness and a compact structure is preferred. If the compound is sterically bulky, the inventive compound is prevented by the polymer chain from approaching to effectively capture water molecules.

Specific examples of the usable compound represented by Formula (1) of the present invention are shown, but not limited to, below.

[Chem. 86]

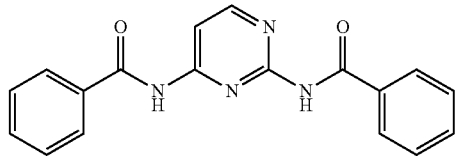

Chem. 1-1

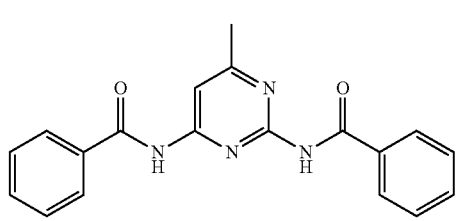

Chem. 1-2

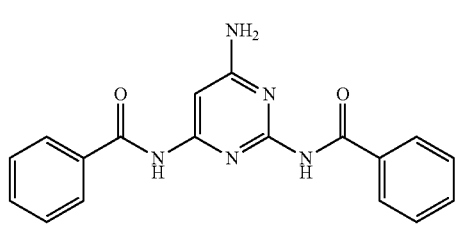

Chem. 1-3

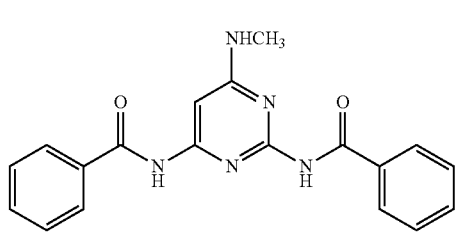

Chem. 1-4

Chem. 1-5
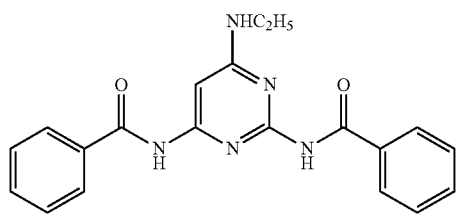
Chem. 1-6
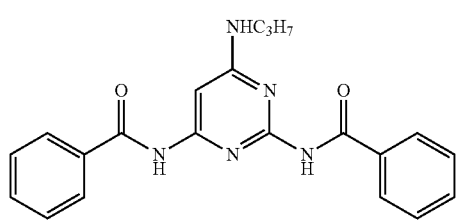
Chem. 1-7
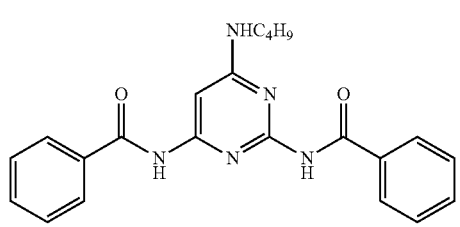
Chem. 1-8
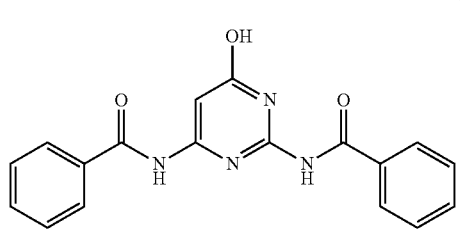
Chem. 1-9
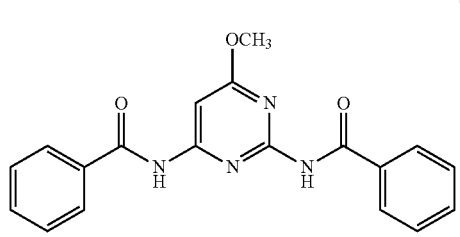
Chem. 1-10
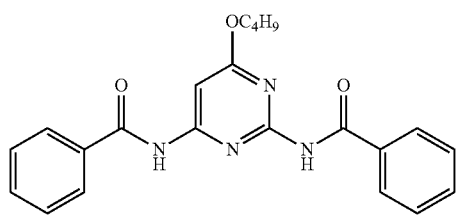
Chem. 1-11
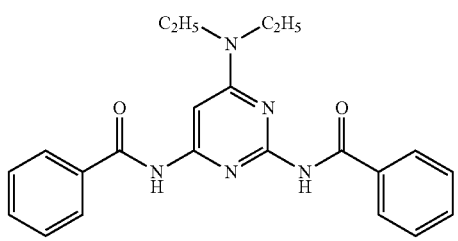
Chem. 1-12
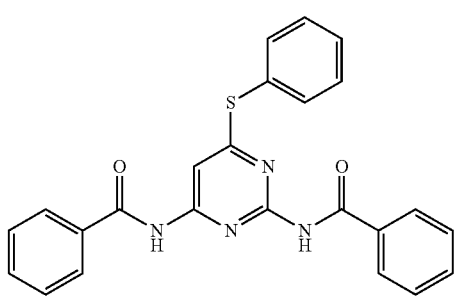
Chem. 1-13
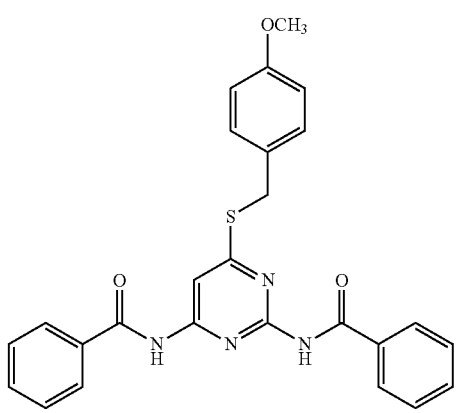
[Chem. 87]
Chem. 2-1
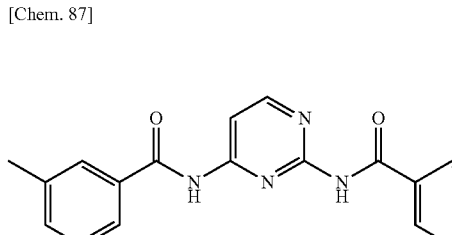
Chem. 2-2
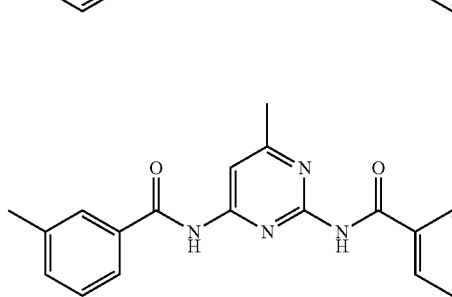

Chem. 2-3
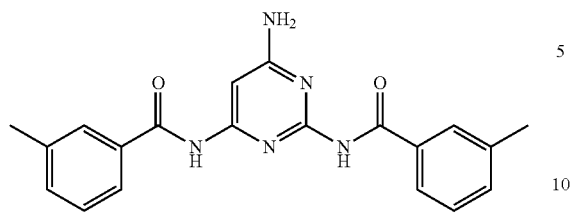
Chem. 2-4
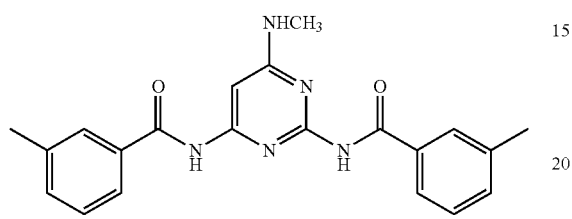
Chem. 2-5
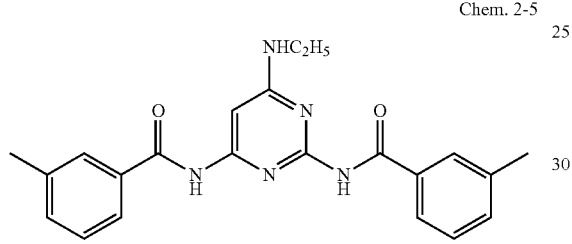
Chem. 2-6
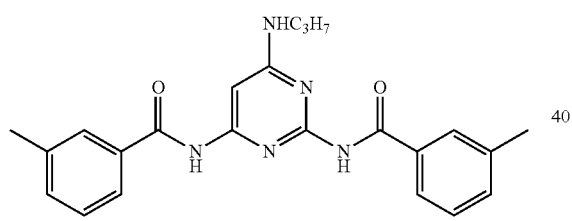
Chem. 2-7
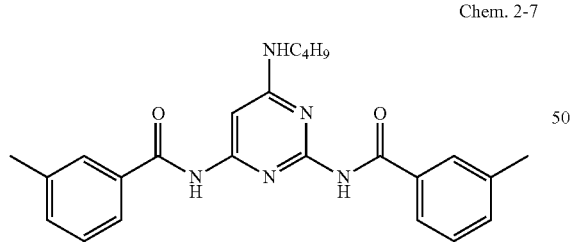
Chem. 2-8
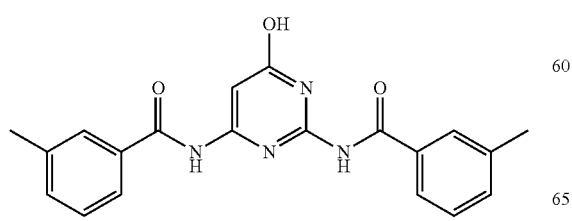
Chem. 2-9
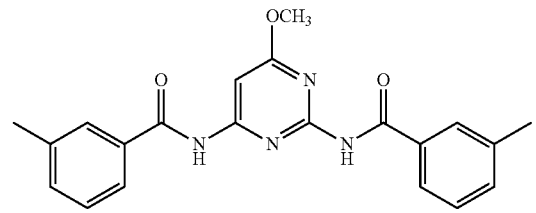
Chem. 2-10
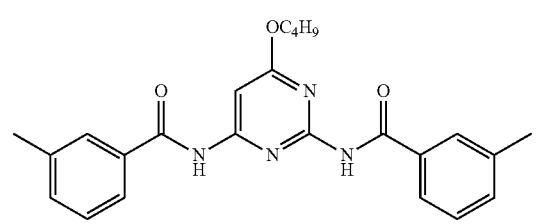
Chem. 2-11
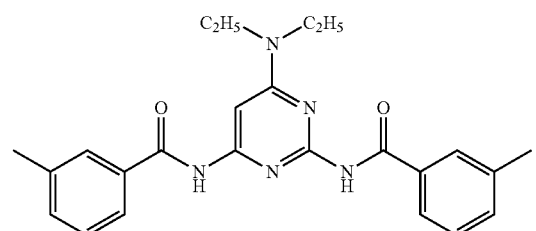
Chem. 2-12
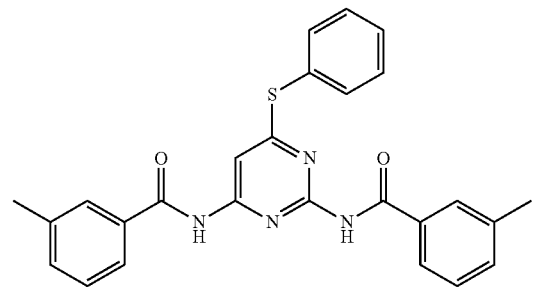
Chem. 2-13
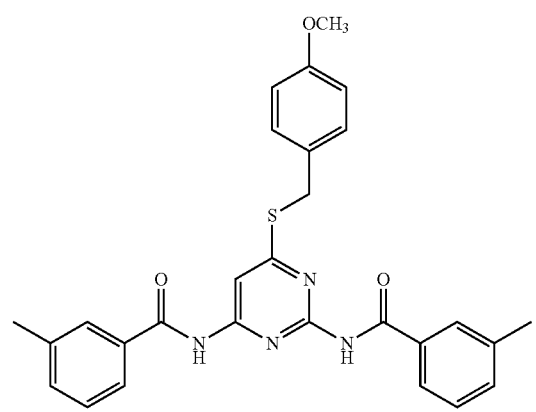

[Chem. 88]

Chem. 3-1 through Chem. 3-11, and Chem. 4-1: chemical structures.

[Chem. 89]

-continued
Chem. 4-2
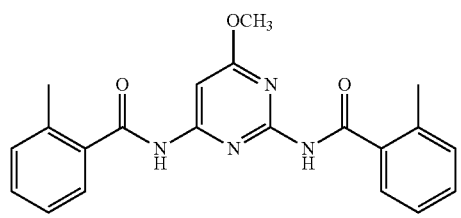
Chem. 4-3
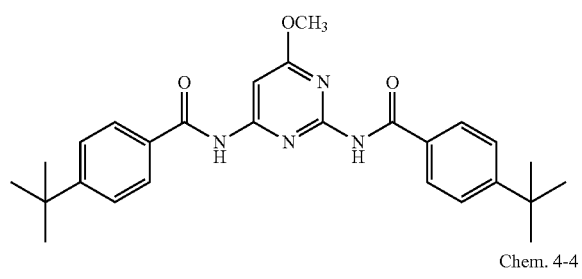
Chem. 4-4
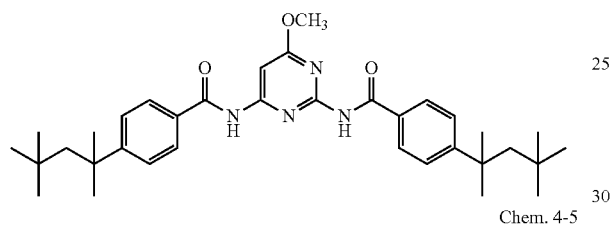
Chem. 4-5
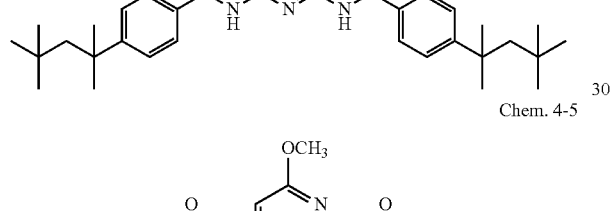
Chem. 4-6
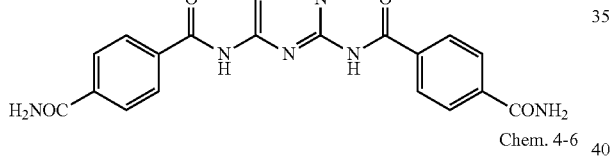
Chem. 4-7
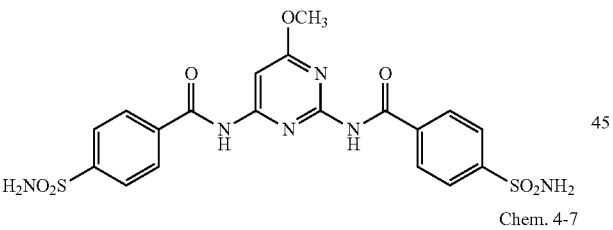
Chem. 4-8
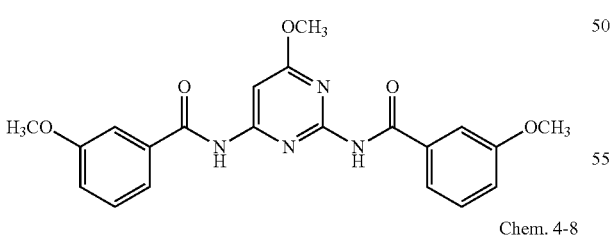
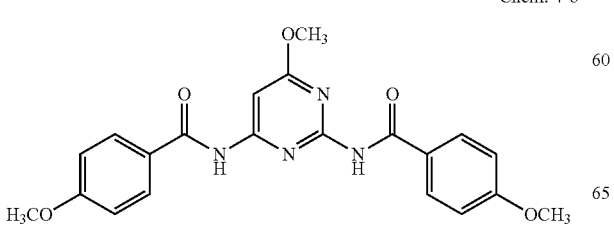
-continued
Chem. 4-9
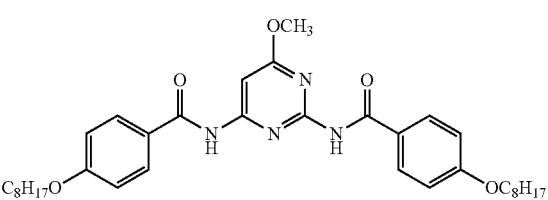
[Chem. 90]
Chem. 4-10
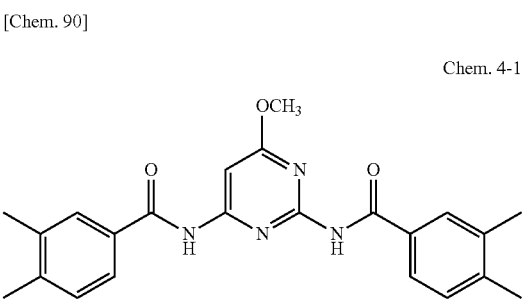
Chem. 4-11
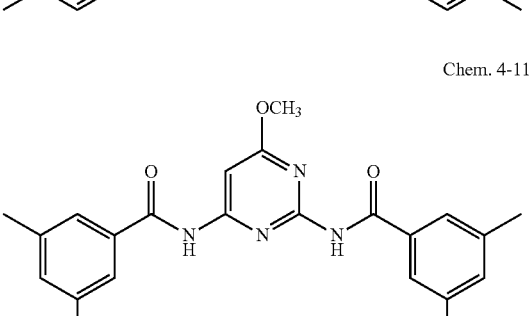
Chem. 4-12
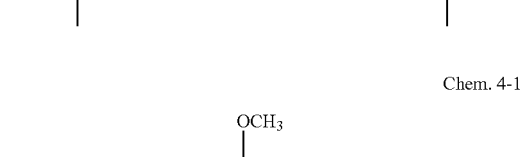
Chem. 4-13
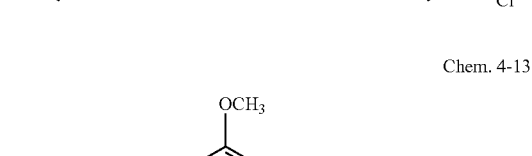
Chem. 4-14
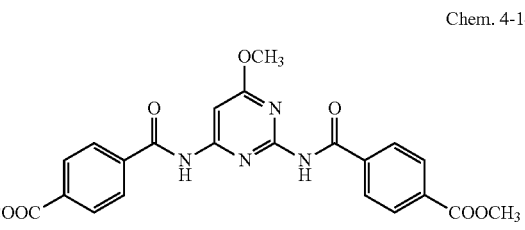

Chem. 4-15
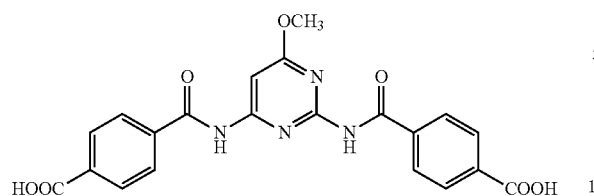
[Chem. 91]
Chem. 5-1
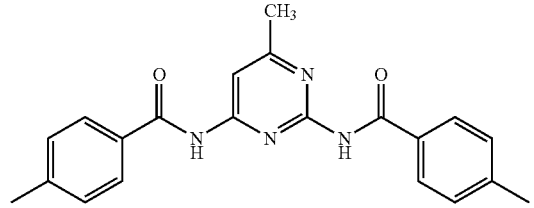
Chem. 5-2
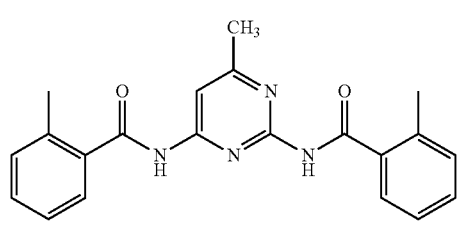
Chem. 5-3
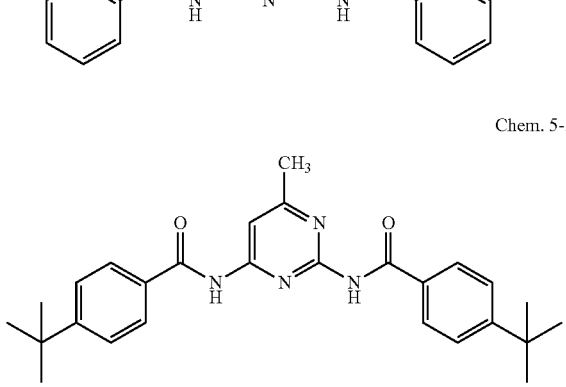
Chem. 5-4
Chem. 5-5
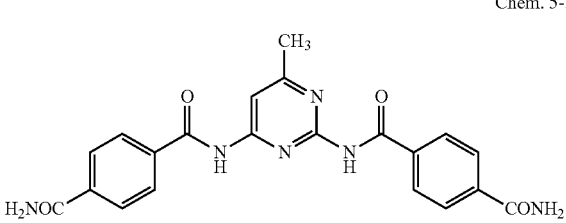
Chem. 5-6
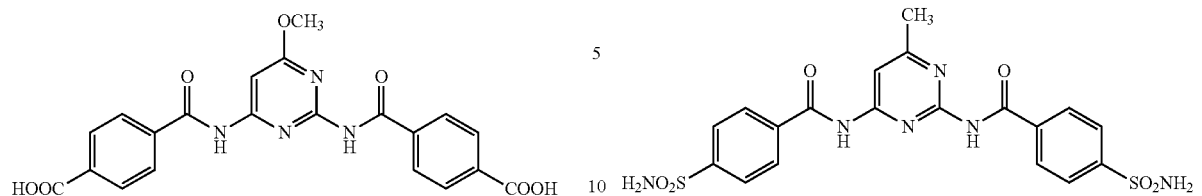
Chem. 5-7
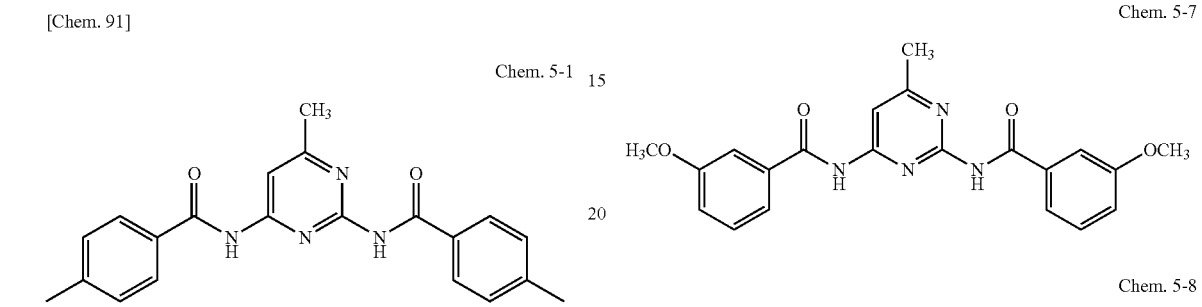
Chem. 5-8
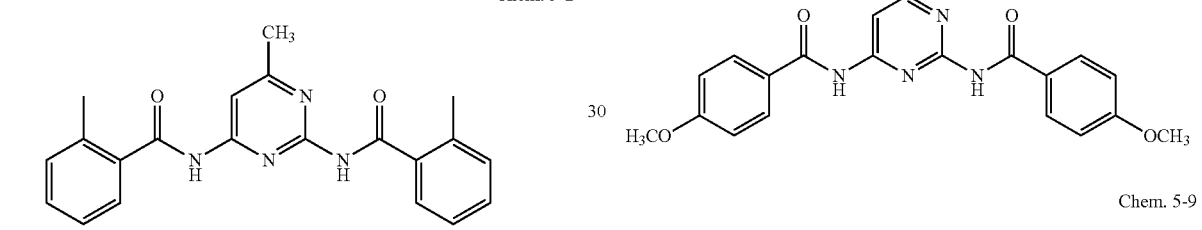
Chem. 5-9
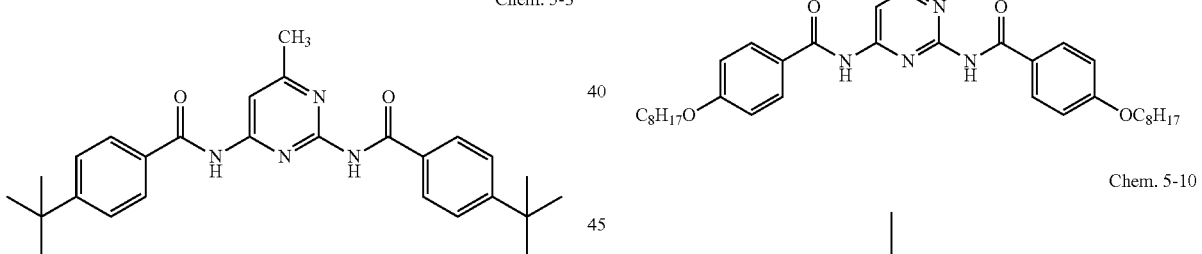
Chem. 5-10
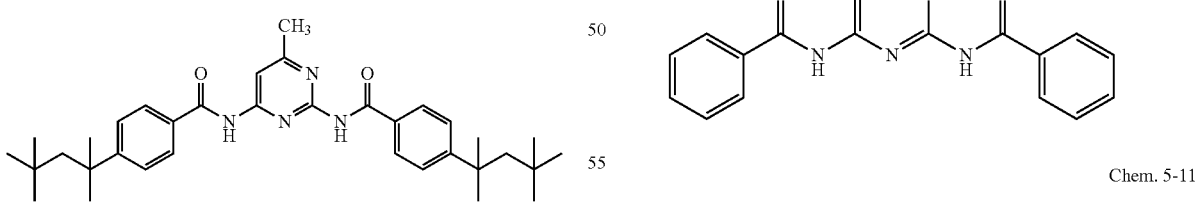
Chem. 5-11
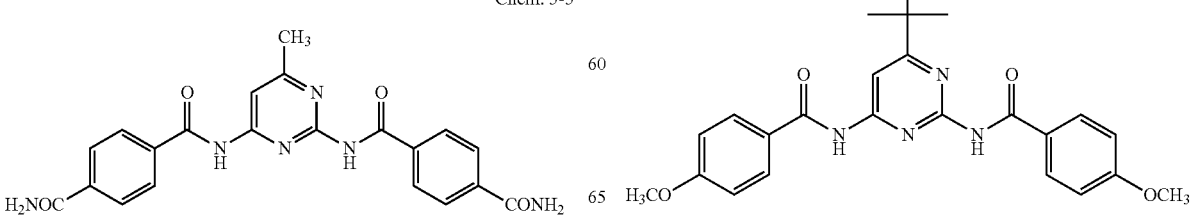

-continued
[Chem. 92]
Chem. 6-1
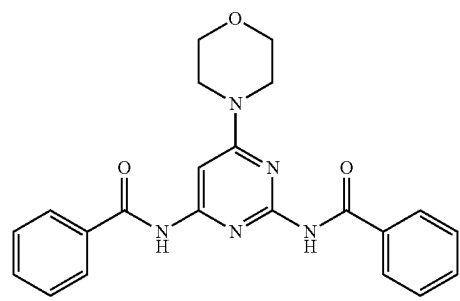
Chem. 6-2
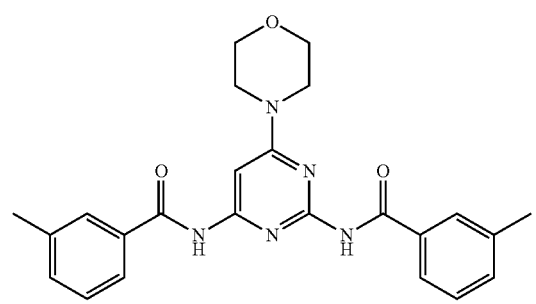
Chem. 6-3
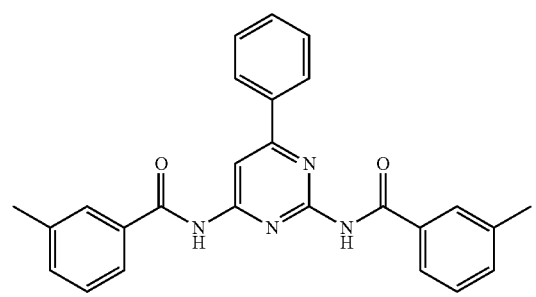
Chem. 6-4
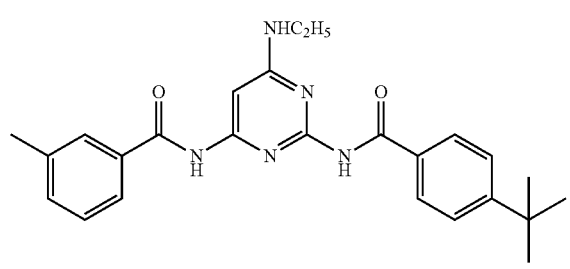
Chem. 6-5
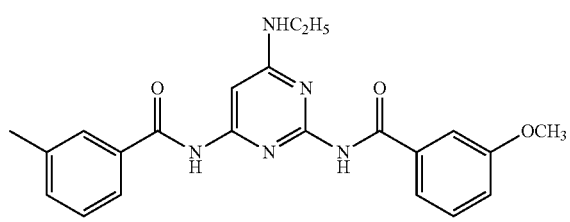
-continued
Chem. 6-6
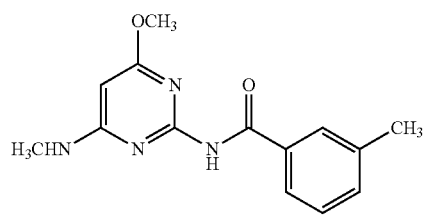
Chem. 6-7
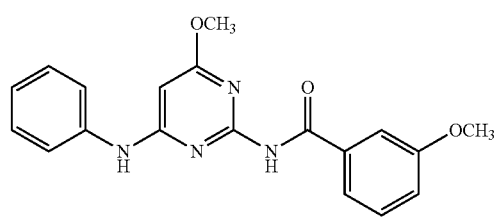
Chem. 6-8
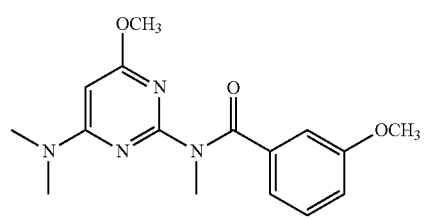
Chem. 6-9
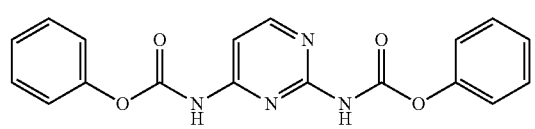
Chem. 6-10
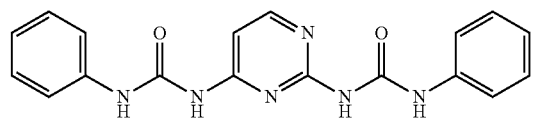
Chem. 6-11
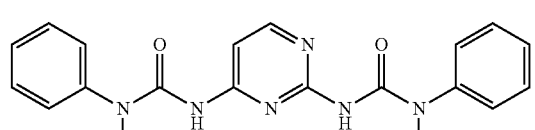
Chem. 6-12
[Chem. 93]
Chem. 6-13
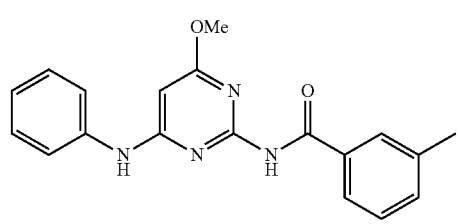

Chem. 6-14
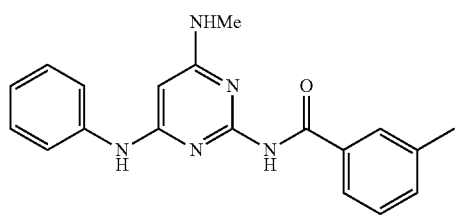
Chem. 6-15
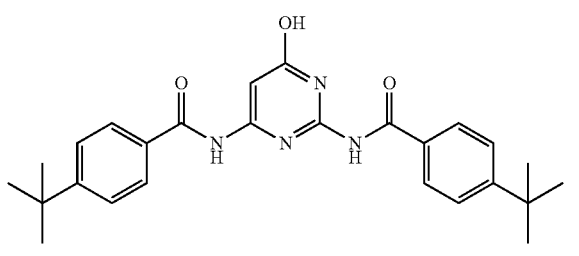
Chem. 6-16
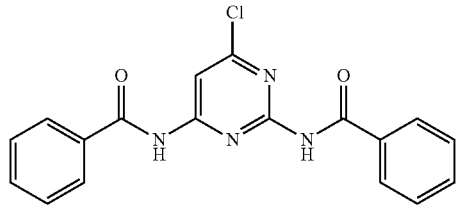
Chem. 6-17
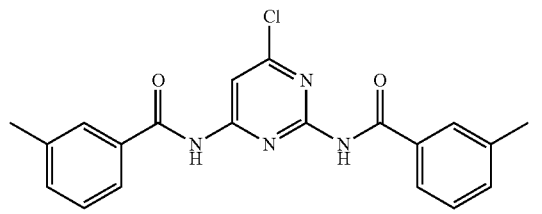
[Chem. 94]
Chem. 6-18
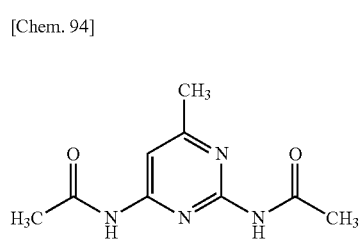
Chem. 6-19
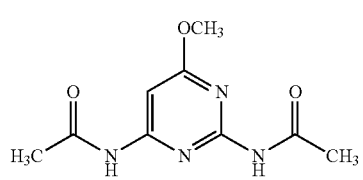
Chem. 6-20
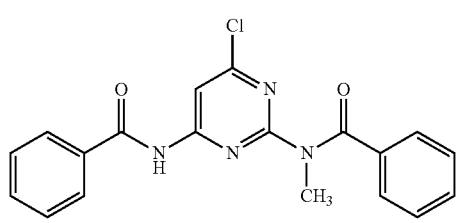
Chem. 6-21
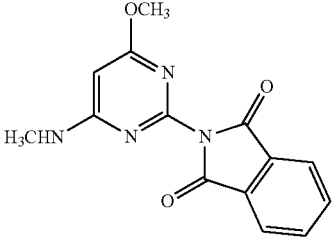
Chem. 6-22
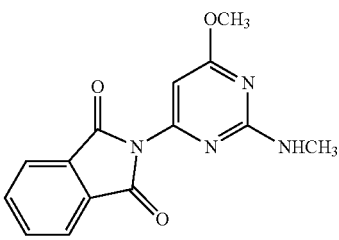
Chem. 6-23
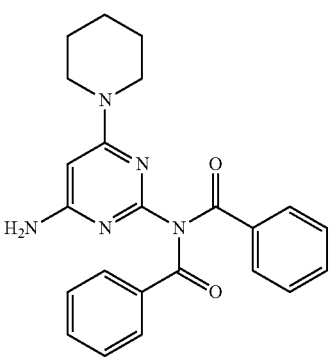
Chem. 6-24
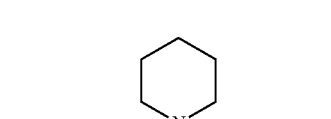
[Chem. 95]
Chem. 7-1
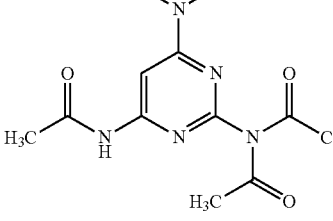
Chem. 7-2

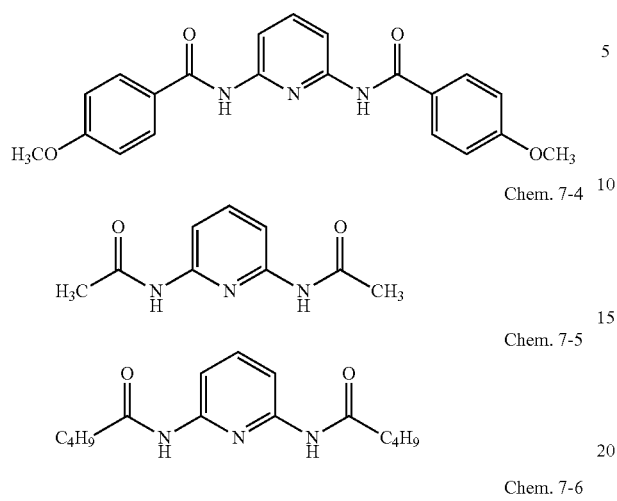

Chem. 8-7
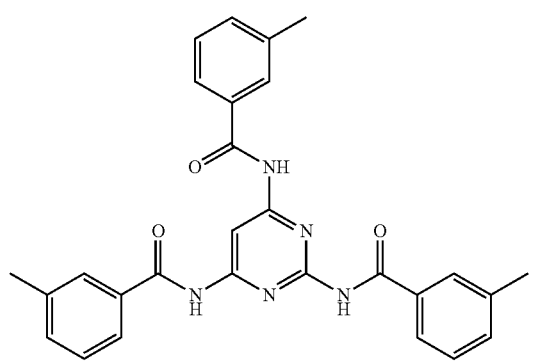
[Chem. 97]
Chem. 9-1
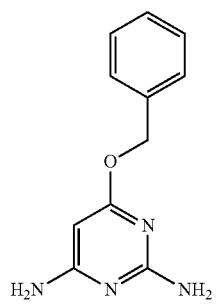
Chem. 9-2
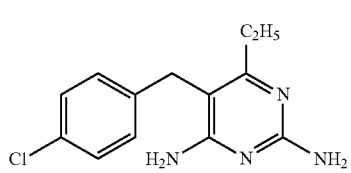
Chem. 9-3
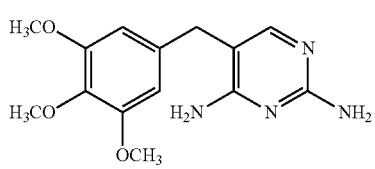
Chem. 9-4
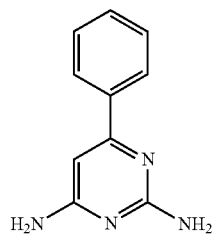
Chem. 9-5
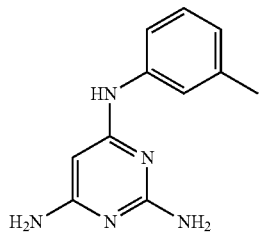
Chem. 9-6
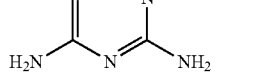
Chem. 9-7
Chem. 9-8
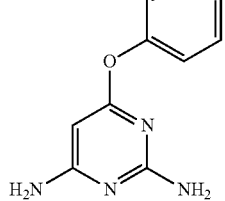
Chem. 9-9
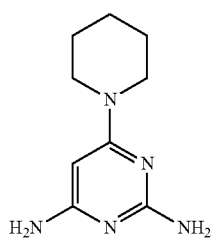
[Chem. 98]
Chem. 9-10
Chem. 9-11
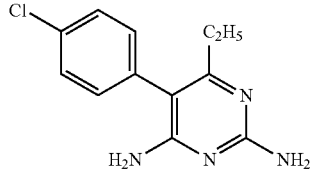

Chem. 9-12
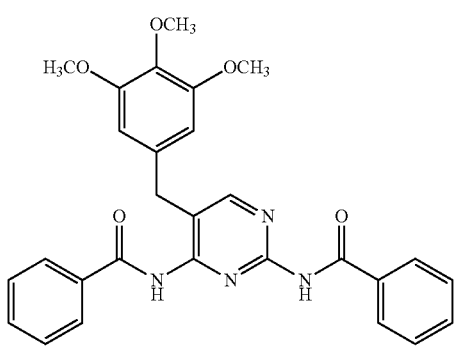
Chem. 9-15
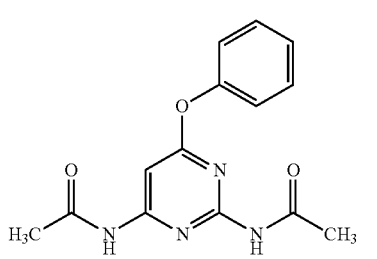
Chem. 9-16
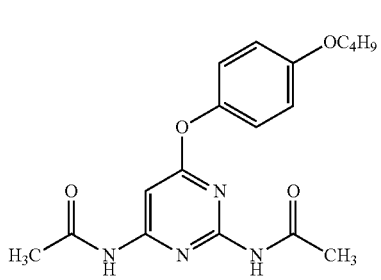
Chem. 9-13
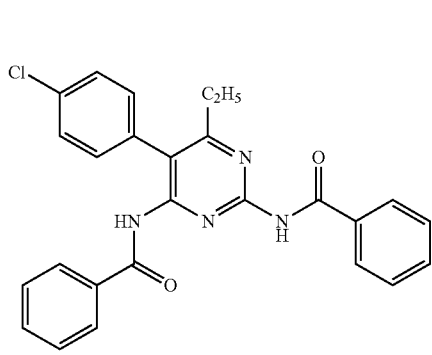
Chem. 9-14
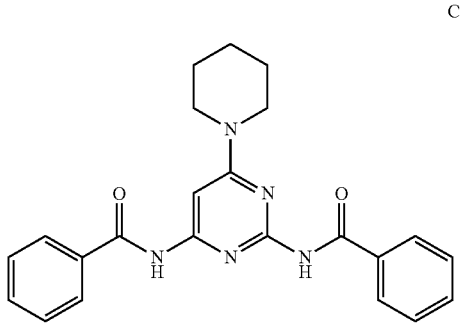
Chem. 9-17
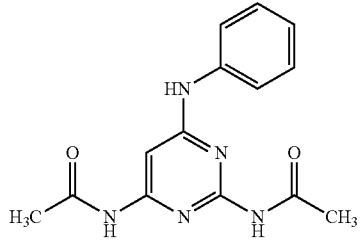
Chem. 9-18
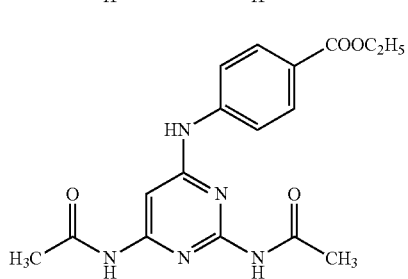
[Chem. 99]
Chem. 9-19
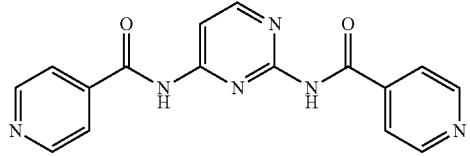
Chem. 9-20
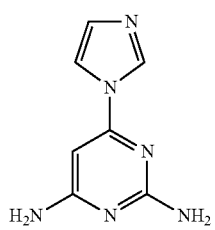
Chem. 9-21
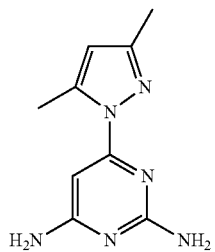
Chem. 9-22
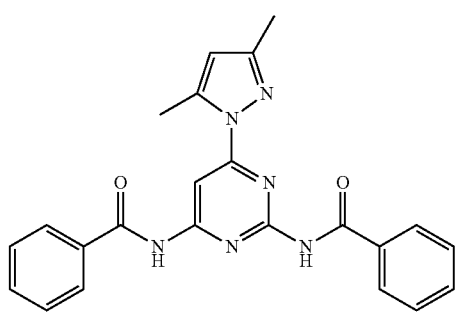

-continued
[Chem. 100]
Chem. 10-1
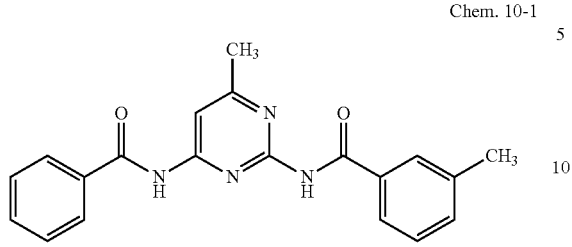
Chem. 10-2
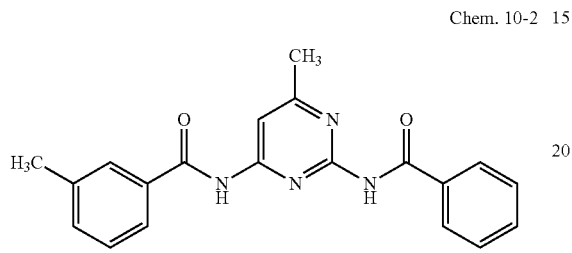
Chem. 10-3
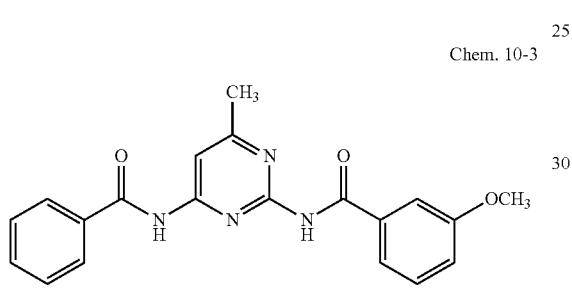
Chem. 10-4
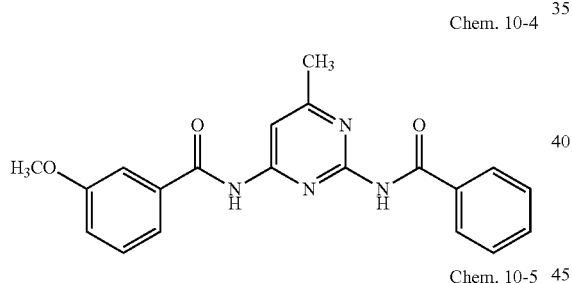
Chem. 10-5
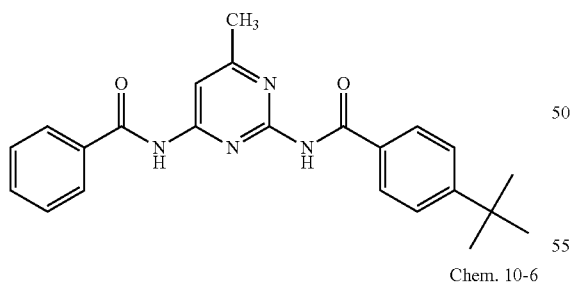
Chem. 10-6
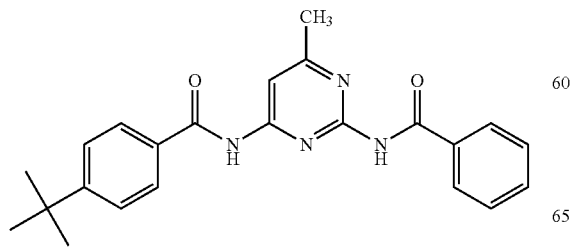
-continued
Chem. 10-7
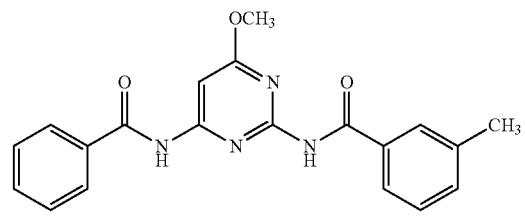
Chem. 10-8
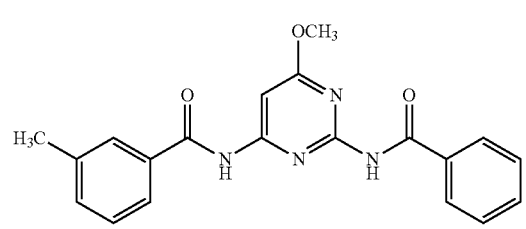
Chem. 10-9
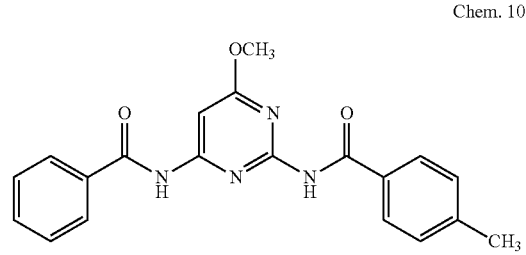
Chem. 10-10
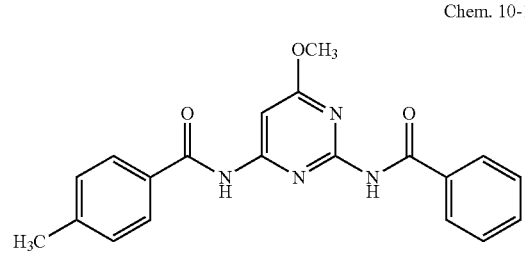
Chem. 10-11
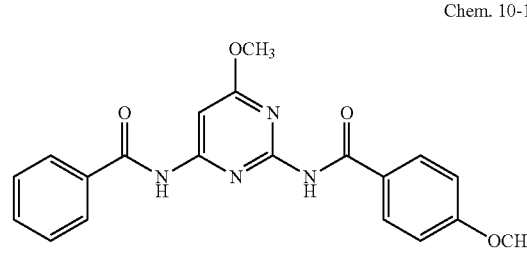
Chem. 10-12
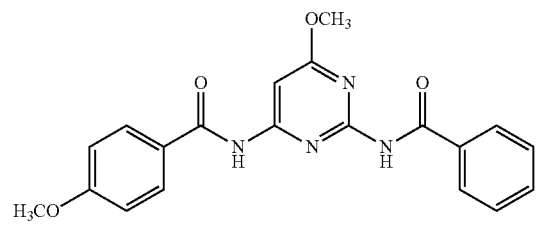

[Chem. 101]
Chem. 10-13
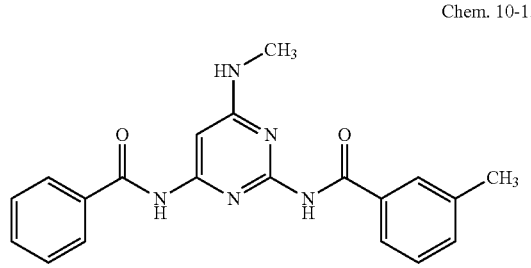
Chem. 10-14
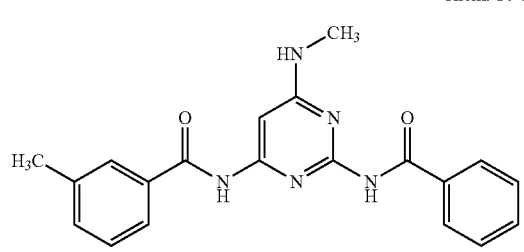
Chem. 10-15
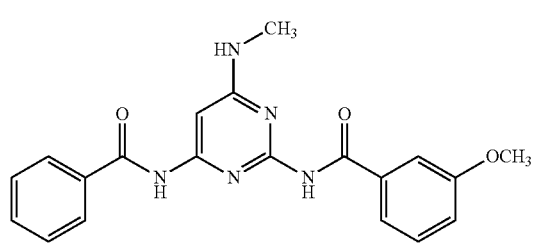
Chem. 10-16
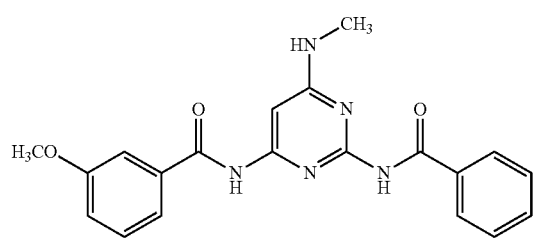
Chem. 10-17
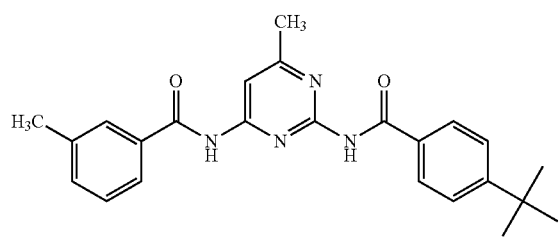
Chem. 10-18
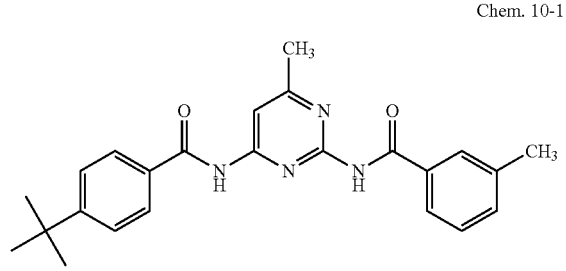
Chem. 10-19
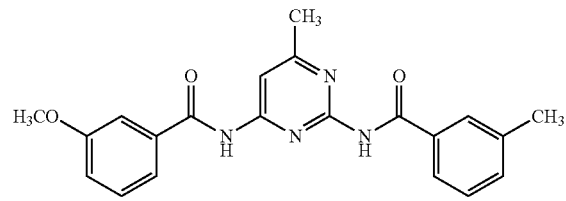
Chem. 10-20
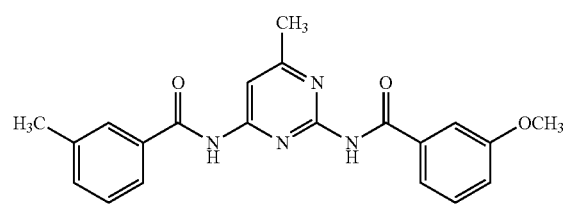
Chem. 10-21
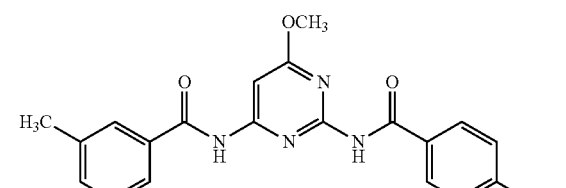
Chem. 10-22
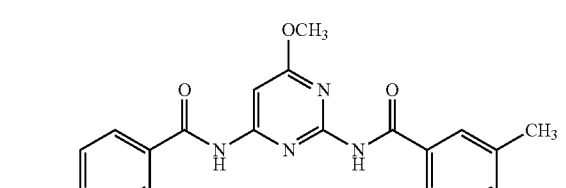
Chem. 10-23
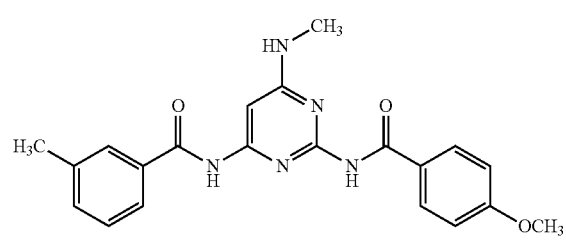
Chem. 10-24
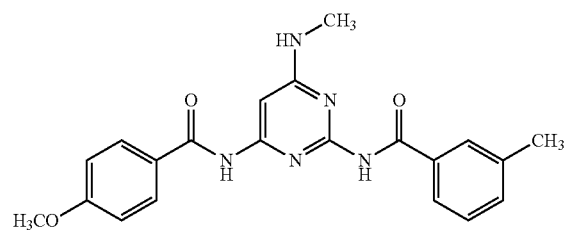
(1b-1) The Compound Group B
The compound group B is represented by Formula (I) and is preferably represented by Formula (II).

[Chem. 102]

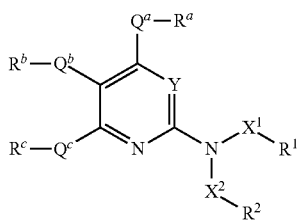

Formula (I)

In Formula (I), Y represents —N— or —C(-$Q^d$-$R^d$)—; $Q^a$, $Q^b$, $Q^c$, and $Q^d$ each independently represent a single bond or a divalent linking group; $R^a$, $R^b$, $R^c$, and $R^d$ each independently represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring; $X^2$ represents a single bond or a divalent linking group; $X^1$ represents a single bond or a divalent group selected from the divalent linking group $G^1$ shown below; and $R^1$ and $R^2$ each independently represent a hydrogen atom, an alkyl group, an alkenyl group, an alkynyl group, an aryl group, or a heterocyclic group, wherein $R^1$ and $R^2$ are optionally bonded to each other to form a ring, provided that one of -$Q^c$-$R^c$ and N($X^1R^1$)$X^2R^2$ is —$NH_2$ and both are not simultaneously —$NH_2$ and that when Y is a nitrogen atom and when N($X^1R^1$)$X^2R^2$ is —$NH_2$, -$Q^a$-$R^a$ is not —$NH_2$. That is, compounds not having amine and diamine compounds having partial structures shown below are excluded from the compounds represented by Formula (I).

[Chem. 103]

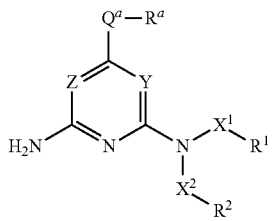

In the formulae, each symbol * denotes a position to which any one of -$Q^a$-$R^a$, -$Q^b$-$R^b$, -$Q^c$-$R^c$, and -$Q^d$-$R^d$ bonds.

[Chem. 104]

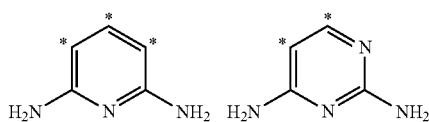

Formula (II)

Symbols in Formula (II) are each synonymous with those in Formula (I); Y represents —N— or —C(-$Q^d$-$R^d$)—, and Z represents —N— or —C(-$Q^b$-$R^b$)—, provided that Y and Z are not simultaneously —N—; $X^1$ represents a single bond or a linking group selected from the group consisting of divalent linking groups represented by the divalent linking group $G^2$; $X^2$ represents a single bond or a divalent linking group; $R^1$ and $R^2$ each independently represent a hydrogen atom, an alkyl group, an alkenyl group, an alkynyl group, an aryl group, or a heterocycle; at least one of —$X^1$—$R^1$ and —$X^2$—$R^2$ is a substituent other than a hydrogen atom; $Q^a$, $Q^b$, and $Q^d$ each independently represent a single bond or —O—, —S—, or —NR'—, wherein R' represents a hydrogen atom, an alkyl group, an alkenyl group, an alkynyl group, an aryl group, or a heterocycle, wherein $Q^a$ and $R^a$, $Q^d$ and $R^d$, or $Q^b$ and $R^b$ are optionally bonded to each other to form a ring, or -$Q^a$-$R^a$—$R^d$-$Q^d$- or -$Q^a$-$R^a$—$R^b$-$Q^b$- optionally forms a ring; and $R^a$ represents a hydrogen atom, a halogen, an alkyl group, an alkenyl group, an alkynyl group, an aryl group, or a heterocycle, provided that when Z is —N—, -$Q^a$-$R^a$ represents a substituent other than an amino group; $R^b$ and $R^d$ each independently represent a hydrogen atom, an alkyl group, an alkenyl group, an alkynyl group, an aryl group, or a heterocycle.

In Formula (I), when Y is a methine group, in other words, when Y is —C(-$Q^d$-$R^d$)—, the 6-membered ring in the formula is a pyridine ring; and when Y is —N—, the 6-membered ring in the formula is a pyrimidine ring. In Formula (I), when Y is —N— and when —N($X^1R^1$)$X^2R^2$ is —$NH_2$, -$Q^a$-$R^a$ is not —$NH_2$.

In Formula (II), Y and Z are not simultaneously —N—, when Y and Z are methine groups optionally having substituents, in other words, when Y and Z are —C(-$Q^d$-$R^d$)— or —C(-$Q^b$-$R^b$)—, the 6-membered ring in the formula is a pyridine ring; and when Y or Z is —N—, the 6-membered ring in the formula is a pyrimidine ring. In Formula (II), when Z is —N—, -$Q^a$-$R^a$ is not —$NH_2$.

Examples of the compound represented by Formula (I) or (II) include compounds not having the partial structures represented by Formula (a) or (b). In Formulae (a) and (b), each symbol * indicates a position into which an atom or a residue can be introduced.

[Chem. 105]

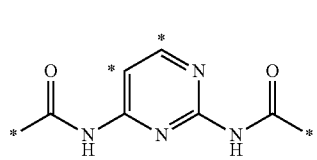

(a)

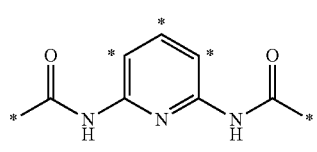

(b)

Examples of the structures of the compounds represented by Formula (I) and (II) are not limited to those specified by Formula (I) and (II) and include resonance structures of the heterocyclic skeletons specified by Formula (I) or (II). The examples of the structures of the compounds represented by Formula (I) and (II) also include structures in which the heterocyclic skeletons specified by Formula (I) and (II) resonate with substituents bonded to atoms constituting the rings. The same applies to the compounds represented by formulae described below.

In Formulae (I) and (II), examples of the divalent linking group represented by $Q^a$, $Q^b$, $Q^c$, or $Q^d$ include divalent linking groups represented by —O—, —S—, —N($X^a$—$R^h$)—, or —N($X^a$—$R^h$)—$X^b$—, wherein $X^a$ and $X^b$ each represent a single bond or a divalent linking group. Examples of the divalent linking group represented by $X^a$ or $X^b$ include —CO—, —COO—, and —CONH—. $R^h$ represents a hydrogen atom, an alkyl group having 1 to 8 carbon atoms, an alkenyl group having 2 to 8 carbon atoms, an alkynyl group having 2 to 8 carbon atoms, an aryl group having 6 to 10 carbon atoms, or a heterocyclic group having 2 to 10 carbon atoms. Preferred examples of the divalent linking group represented by $Q^a$, $Q^b$, $Q^c$, or $Q^d$ include a single bond, —O—, —N($X^a$—$R^h$)—, and —N($X^a$—$R^h$)—$X^b$—; and a single bond, —O—, —NH—, and —NH—$X^b$— are particularly preferred. Preferred examples of —NH—$X^b$— include —NH—CO—, —NH—COO—, —NH—CONH—, and —NH—$SO_2$—; and —NH—CO— and —NH—COO— are particularly preferred.

In Formulae (I) and (II), $R^a$, $R^b$, $R^c$, and $R^d$ each represent a hydrogen atom, an alkyl group, an alkenyl group, an alkynyl group, an aryl group, a cyano group, a halogen group, or a heterocyclic group, wherein $R^a$ and $R^b$ are optionally bonded to each other to form a ring, or $R^a$ and $R^d$ are optionally bonded to each other to form a ring.

When $R^a$, $R^b$, $R^c$, or $R^d$ represents the alkyl group, the alkyl group preferably has 1 to 20 carbon atoms, more preferably 1 to 8 carbon atoms, and most preferably 1 to 4 carbon atoms. When $R^a$, $R^b$, $R^c$, or $R^d$ represents the alkyl group, one carbon atom or non-adjacent two or more carbon atoms are each optionally replaced by a hetero atom selected from oxygen atom, sulfur atom, and nitrogen atom (including —NH— and —N(R)— (R: alkyl group)). For example, $R^a$ and $R^b$ may each be an alkylene (e.g., ethylene or propylene) oxy group.

When $R^a$, $R^b$, $R^c$, or $R^d$ represents the alkenyl group, the alkenyl group preferably has 2 to 20 carbon atoms, more preferably 2 to 8 carbon atoms, and most preferably 2 to 4 carbon atoms.

When $R^a$, $R^b$, $R^c$, or $R^d$ represents the alkynyl group, the alkynyl group preferably has 2 to 20 carbon atoms, more preferably 2 to 8 carbon atoms, and most preferably 2 to 4 carbon atoms.

When $R^a$, $R^b$, $R^c$, or $R^d$ represents the aryl group, the aryl group preferably has 6 to 24 carbon atoms, more preferably 6 to 18 carbon atoms, and most preferably 6 to 10 carbon atoms, from the viewpoint of reducing humidity dependency. Specifically, the aryl group is preferably a benzene ring or a naphthalene ring and most preferably a benzene ring.

When $R^a$, $R^b$, $R^c$, and $R^d$ are each a halogen group, any of fluorine atom, chlorine atom, bromine atom, and iodine atom can be used, and chlorine atom are particularly preferred.

When $R^a$, $R^b$, $R^c$, or $R^d$ represents the heterocyclic group, the heterocyclic group preferably has 4 to 20 carbon atoms, more preferably 4 to 10 carbon atoms, and most preferably 4 to 6 carbon atoms, from the viewpoint of reducing humidity dependency. Specific examples of the heterocyclic group include pyrrolyl group, pyrrolidino group, pyrazolyl group, pyrazolidino group, imidazolyl group, piperazino group, and morpholino group.

$R^a$ and $R^b$ are optionally bonded to each other to form a ring, $R^a$ and $R^d$ are optionally bonded to each other to form a ring. The ring to be formed may be a hydrocarbon ring or a heterocycle and is preferably a 5-membered or 6-membered ring.

$R^a$, $R^b$, $R^c$, and $R^d$ each optionally further have one or more substituents, if possible. Examples of the substituent optionally possessed by $R^a$, $R^b$, $R^c$, or $R^d$ include those shown in the substituent group T mentioned above.

In Formula (I), $R^a$, $R^b$, $R^c$, and $R^d$ are each preferably a hydrogen atom, a halogen atom, or a substituted or unsubstituted alkyl group. In Formula (II), $R^c$ is preferably a hydrogen atom. In one embodiment of compounds belonging to the compound group B, $R^d$ should preferably be a hydrogen atom and $Q^d$ be a single bond, in other words, —C(-$Q^d$-$R^d$)— represented by Y is unsubstituted methine. In one embodiment of the present invention, $R^b$ should preferably be a hydrogen atom and $Q^b$ be a single bond, in other words, —C(-$Q^b$-$R^b$)— represented by Y is unsubstituted methine.

Examples of the compound represented by Formula (I) or (II) includes compounds in which Y is a nitrogen atom and -$Q^a$-$R^a$ and -$Q^c$-$R^c$ are each a group other than —OH and —SH.

In Formulae (I) and (II), -$Q^a$-$R^a$ is preferably -$Q^{aa}$-$R^{aa}$. $Q^{aa}$ represents a single bond or —O—, —NH—, or —N(R)— (wherein R is an alkyl group having 1 to 8 carbon atoms). $R^{aa}$ represents a hydrogen atom, a halogen atom, or an alkyl group having 1 to 8 carbon atoms.

In Formulae (I) and (II), $R^1$ and $R^2$ each represent a hydrogen atom, an alkyl group, an alkenyl group, an alkynyl group, an aryl group, or a heterocyclic group, wherein $R^1$ and $R^2$ are optionally bonded to each other to form a ring.

When $R^1$ or $R^2$ each represents the alkyl group, the alkyl group preferably has 1 to 20 carbon atoms, more preferably 1 to 8 carbon atoms, and most preferably 1 to 4 carbon atoms. When $R^1$ or $R^2$ each represents the alkyl group, one carbon atom or non-adjacent two or more carbon atoms are each optionally replaced by a hetero atom selected from oxygen atom, sulfur atom, and nitrogen atom (including —NH— and —N(R)— (R: alkyl group)). For example, $R^1$ and $R^2$ may each be an alkylene (e.g., ethylene or propylene) oxy group.

When $R^1$ or $R^2$ each represents the alkenyl group, the alkenyl group preferably has 2 to 20 carbon atoms, more preferably 2 to 8 carbon atoms, and most preferably 2 to 4 carbon atoms.

When $R^1$ or $R^2$ each represents the alkynyl group, the alkynyl group preferably has 2 to 20 carbon atoms, more preferably 2 to 8 carbon atoms, and most preferably 2 to 4 carbon atoms.

When $R^1$ or $R^2$ each represents the aryl group, the aryl group preferably has 6 to 24 carbon atoms, more preferably 6 to 18 carbon atoms, and most preferably 6 to 10 carbon atoms, from the viewpoint of reducing humidity dependency. Specifically, the aryl group is preferably a benzene ring or a naphthalene ring and most preferably a benzene ring.

When $R^1$ or $R^2$ each represents the heterocyclic group, the heterocyclic group preferably has 4 to 20 carbon atoms, more preferably 4 to 10 carbon atoms, and most preferably 4 to 6 carbon atoms, from the viewpoint of reducing humidity dependency. Specific examples of the heterocyclic group include pyrrolyl group, pyrrolidino group, pyrazolyl group, pyrazolidino group, imidazolyl group, piperazino group, and morpholino group.

In Formulae (I) and (II), $R^1$ and $R^2$ are each preferably a hydrogen atom, an alkyl group, an aryl group, or a heterocyclic group, provided that when -$Q^c$-$R^c$ is —$NH_2$ and when —$X^1$ and —$X^2$ represent single bonds, at least one of $R^1$ and $R^2$ is not a hydrogen atom.

$R^1$ and $R^2$ each optionally further have one or more substituents, if possible. Examples of the substituent optionally possessed by $R^1$ or $R^2$ include those shown in the substituent group T mentioned above.

In Formulae (I) and (II), $R^1$ and $R^2$ are each preferably a hydrogen atom, a substituted or unsubstituted alkyl group, a substituted or unsubstituted aryl group, or a substituted or unsubstituted heterocyclic group.

One of $R^1$ and $R^2$ is preferably a hydrogen atom or a substituted or unsubstituted alkyl group and more preferably a hydrogen atom. From the viewpoint of reducing humidity dependency, the other is preferably a substituted or unsubstituted aryl group.

In Formulae (I) and (II), $X^2$ represents a single bond or a divalent linking group; and $X^1$ represents a single bond or a group selected from the divalent linking group $G^1$ shown below.

Examples of the divalent linking group represented by $X^2$ include alkylene groups (preferably having 1 to 30 carbon atoms, more preferably 1 to 3 carbon atoms, and most preferably 2 carbon atoms) and arylene groups (preferably having 6 to 30 carbon atoms and more preferably 6 to 10 carbon atoms); and examples of the divalent linking group represented by $X^1$ include those belonging to the divalent linking group $G^1$ and preferably those belonging to the divalent linking group $G^2$.

[Chem. 106]

Divalent linking group $G^1$

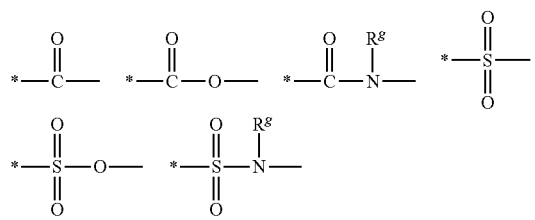

[Chem. 107]

Divalent linking group $G^2$

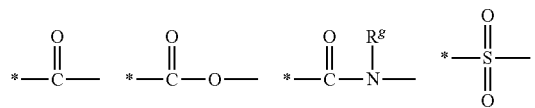

In each formula, the side indicated by symbol * is a bonding site to the nitrogen atom of the substituent introduced into the pyrimidine ring or pyridine ring in the compound represented by each formula; and $R^g$ represents a hydrogen atom, an alkyl group, an alkenyl group, an alkynyl group, an aryl group, or a heterocyclic group. The preferred range of the number of carbon atoms in each group is the same as the preferred range of the carbon atoms in the groups represented by $X^a$ and $X^b$.

$X^1$ is preferably a single bond or a group selected from the divalent linking group $G^1$. More preferably, $X^2$ is a single bond and $X^1$ represents a group selected from the divalent linking group $G^1$.

More preferably, in such a case, $X^1$ is any one of —CO—, —COO—, and —CO(NR$^g$)— and most preferably —CO—.

For example, when $X^1$ is a prescribed divalent linking group (preferably —CO—) and when $X^2$ is a single bond, $R^1$ is a substituted or unsubstituted alkyl group, a substituted or unsubstituted aryl group, or a substituted or unsubstituted heterocyclic group (from the viewpoint of reducing humidity dependency, preferably a substituted or unsubstituted aryl group) and $R^2$ is preferably a hydrogen atom.

Furthermore, in Formula (I), when $X^1$ is a prescribed divalent linking group, $R^1$ is preferably an aryl group, in particular, a phenyl group. The aryl group optionally has one or more substituents selected from the substituent group T. The substituent may be introduced into any position and may be introduced into one of the ortho-, meta-, and para-positions relative to $X^1$. Preferred examples of the substituent include halogen atoms, a hydroxy group, a carbamoyl group, a sulfamoyl group, alkyl groups (preferably alkyl groups having 1 to 8 carbon atoms), alkoxy groups (preferably alkoxy groups having 1 to 8 carbon atoms), alkylamino groups (preferably alkylamino groups having 1 to 8 carbon atoms), and dialkylamino groups (preferably dialkylamino groups having 1 to 8 carbon atoms). Alkyl groups (preferably alkyl groups having 1 to 8 carbon atoms) and alkoxy groups (preferably alkoxy groups having 1 to 8 carbon atoms) are more preferred, and alkyl groups and alkoxy groups having 1 to 4 carbon atoms are most preferred.

Examples of the compound represented by Formula (II) include compounds represented by Formula (III).

[Chem. 108]

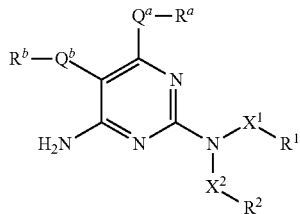

Formula (III)

Symbols in Formula (III) are each synonymous with those in Formula (II), and the preferred ranges and specific examples are also the same, provided that compounds having —NH$_2$ as —N(X$^1$R$^1$)X$^2$R$^2$ are excluded.

Preferred examples of the compound represented by Formula (III) include compounds represented by Formula (IIIa).

[Chem. 109]

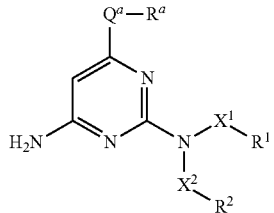

Formula (IIIa)

Symbols in Formula (IIIa) are each synonymous with those in Formula (II), and the preferred ranges are also the same, provided that compounds where —N(X$^1$R$^1$)X$^2$R$^2$ is —NH$_2$ are excluded.

Preferred examples of the compound represented by Formula (III) include compounds represented by Formula (IIIb).

[Chem. 110]

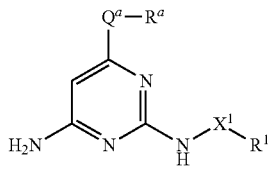

Formula (IIIb)

Symbols in Formula (IIIb) are each synonymous with those in Formula (II), and the preferred ranges are also the same, provided that compounds where —X$^1$R$^1$ is a hydrogen atom are excluded.

Preferred examples of the compound represented by Formula (III) include compounds represented by Formula (IIIc).

[Chem. 111]

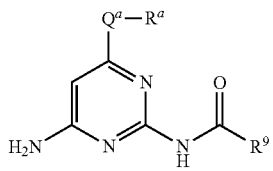

Formula (IIIc)

Symbols in Formula (IIIc) are each synonymous with those in Formula (II), and the preferred ranges are also the same. R$^9$ represents —O—Ar, an alkyl group, an alkenyl group, an alkynyl group, an aryl group, or a heterocyclic group, wherein Ar represents an aryl group. The aryl group optionally has one or more substituents.

The aryl group represented by Ar is preferably a substituted or unsubstituted phenyl or naphthyl group and more preferably a phenyl group. The aryl group represented by Ar optionally has one or more substituents. Examples of the substituent include those belonging to the substituent group T, and preferred examples of the substituent are the same as those possessed by R$^1$ or R$^3$ in Formula (II).

Preferred examples of the compound represented by Formula (III) include compounds represented by Formula (IIId).

[Chem. 112]

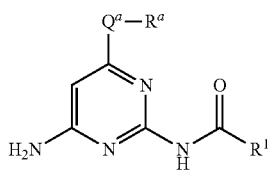

Formula (IIId)

Symbols in Formula (IIId) are each synonymous with those in Formula (II), and the preferred ranges are also the same.

Preferred examples of the compound represented by Formula (III) include compounds represented by Formula (IIId-2).

[Chem. 113]

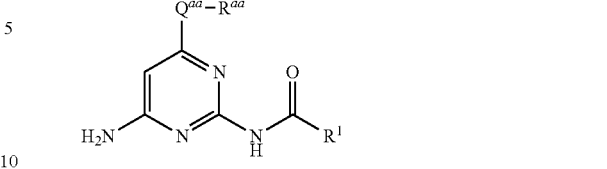

Formula (IIId-2)

Symbols in Formula (IIId-2) are each synonymous with those in Formula (II), and the preferred ranges are also the same. Q$^{aa}$ represents a single bond or —O—, —NH—, or —N(R)— (wherein R is an alkyl group having 1 to 8 carbon atoms). R$^{aa}$ represents a hydrogen atom, a halogen atom, or an alkyl group having 1 to 8 carbon atoms.

Preferred examples of the compound represented by Formula (III) include compounds represented by Formula (IIIe).

[Chem. 114]

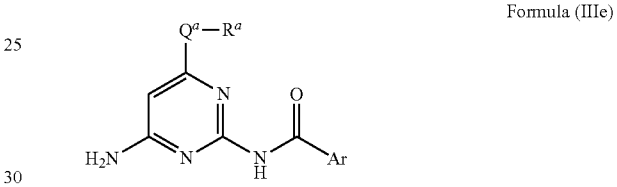

Formula (IIIe)

Symbols in Formula (IIIe) are each synonymous with those in Formula (II), and the preferred ranges are also the same. Ar represents an aryl group. The aryl group optionally has one or more substituents.

The aryl group represented by Ar is preferably a substituted or unsubstituted phenyl or naphthyl group and more preferably a phenyl group. The aryl group represented by Ar optionally has one or more substituents. Examples of the substituent include those belonging to the substituent group T, and preferred examples of the substituent are the same as those possessed by R$^1$ or R$^3$ in Formula (II).

Preferred examples of the compound represented by Formula (III) include compounds represented by Formula (IIIe-2).

[Chem. 115]

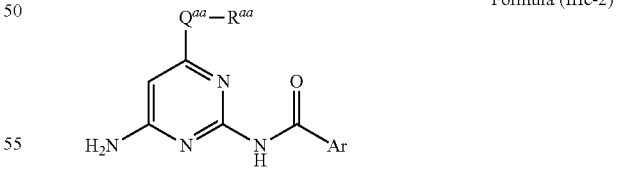

Formula (IIIe-2)

Symbols in Formula (IIIe-2) are each synonymous with those in Formula (II), and the preferred ranges are also the same. Q$^{aa}$ represents a single bond or —O—, —NH—, or —N(R)— (wherein R is an alkyl group having 1 to 8 carbon atoms). R$^{aa}$ represents a hydrogen atom, a halogen atom, or an alkyl group having 1 to 8 carbon atoms.

In Formulae (III) to (IIIe), Q$^a$ is preferably a single bond or a divalent linking group represented by —O—, —S—, —N(X$^a$—R$^h$)—, or —N(X$^a$—R$^h$)—X$^b$—; more preferably a single bond or —O—, —S—, —NH—, or —N(R)—

(wherein R is an alkyl group having 1 to 8 carbon atoms and preferably 1 to 4 carbon atoms); and most preferably a single bond or —O—. $R^a$ is preferably a hydrogen atom, a halogen atom, an alkyl group having 1 to 8 carbon atoms, an alkenyl group having 2 to 8 carbon atoms, an alkynyl group having 2 to 8 carbon atoms, an aryl group having 6 to 18 carbon atoms (e.g., a benzene ring or naphthalene ring group), a heterocyclic group having 4 to 10 carbon atoms (e.g., a pyrrolyl group, a pyrrolidino group, a pyrazolyl group, a pyrazolidino group, an imidazolyl group, a piperazino group, or a morpholino group); more preferably a hydrogen atom or an alkyl group having 1 to 8 carbon atoms; and most preferably an alkyl group having 1 to 4 carbon atoms. The alkyl group may be substituted, but is preferably unsubstituted. Examples of the substituent include a hydroxyl group, a cyano group, alkoxy groups, alkoxycarbonyl groups, and an amino group. When $Q^a$ is —N(R)—, $R^a$ is optionally bonded to R to form a ring (e.g., 5- or 6-membered ring).

Preferred examples of -$Q^a$-$R^a$ include —Cl, —CH$_3$, -(t)C$_4$H$_9$, —OH, —OCH$_3$, —OC$_2$H$_5$, —NHCH$_3$, NHC$_2$H$_5$, —NHC$_3$H$_7$, —NHC$_4$H$_9$, —N(CH$_3$)$_2$, and —N(C$_2$H$_5$)$_2$. In particular, —Cl, —CH$_3$, —OH, —OCH$_3$, —NHCH$_3$, and NHC$_2$H$_5$ are preferred.

Preferred examples of the compound represented by Formula (III) include compounds represented by Formulae (IIIf) to (IIIh).

[Chem. 116]

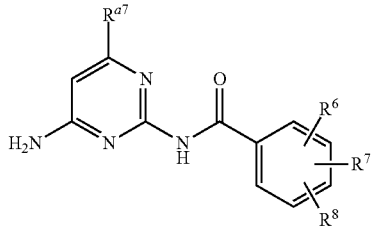

Formula (IIIf)

In Formula (IIIf), $R^{a7}$ represents an alkyl group having 1 to 8 carbon atoms; and $R^6$, $R^7$, and $R^8$ each independently represent a hydrogen atom, a halogen atom, a nitro group, a cyano group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms.

[Chem. 117]

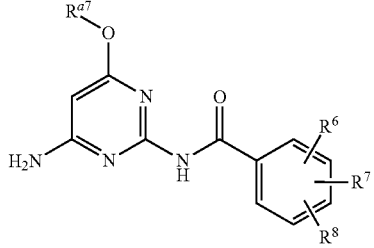

Formula (IIIg)

Symbols in Formula (IIIg) are each synonymous with those in Formula (IIIf), and the preferred ranges are also the same.

[Chem. 118]

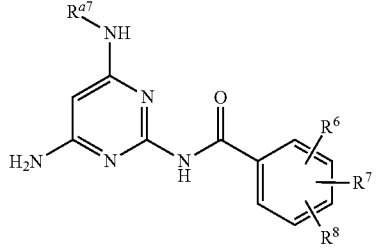

Formula (IIIh)

Symbols in Formula (IIIh) are each synonymous with those in Formula (IIIf), and the preferred ranges are also the same.

Examples of the compound represented by Formula (II) include compounds represented by Formula (IV).

[Chem. 119]

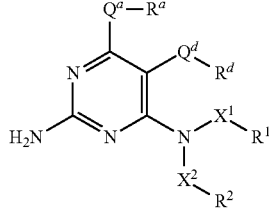

Formula (IV)

Symbols in Formula (IV) are each synonymous with those in Formula (I), and the preferred ranges and specific examples are also the same, provided that compounds where —N(X$^1$R$^1$) X$^2$R$^2$ and -Q$^a$-R$^a$ are —NH$_2$ are excluded.

Preferred examples of the compound represented by Formula (IV) include compounds represented by Formula (IVa).

[Chem. 120]

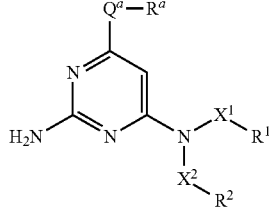

Formula (IVa)

Symbols in Formula (IVa) are each synonymous with those in Formula (II), and the preferred ranges are also the same, provided that compounds where —N(X$^1$R$^1$)X$^2$R$^2$ and -Q$^a$-R$^a$ are —NH$_2$ are excluded.

Preferred examples of the compound represented by Formula (IV) include compounds represented by Formula (IVb).

[Chem. 121]

Formula (IVb)

Symbols in Formula (IVb) are each synonymous with those in Formula (II), and the preferred ranges are also the same, provided that compounds where —X$^1$R$^1$ is a hydrogen atom and -Q$^a$-R$^a$ is —NH$_2$ are excluded.

Preferred examples of the compound represented by Formula (IV) include compounds represented by Formula (IVc).

[Chem. 122]

Formula (IVc)

Symbols in Formula (IVc) are each synonymous with those in Formula (II), and the preferred ranges are also the same. R$^9$ represents —O—Ar, an alkyl group, an alkenyl group, an alkynyl group, an aryl group, or a heterocyclic group, wherein Ar represents an aryl group. The aryl group is the same as those represented by Ar in Formula (IIIc), and examples of the substituent of the aryl group are the same.

Preferred examples of the compound represented by Formula (IV) include compounds represented by Formula (IVd).

[Chem. 123]

Formula (IVd)

Symbols in Formula (IVd) are each synonymous with those in Formula (II), and the preferred ranges are also the same, provided that compounds where -Q$^a$-R$^a$ is —NH$_2$ are excluded.

Preferred examples of the compound represented by Formula (IV) include compounds represented by Formula (IVd-2).

[Chem. 124]

Formula (IVd-2)

Symbols in Formula (IVd-2) are each synonymous with those in Formula (II), and the preferred ranges are also the same. Q$^{aa}$ represents a single bond or —O—, —NH—, or —N(R)— (wherein R is an alkyl group having 1 to 8 carbon atoms). R$^{aa}$ represents a hydrogen atom, a halogen atom, or an alkyl group having 1 to 8 carbon atoms.

Preferred examples of the compound represented by Formula (IV) include compounds represented by Formula (IVe).

[Chem. 125]

Formula (IVe)

Symbols in Formula (IVe) are each synonymous with those in Formula (II), and the preferred ranges are also the same. Ar represents an aryl group. The aryl group is the same as those represented by Ar in Formula (IIIe), and examples of the substituent of the aryl group are also the same. Compounds where -Q$^a$-R$^a$ is —NH$_2$ are excluded.

Preferred examples of the compound represented by Formula (IV) include compounds represented by Formula (IVe-2).

[Chem. 126]

Formula (IVe-2)

Symbols in Formula (IVe-2) are each synonymous with those in Formulae (II) and (IVd-2), and the preferred ranges are also the same. Q$^{aa}$ represents a single bond or —O—, —NH—, or —N(R)— (wherein R is an alkyl group having 1 to 8 carbon atoms). R$^{aa}$ represents a hydrogen atom, a halogen atom, or an alkyl group having 1 to 8 carbon atoms.

Preferred examples of Q$^a$, R$^a$, and -Q$^a$-R$^a$ in Formulae (IV) to (IVe) are the same as those in Formulae (III) to (IIIe).

Preferred examples of the compound represented by Formula (IV) include compounds represented by Formulae (IVf) to (IVh).

[Chem. 127]

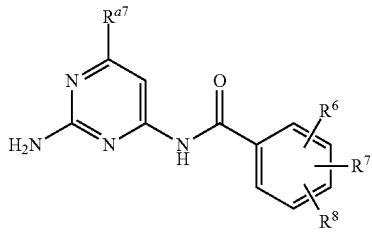

Formula (IVf)

Symbols in Formula (IVf) are each synonymous with those in Formula (IIIf), and the preferred ranges are also the same. $R^{a7}$ represents an alkyl group having 1 to 8 carbon atoms.

[Chem. 128]

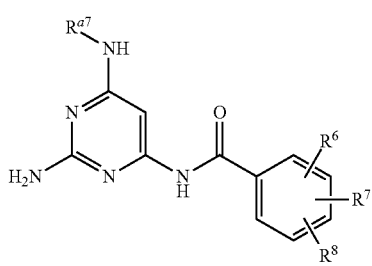

Formula (IVg)

Symbols in Formula (IVg) are each synonymous with those in Formula (IIIf), and the preferred ranges are also the same. $R^{a7}$ represents an alkyl group having 1 to 8 carbon atoms.

[Chem. 129]

Formula (IVh)

Symbols in Formula (IVh) are each synonymous with those in Formula (IIIf), and the preferred ranges are also the same. $R^{a7}$ represents an alkyl group having 1 to 8 carbon atoms.

Preferred examples of the compound represented by Formula (II) include compounds represented by Formula (V).

[Chem. 130]

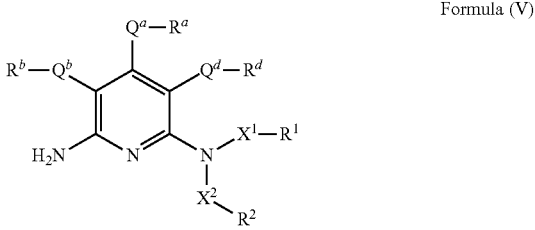

Formula (V)

Symbols in Formula (V) are each synonymous with those in Formula (II), and the preferred ranges and specific examples are also the same.

Preferred examples of the compound represented by Formula (V) include compounds represented by Formula (Va).

[Chem. 131]

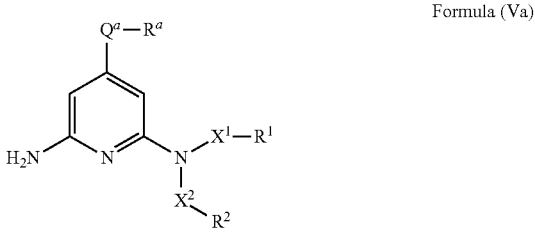

Formula (Va)

Symbols in Formula (Va) are each synonymous with those in Formula (II), and the preferred ranges are also the same.

Preferred examples of the compound represented by Formula (V) include compounds represented by Formula (Vb).

[Chem. 132]

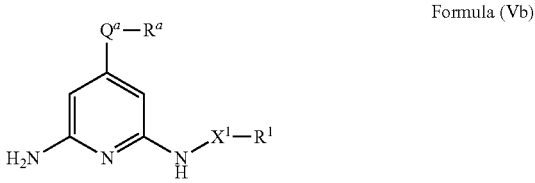

Formula (Vb)

Symbols in Formula (Vb) are each synonymous with those in Formula (II), and the preferred ranges are also the same.

Preferred examples of the compound represented by Formula (V) include compounds represented by Formula (Vc).

[Chem. 133]

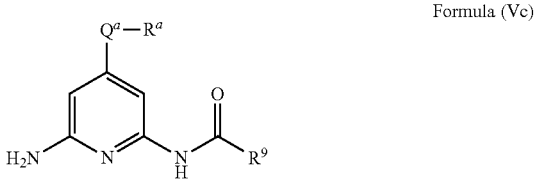

Formula (Vc)

Symbols in Formula (Vc) are each synonymous with those in Formula (II), and the preferred ranges are also the same. $R^9$ represents —O—Ar, an alkyl group, an alkenyl group, an alkynyl group, an aryl group, or a heterocyclic group, wherein Ar represents an aryl group. The aryl group is the same as those represented by Ar in Formula (IIIc), and examples of the substituent of the aryl group are the same.

Preferred examples of the compound represented by Formula (V) include compounds represented by Formula (Vd).

[Chem. 134]

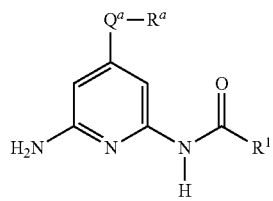

Formula (Vd)

Symbols in Formula (Vd) are each synonymous with those in Formula (II), and the preferred ranges are also the same.

Preferred examples of the compound represented by Formula (V) include compounds represented by Formula (Ve).

[Chem. 135]

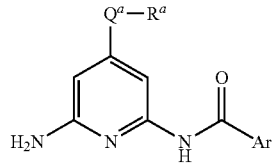

Formula (Ve)

Symbols in Formula (Ve) are each synonymous with those in Formula (II), and the preferred ranges are also the same. Ar represents an aryl group. The aryl group is the same as those represented by Ar in Formula (IIIe), and examples of the substituent of the aryl group are the same. Compounds where -$Q^a$-$R^a$ is —$NH_2$ are excluded.

Preferred examples of $Q^a$, $R^a$, and -$Q^a$-$R^a$ in Formulae (V) to (Ve) are the same as those in Formulae (III) to (IIIe).

Preferred examples of the compound represented by Formula (V) include compounds represented by Formula (Vf).

[Chem. 136]

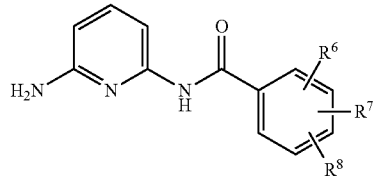

Formula (Vf)

Symbols in Formula (Vf) are each synonymous with those in Formula (IIIf), and the preferred ranges are also the same.

Preferred examples of the compound represented by Formula (V) include compounds represented by Formula (Vf').

[Chem. 137]

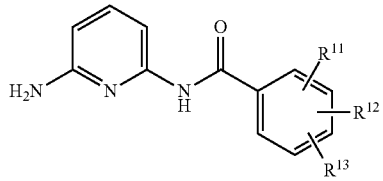

Formula (Vf')

In Formula (Vf'), $R^{11}$, $R^{12}$, and $R^{13}$ each independently represent a hydrogen atom, a nitro group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms, provided that at least one of $R^{11}$, $R^{12}$, and $R^{13}$ represents a substituent other than a hydrogen atom.

The compounds represented by Formulae (I), (II), (III) to (IIIh), (IV) to (IVh), and (V) to (Vf') are preferably used in application that needs relatively low Re and Rth. In addition, polymer films containing these compounds and thereby having controlled Re and/or Rth are characterized by further reduced fluctuations in Re and/or Rth depending on humidity.

Furthermore, in the present invention, a mixture of a compound represented by any one of Formulae (I), (II), (III) to (IIIh), (IV) to (IVh), and (V) to (Vf') and a compound represented by Formula (6) (preferably Formula (7)) shown below may be directly used as an additive for polymer films. The use of a mixture of a compound represented by any one of Formulae (I), (II), (III) to (IIIh), (IV) to (IVh), and (V) to (Vf') and a compound represented by Formula (6) is preferred, because the compounds can synergistically enhance the effect of achieving retardation and the effect of reducing humidity dependency.

[Chem. 138]

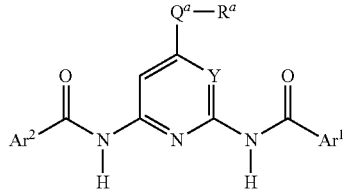

Formula (6)

[Chem. 139]

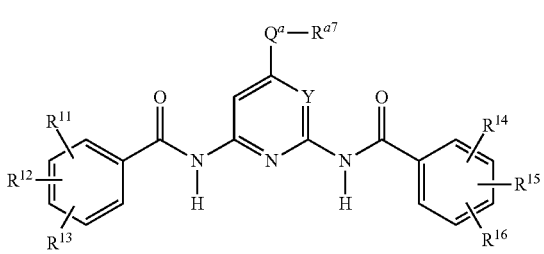

Formula (7)

Ar¹ and Ar² in Formula (6) each independently represent a substituted or unsubstituted aryl group and are each synonymous with Ar in Formulae (IIIe) to (Ve), and preferred examples thereof are also the same. $R^{11}$ to $R^{14}$ in Formula (7) each independently represent a hydrogen atom, a halogen atom, a nitro group, a cyano group, a carbamoyl group, an N-alkylcarbamoyl group having 1 to 8 carbon atoms, an N,N-dialkylcarbamoyl group having 1 to 16 carbon atoms, a sulfamoyl group, an N-alkylsulfamoyl group having 1 to 8 carbon atoms, an N,N-dialkylsulfamoyl group having 1 to 16 carbon atoms, an alkyl group having 1 to 16 carbon atoms, an alkoxy group having 1 to 16 carbon atoms, an alkylamino group having 1 to 16 carbon atoms, a dialkylamino group having 1 to 16 carbon atoms, or an alkoxyalkyloxy group having 1 to 16 carbon atoms and are synonymous with $R^6$ to $R^8$ in Formulae (IIIe) to (Ve) and preferred examples thereof are also the same.

Symbols in the formulae are each synonymous with those in Formula (I), and the preferred ranges and preferred examples are also the same.

The compounds represented by Formulae (I), (II), (III) to (IIIh), (IV) to (IVh), and (V) to (Vf') may be used alone or in the form of a mixture of two or more. For example, a mixture of a compound having a partial structure (x) and a compound having a partial structure (y) shown below may be prepared as a product depending on the synthetic process. Such a mixture can be directly used in various purposes, such as an additive for polymer films. In addition, a compound having the above-described partial structure (a) may be simultaneously prepared, and the mixture containing the compound having the partial structure (a) prepared as a product can be used in various purposes, such as an additive for polymer films. In Formulae below, symbol * indicates a position into which an atom or a residue can be introduced.

[Chem. 140]

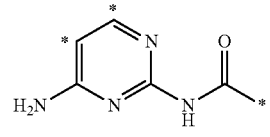
(x)

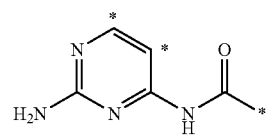
(y)

Specific examples of the compound represented by Formulae (I) and (II) are shown below, but the compounds that can be used in the present invention should not be limited to the following specific examples.

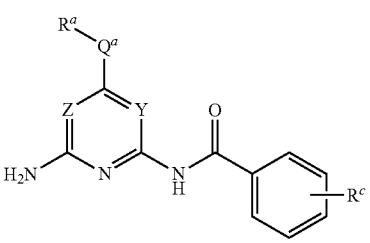

[Chem. 141]

| Compound No. | Y | Z | —Qᵃ—Rᵃ | Rᶜ |
| --- | --- | --- | --- | --- |
| Ib-1 | N | CH | H | H |
| Ib-2 | N | CH | H | o-Me |
| Ib-3 | N | CH | H | m-Me |
| Ib-4 | N | CH | H | p-Me |
| Ib-5 | N | CH | H | p-t-Butyl |
| Ib-6 | N | CH | H | o-OMe |
| Ib-7 | N | CH | H | m-OMe |
| Ib-8 | N | CH | H | p-OMe |
| Ib-9 | N | CH | Me | H |
| Ib-10 | N | CH | Me | o-Me |
| Ib-11 | N | CH | Me | m-Me |
| Ib-12 | N | CH | Me | p-Me |
| Ib-13 | N | CH | Me | p-t-Butyl |
| Ib-14 | N | CH | Me | o-OMe |
| Ib-15 | N | CH | Me | m-OMe |
| Ib-16 | N | CH | Me | p-OMe |
| Ib-17 | N | CH | t-Butyl | H |
| Ib-18 | N | CH | t-Butyl | o-Me |
| Ib-19 | N | CH | t-Butyl | m-Me |
| Ib-20 | N | CH | t-Butyl | p-Me |
| Ib-21 | N | CH | t-Butyl | p-t-Butyl |
| Ib-22 | N | CH | t-Butyl | o-OMe |
| Ib-23 | N | CH | t-Butyl | m-OMe |
| Ib-24 | N | CH | t-Butyl | p-OMe |
| Ib-25 | N | CH | OMe | H |
| Ib-26 | N | CH | OMe | o-Me |
| Ib-27 | N | CH | OMe | m-Me |
| Ib-28 | N | CH | OMe | p-Me |
| Ib-29 | N | CH | OMe | p-t-Butyl |
| Ib-30 | N | CH | OMe | o-OMe |

-continued

| Compound No. | Y | Z | —$Q^a$—$R^a$ | $R^c$ |
|---|---|---|---|---|
| Ib-31 | N | CH | OMe | m-OMe |
| Ib-32 | N | CH | OMe | p-OMe |
| Ib-33 | N | CH | OEt | H |
| Ib-34 | N | CH | OEt | o-Me |
| Ib-35 | N | CH | OEt | m-Me |
| Ib-36 | N | CH | OEt | p-Me |
| Ib-37 | N | CH | OEt | p-t-Butyl |
| Ib-38 | N | CH | OEt | o-OMe |
| Ib-39 | N | CH | OEt | m-OMe |
| Ib-40 | N | CH | OEt | p-OMe |
| Ib-41 | N | CH | OC$_2$H$_2$OEt | H |
| Ib-42 | N | CH | OC$_2$H$_2$OEt | o-Me |
| Ib-43 | N | CH | OC$_2$H$_2$OEt | m-Me |
| Ib-44 | N | CH | OC$_2$H$_2$OEt | p-Me |
| Ib-45 | N | CH | OC$_2$H$_2$OEt | p-t-Butyl |
| Ib-46 | N | CH | OC$_2$H$_2$OEt | o-OMe |
| Ib-47 | N | CH | OC$_2$H$_2$OEt | m-OMe |
| Ib-48 | N | CH | OC$_2$H$_2$OEt | p-OMe |
| Ib-49 | N | CH | NHMe | H |
| Ib-50 | N | CH | NHMe | o-Me |
| Ib-51 | N | CH | NHMe | m-Me |
| Ib-52 | N | CH | NHMe | p-Me |
| Ib-53 | N | CH | NHMe | p-t-Butyl |
| Ib-54 | N | CH | NHMe | o-OMe |
| Ib-55 | N | CH | NHMe | m-OMe |
| Ib-56 | N | CH | NHMe | p-OMe |
| Ib-57 | N | CH | NHEt | H |
| Ib-58 | N | CH | NHEt | o-Me |
| Ib-59 | N | CH | NHEt | m-Me |
| Ib-60 | N | CH | NHEt | p-Me |

[Chem. 142]

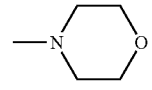

| Compound No. | Y | Z | —$Q^a$—$R^a$ | $R^c$ |
|---|---|---|---|---|
| Ib-61 | N | CH | NHEt | p-t-Butyl |
| Ib-62 | N | CH | NHEt | o-OMe |
| Ib-63 | N | CH | NHEt | m-OMe |
| Ib-64 | N | CH | NHEt | p-OMe |
| Ib-65 | N | CH | NMe$_2$ | H |
| Ib-66 | N | CH | NMe$_2$ | o-Me |
| Ib-67 | N | CH | NMe$_2$ | m-Me |
| Ib-68 | N | CH | NMe$_2$ | p-Me |
| Ib-69 | N | CH | NMe$_2$ | p-t-Butyl |
| Ib-70 | N | CH | NMe$_2$ | o-OMe |
| Ib-71 | N | CH | NMe$_2$ | m-OMe |
| Ib-72 | N | CH | NMe$_2$ | p-OMe |
| Ib-73 | N | CH | morpholino | H |
| Ib-74 | N | CH | C$_6$H$_5$ | H |
| Ib-75 | N | CH | OH | H |
| Ib-76 | CH | N | H | H |
| Ib-77 | CH | N | H | o-Me |
| Ib-78 | CH | N | H | m-Me |
| Ib-79 | CH | N | H | p-Me |
| Ib-80 | CH | N | H | p-t-Butyl |
| Ib-81 | CH | N | H | o-OMe |
| Ib-82 | CH | N | H | m-OMe |
| Ib-83 | CH | N | H | p-OMe |
| Ib-84 | CH | N | Me | H |
| Ib-85 | CH | N | Me | o-Me |
| Ib-86 | CH | N | Me | m-Me |
| Ib-87 | CH | N | Me | p-Me |
| Ib-88 | CH | N | Me | p-t-Butyl |

-continued

| | | | | |
|---|---|---|---|---|
| Ib-89 | CH | N | Me | o-OMe |
| Ib-90 | CH | N | Me | m-OMe |
| Ib-91 | CH | N | Me | p-OMe |
| Ib-92 | CH | N | t-Butyl | H |
| Ib-93 | CH | N | t-Butyl | o-Me |
| Ib-94 | CH | N | t-Butyl | m-Me |
| Ib-95 | CH | N | t-Butyl | p-Me |
| Ib-96 | CH | N | t-Butyl | p-t-Butyl |
| Ib-97 | CH | N | t-Butyl | o-OMe |
| Ib-98 | CH | N | t-Butyl | m-OMe |
| Ib-99 | CH | N | t-Butyl | p-OMe |
| Ib-100 | CH | N | OMe | H |
| Ib-101 | CH | N | OMe | o-Me |
| Ib-102 | CH | N | OMe | m-Me |
| Ib-103 | CH | N | OMe | p-Me |
| Ib-104 | CH | N | OMe | p-t-Butyl |
| Ib-105 | CH | N | OMe | o-OMe |
| Ib-106 | CH | N | OMe | m-OMe |
| Ib-107 | CH | N | OMe | p-OMe |
| Ib-108 | CH | N | OEt | H |
| Ib-109 | CH | N | OEt | o-Me |
| Ib-110 | CH | N | OEt | m-Me |
| Ib-111 | CH | N | OEt | p-Me |
| Ib-112 | CH | N | OEt | p-t-Butyl |
| Ib-113 | CH | N | OEt | o-OMe |
| Ib-114 | CH | N | OEt | m-OMe |
| Ib-115 | CH | N | OC$_2$H$_2$OEt | p-OMe |
| Ib-116 | CH | N | OC$_2$H$_2$OEt | H |
| Ib-117 | CH | N | OC$_2$H$_2$OEt | o-Me |
| Ib-118 | CH | N | OC$_2$H$_2$OEt | m-Me |
| Ib-119 | CH | N | OC$_2$H$_2$OEt | p-Me |
| Ib-120 | CH | N | OC$_2$H$_2$OEt | p-t-Butyl |

[Chem. 143]

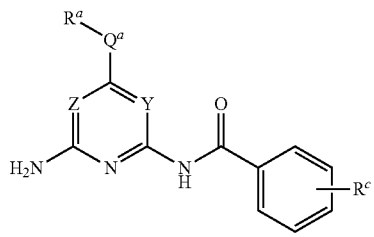

| Compound No. | Y | Z | —Q$^a$—R$^a$ | R$^c$ |
|---|---|---|---|---|
| Ib-121 | CH | N | OC$_2$H$_2$OEt | o-OMe |
| Ib-122 | CH | N | OC$_2$H$_2$OEt | m-OMe |
| Ib-123 | CH | N | OC$_2$H$_2$OEt | p-OMe |
| Ib-124 | CH | N | NHMe | H |
| Ib-125 | CH | N | NHMe | o-Me |
| Ib-126 | CH | N | NHMe | m-Me |
| Ib-127 | CH | N | NHMe | p-Me |
| Ib-128 | CH | N | NHMe | p-t-Butyl |
| Ib-129 | CH | N | NHMe | o-OMe |
| Ib-130 | CH | N | NHMe | m-OMe |
| Ib-131 | CH | N | NHMe | p-OMe |
| Ib-132 | CH | N | NHEt | H |
| Ib-133 | CH | N | NHEt | o-Me |
| Ib-134 | CH | N | NHEt | m-Me |
| Ib-135 | CH | N | NHEt | p-Me |
| Ib-136 | CH | N | NHEt | p-t-Butyl |
| Ib-137 | CH | N | NHEt | o-OMe |
| Ib-138 | CH | N | NHEt | m-OMe |
| Ib-139 | CH | N | NHEt | p-OMe |
| Ib-140 | CH | N | NMe$_2$ | H |
| Ib-141 | CH | N | NMe$_2$ | o-Me |
| Ib-142 | CH | N | NMe$_2$ | m-Me |
| Ib-143 | CH | N | NMe$_2$ | p-Me |
| Ib-144 | CH | N | NMe$_2$ | p-t-Butyl |
| Ib-145 | CH | N | NMe$_2$ | o-OMe |
| Ib-146 | CH | N | NMe$_2$ | m-OMe |
| Ib-147 | CH | N | NMe$_2$ | p-OMe |
| Ib-148 | CH | N | —N(morpholino) | H |

-continued
| Compound No. | | | | |
|---|---|---|---|---|
| Ib-149 | CH | N | C$_6$H$_5$ | H |
| Ib-150 | CH | N | OH | H |
| Ib-151 | CH | CH | H | H |
| Ib-152 | CH | CH | H | o-Me |
| Ib-153 | CH | CH | H | m-Me |
| Ib-154 | CH | CH | H | p-Me |
| Ib-155 | CH | CH | H | p-t-Butyl |
| Ib-156 | CH | CH | H | o-OMe |
| Ib-157 | CH | CH | H | m-OMe |
| Ib-158 | CH | CH | H | p-OMe |
| Ib-159 | N | CH | Cl | H |
| Ib-160 | N | CH | Cl | m-Me |
| Ib-161 | CH | N | Cl | H |
| Ib-162 | CH | N | Cl | m-Me |
[Chem. 144]
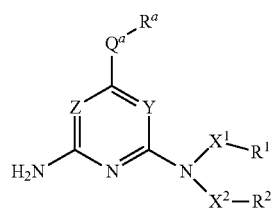
| Compound No. | Y | Z | —Q$^a$—R$^a$ | —X$^1$—R$^1$ | —X$^2$—R$^2$ |
|---|---|---|---|---|---|
| IIb-1 | N | CH | OH | 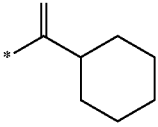 | H |
| IIb-2 | N | CH | Cl | COOMe | H |
| IIb-3 | N | CH | Cl | 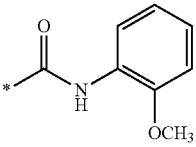 | H |
| IIb-4 | N | CH | H | 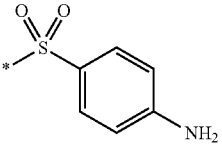 [SMILES: *S(=O)(=O)c1ccc(N)cc1] | H |
| IIb-5 | N | CH | CH$_3$ | C$_5$H$_{11}$ | H |
| IIb-6 | N | CH | 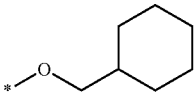 [SMILES: *OCC1CCCCC1] | 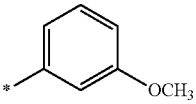 | H |
| IIb-7 | CH | N | Cl | 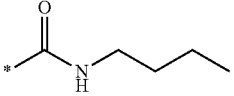 [SMILES: *C(=O)NCCCC] | H |
| IIb-8 | CH | N | Cl | 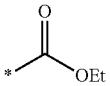 | H |

-continued
| | | | | | |
|---|---|---|---|---|---|
| IIb-9 | CH | N | CH₃ | 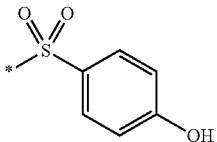 [SMILES: *S(=O)(=O)c1ccc(O)cc1] | H |
| IIb-10 | CH | N | 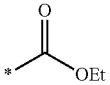 | CH₃ | H |
| IIb-11 | CH | N | C₆H₅ | C₆H₅ | H |
| IIb-12 | N | CH | OCH₃ | CH₃ | CH₃ |
| IIb-13 | N | CH | CH₃ | CH₃ | C₆H₅ |
| IIb-14 | CH | N | CH₃ | CH₃ | CH₃ |
| IIb-15 | CH | N | CH₃ | CH₃ | C₆H₅ |
| IIb-16 | CH | CH | H | 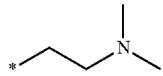 | H |
| IIb-17 | CH | CH | H | COCH₃ | 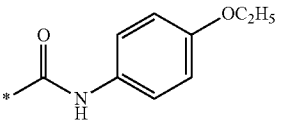 [SMILES: *C(=O)Nc1ccc(OCC)cc1] |
| IIb-18 | CH | CH | H | H | 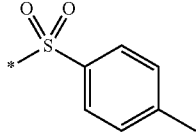 [SMILES: *S(=O)(=O)c1ccc(C)cc1] |
| IIb-19 | CH | CH | H | H | 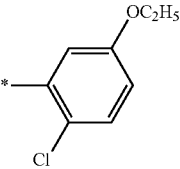 [SMILES: *c1cc(OCC)ccc1Cl] |
| IIb-20 | CH | CH | 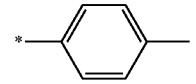 | H | 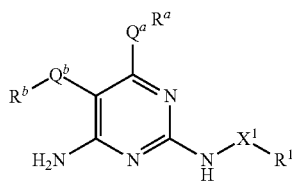 |
| IIb-21 | N | CH | H | —OC₆H₅ | H |
| IIb-22 | CH | N | CH₃ | —OC₆H₅ | H |
[Chem. 145]
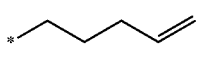 [SMILES: *CCCC=C]
| Compound No. | —Q$^b$—R$^b$ | —Q$^a$—R$^a$ | —X$^1$—R$^1$ |
|---|---|---|---|
| IIIb-1 | SMe | 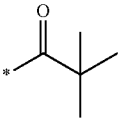 [SMILES: *C(=O)C(C)(C)C] |  |

-continued

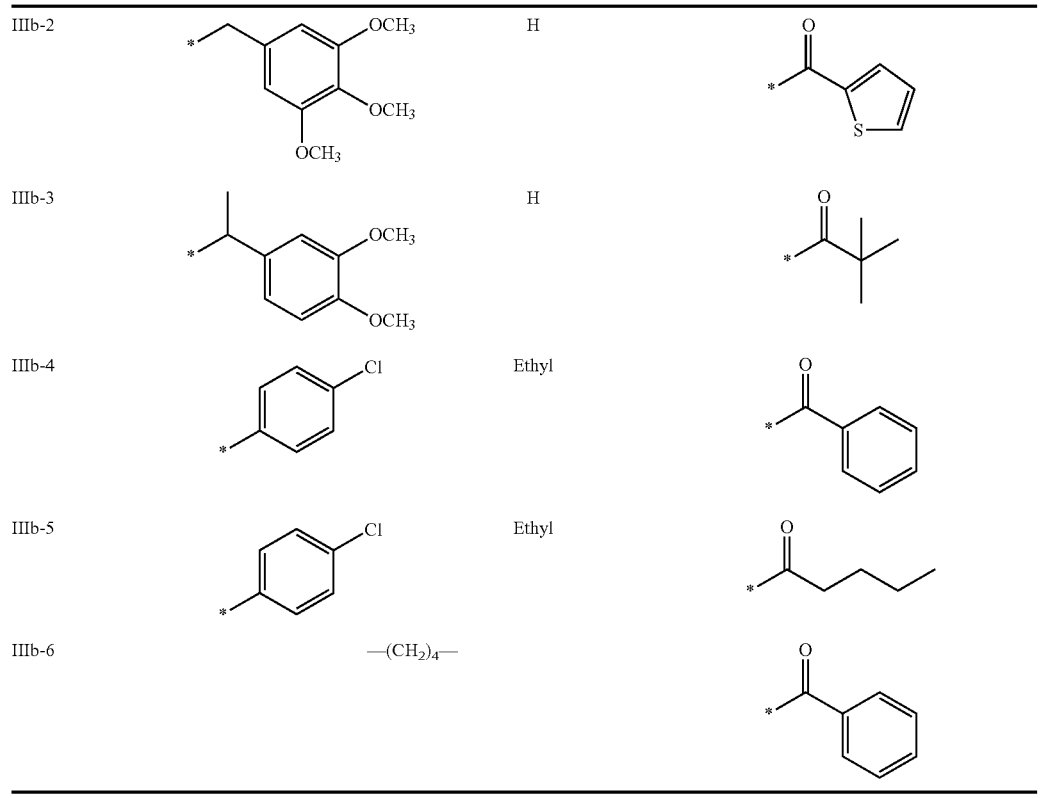

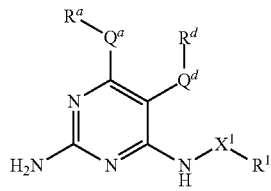

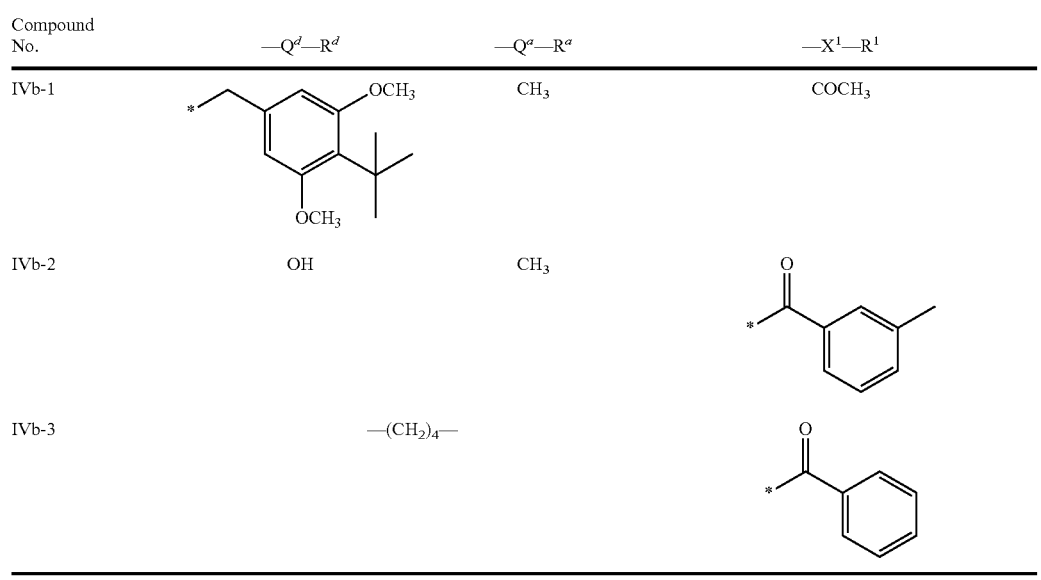

In the following, both compound groups A and B will be described. Hereinafter, the "compound of Formula (0)" and the "inventive compound" should include both compound groups A and B.

The scope of the present invention includes polymer films in which the compounds represented by Formula (0) are added in the form of hydrates of the compounds, solvates of the compounds, or salts of the compound. In the present invention, the hydrate may contain an organic solvent, and the solvate may contain water. That is, the terms "hydrate" and "solvate" should include a solvate mixture containing water and an organic solvent. As described above, a hydrate of the compound, solvate of the compound, and salt of the compound are preferred in the embodiments of solvent-casting method.

The film that the compounds represented by Formula (0) are added in the form of hydrates of the compounds, solvates of the compounds, or salts of the compounds may not maintain the hydrate of the compound, solvate of the compound, or salt of the compound in the film. Even in such a case, the film-forming stability that is provided by the compound in the form such as a hydrate contributes to stabilization of the content of the compound represented by Formula (0) in the resulting film, a reduced variation in optical characteristics of the film, and a reduction in dependency of optical characteristics on environmental humidity.

Examples of the salt include acid addition salts formed with inorganic or organic acids. Examples of the inorganic acid include, but are not limited to, hydrohalic acids (such as hydrochloric acid and hydrobromic acid), sulfuric acid, and phosphoric acid. Examples of the organic acid include, but are not limited to, acetic acid, trifluoroacetic acid, oxalic acid, citric acid, benzoic acid, alkyl sulfonic acids (such as methanesulfonic acid), and allylsulfonic acids (benzenesulfonic acid, 4-toluenesulfonic acid, 1,5-naphthalenedisulfonic acid). Among them, hydrochlorides and acetates are preferred. Examples of the salt also include, but are not limited to, salts formed by substitution of acidic moieties of parent compounds with metal ions (e.g., alkali metal salts such as sodium and potassium salts, alkaline earth metal salts such as calcium and magnesium salts, ammonium salts, alkali metal ions, alkaline earth metal ions, and aluminum ions or formed through preparation with organic bases (such as ethanolamine, diethanolamine, triethanolamine, morpholine, and piperidine). In particular, sodium salts and potassium salts are preferred.

Examples of the solvent contained in a solvate include organic solvents that are usually used. Specific examples thereof include alcohols (e.g., methanol, ethanol, 2-propanol, 1-butanol, 1-methoxy-2-propanol, and t-butanol), esters (e.g., ethyl acetate), hydrocarbons (e.g., toluene, hexane, and heptane), ethers (e.g., tetrahydrofuran), nitriles (e.g., acetonitrile), and ketones (e.g., acetone and 2-butanone). Preferred examples are solvates of alcohols (e.g., methanol, ethanol, 2-propanol, 1-butanol, 1-methoxy-2-propanol, and t-butanol), and more preferred examples are methanol, ethanol, 2-propanol, and 1-butanol. These solvents may be reaction solvents that are used in synthesis of the compounds or solvents that are used in crystallization purification after synthesis or may be mixtures thereof.

In addition, the solvate may contain two or more solvents or may contain water and a solvent (e.g., water and alcohol (such as methanol, ethanol, or t-butanol)).

The inventive compound may be in a hydrate, solvate, or solvate mixture form in which the compound and water and/or a solvent are present at a certain proportion and of which the water content ratio, solvent content ratio, or solvent mixture content ratio does not change within certain ranges of temperature, humidity, and pressure. Such hydrate, solvate, and solvate mixture have specific crystal structures and show specific diffraction patterns in powder X-ray diffraction (XRD). However, the hydrate, solvate, and solvate mixture exposed to environments, such as high temperature or reduced pressure, beyond the certain ranges lose the water content ratio, solvent content ratio, or the solvent mixture content ratio and may be changed to amorphous forms. Herein, the term "amorphous" refers to a form not having any crystal structure of regularly arranged molecules. The amorphous form can be prepared by, for example, heating the compound in a hydrate, solvate, or solvate mixture form to a temperature higher than the melting point to melt the compound and remove the water or the solvent and then rapidly cooling the compound. The resulting amorphous compound may be hydrated according to the environmental humidity, and the water content ratio varies depending on the environmental humidity. However, this hydrous amorphous compound does not show any diffraction pattern in powder X-ray diffraction and is therefore distinguished from the hydrate composed of the inventive compound and water at a proportion within a certain range and of which the water content ratio does not change within certain ranges of temperature, humidity, and pressure.

The inventive compound in an amorphous form not showing any powder X-ray diffraction pattern has a variable water content ratio depending on the environmental humidity. Accordingly, the compound is preferably used in a crystal form (anhydride, hydrate, solvate, or solvate mixture) showing a powder X-ray diffraction pattern.

The compound in the present invention in an amorphous form has a variable water content ratio depending on the environmental humidity and is therefore preferably used in a crystal form (anhydride, hydrate, and/or solvate).

Herein, the term "crystal" refers to a solid having a crystal structure composed of constituent atoms that are regularly and three-dimensionally arranged. Crystals may be in the form of an anhydride, hydrate, and/or solvate and usually have a specific crystal structure and peaks at diffraction angles corresponding to crystal planes in a powder X-ray diffractogram. Throughout the specification, such characteristics are described as "showing a diffraction pattern in a crystalline powder X-ray diffractogram". A compound in an amorphous form usually has a broad single peak (halo) in powder X-ray diffraction. Throughout the specification, such characteristics are described as not showing any diffraction pattern in powder X-ray diffraction. An amorphous form and a crystalline form can also be distinguished from each other by analysis such as thermal analysis, as well as powder X-ray diffraction.

In a hydrate, solvate, or solvate mixture form, water, a solvent, or a solvent mixture may be incorporated into the compound represented by Formula (0) at any proportion. In a hydrate or a solvate, the number of water and/or solvent molecules incorporated into one molecule of a compound is generally an integral multiple, however, the water and/or solvent may also be incorporated into gaps between crystals. In such a case, the proportion is not an integral multiple.

In the hydrate or solvate of the present invention, the proportion of the number of water and/or solvent molecules to one molecule of the compound is not limited, but is preferably 0.25 to 4 molecules of water and/or solvent for one molecule of the compound.

In terms of weight, for example, a water content ratio of 0.8 to 25% is preferred in a case of hydrate though it depends on the molecular weight of the compound.

The water content ratio of the hydrate is preferably 1% or more and more preferably 2% or more, in particular, for reducing the variations in optical characteristics of a film. The upper limit of the water content ratio is preferably 15% or less and more preferably 10% or less, from the viewpoints of solubility (in an organic solvent) and load on the production process. The same can apply to the solvent content ratio in a solvate.

The hydrate can be produced by crystallizing the compound from water. Since many organic solvents contain a slight amount of water, crystallization from an organic solvent also gives a hydrate having a water content ratio within the above-mentioned range. Furthermore, crystallization from an organic solvent containing a required amount of water can also give a hydrate having a water content ratio within the above-mentioned range.

The compound represented by Formula (0) used in the present invention preferably has a molecular weight of 200 to 2000, more preferably 200 to 1000, and most preferably 200 to 600.

The compound represented by Formula (0) may be produced by any method, and various methods are applicable. Nonlimiting examples of the method will now be described.

The compound represented by Formula (0) can be synthesized by, for example, the process of Scheme 1-1. That is, the compound can be synthesized by a reaction of a compound of Formula (1a) with a compound of Formula (1b) under a solvent-free condition or in an organic solvent. The groups in Formulae (1a) and (1b) are each synonymous with those in Formula (1) or (I). Z represents a leaving group and is preferably a halogen atom (e.g., Cl, Br, or I), a hydroxyl group, an alkoxy groups (preferably $C_1$ to $C_4$ alkoxy group, more preferably $C_1$ to $C_2$ alkoxy group, and most preferably $C_1$ alkoxy group), an aryloxy groups (preferably $C_1$ to $C_8$ aryloxy group), a hetero ring group, an acyloxy groups (preferably $C_2$ to $C_8$ acyloxy group), an alkylsulfonyloxy groups (preferably $C_1$ to $C_4$ alkylsulfonyloxy group), or an arylsulfonyloxy group. In particular, a halogen atom, an alkoxy group, an aryloxy group, or an acyloxy group is preferred.

The compounds represented by Formula (1a) and Formula (1b) may be commercially available products or may be synthesized by known processes. Examples of the usable organic solvent include alcohols (e.g., methanol, ethanol, 1-butanol, 1-methoxy-2-propanol, and t-butanol), esters (e.g., ethyl acetate), hydrocarbons (e.g., toluene), ethers (e.g., tetrahydrofuran), amides (e.g., dimethylformamide, dimethylacetamide, N-methylpyrrolidone, and N-ethylpyrrolidone), halogenated hydrocarbons (e.g., dichloromethane), nitriles (e.g., acetonitrile), and solvent mixtures thereof. Among them, hydrocarbons, alcohols, and amides are preferred; and toluene, methanol, ethanol, 1-methoxy-2-propanol, t-butanol, dimethylacetamide, N-methylpyrrolidone, and N-ethylpyrrolidone are particularly preferred. Solvent mixtures of toluene, methanol, ethanol, 1-methoxy-2-propanol, t-butanol, dimethylacetamide, N-methylpyrrolidone, or N-ethylpyrrolidone are also particularly preferred. A mixture of an organic solvent and water is also preferred.

The reaction of a compound of Formula (1a) with a compound of Formula (1b) can be also preferably performed in the presence of a base. The base may be an inorganic base (e.g., potassium carbonate, sodium bicarbonate, sodium hydroxide, or potassium hydroxide) or an organic base (e.g., pyridine, triethylamine, sodium methoxide, sodium ethoxide, t-butoxy potassium, or t-butoxy sodium), and can be appropriately selected according to the type of Z. When Z is an alkoxy group, the base is preferably an inorganic base, in particular, sodium methoxide. The amount of the base is preferably in a range of 0.5 to 10 equivalents, more preferably 0.5 to 6 equivalents, to the compound represented by Formula (1b). When Z is a halogen atom, inorganic bases and organic bases are both preferable, and, for example, pyridine and sodium bicarbonate are more preferred.

The reaction temperature is usually in a range of −20° C. to the boiling point of the solvent and preferably in a range of room temperature to the boiling point of the solvent.

The reaction time ranges usually from 10 minutes to 3 days and preferably from 1 hour to 1 day. The reaction may be performed under a nitrogen atmosphere or reduced pressure. In particular, when the leaving group Z is an alkoxy group or an aryloxy group, the reaction is also preferably performed under reduced pressure.

Scheme 1-1

[Chem. 147]

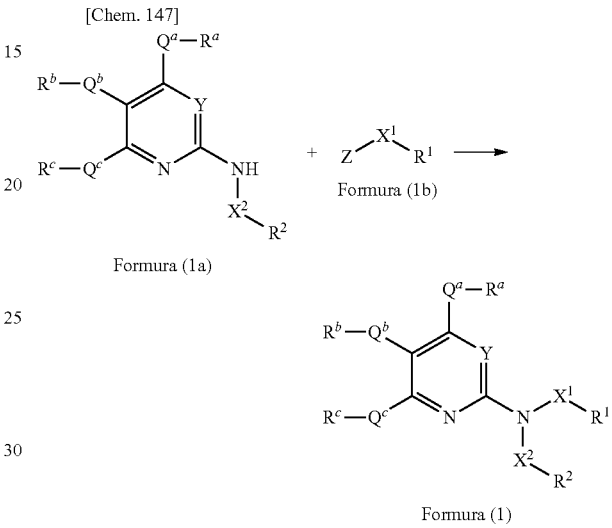

Another example of the method of producing a compound represented by Formula (0) is shown in Scheme 1-2. That is, the compound can be synthesized by a reaction of a compound of Formula (1c) with a compound of Formula (1d) under a solvent-free condition or in an organic solvent, in the absence of a base or in the presence of a base.

The compounds represented by Formula (1c) and Formula (1d) may be commercially available products or may be synthesized by known processes. Examples of the usable organic solvent include alcohols (e.g., methanol and ethanol), esters (e.g., ethyl acetate), hydrocarbons (e.g., toluene), ethers (e.g., tetrahydrofuran), amides (e.g., dimethylformamide, dimethylacetamide, N-methylpyrrolidone, and N-ethylpyrrolidone), halogenated hydrocarbons (e.g., dichloromethane), nitriles (e.g., acetonitrile), and solvent mixtures thereof. Alcohols and amides are preferred; and methanol, ethanol, 1-methoxy-2-propanol, t-butanol, dimethylacetamide, N-methylpyrrolidone, and N-ethylpyrrolidone are particularly preferred. Solvent mixtures of methanol, ethanol, 1-methoxy-2-propanol, t-butanol, dimethylacetamide, N-methylpyrrolidone, or N-ethylpyrrolidone are also particularly preferred.

When a base is used, the base may be an inorganic base (e.g., potassium carbonate) or an organic base (e.g., triethylamine, sodium methoxide, or sodium ethoxide). The inorganic base is preferred, in particular, sodium hydroxide, sodium carbonate, and sodium bicarbonate are preferred. The amount of the base is preferably in a range of 0.5 to 10 equivalents, more preferably 1 to 5 equivalents, to the compound represented by Formula (1c).

The reaction temperature is usually in a range of −20° C. to the boiling point of the solvent and preferably in a range of room temperature to the boiling point of the solvent.

The reaction time ranges usually from 10 minutes to 3 days and preferably from 1 hour to 1 day. The reaction may be performed under a nitrogen atmosphere or reduced pressure.

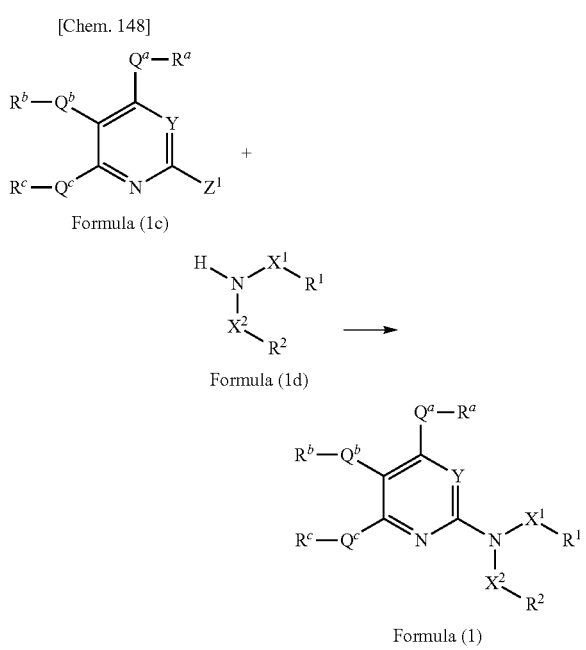

The groups in Formulae (1c) and (1d) are each synonymous with those in the formulae mentioned above. $Z^1$ represents a leaving group and is preferably a halogen atom.

The compound of Formula (2)', which is a compound belonging to the compound group A and is an example of Formula (2), can be synthesized by, for example, the process of Scheme 2-1. That is, the compound can be synthesized by a reaction of a compound of Formula (2a) with a compound of Formula (1b) under a solvent-free condition or in an organic solvent, in the presence of a base. The compounds represented by Formula (2a) and Formula (1b) may be commercially available products or may be synthesized by known processes. Examples of the usable organic solvent and the base are the same as those in the reactions in Schemes 1-1 and 1-2; and the reaction temperature and the reaction time are also the same as those in the above-described Schemes.

The groups in Formula (2a) are each synonymous with those in the formulae mentioned above. Formula (1b) is the same as above.

The compound of Formula (6)', which is an example of Formula (6), can be synthesized by, for example, the process of Scheme 2. That is, the compound can be synthesized by a reaction of a compound of Formula (6a) with a compound of Formula (6b) under a solvent-free condition or in an organic solvent. The compounds represented by Formula (6a) and Formula (6b) may be commercially available products or may be synthesized by known processes. The reaction of a compound of Formula (6a) with a compound of Formula (6b) can be also preferably performed in the presence of a base. Examples of the usable organic solvent and the base are the same as those in the reaction in Scheme 1-1; and the reaction temperature and the reaction time are also the same as those in the above-described Schemes.

The groups in Formulae (6a) and (6b) are each synonymous with those in Formula (6). Ar is an aryl group. Z is synonymous with that in Formula (1b). The leaving group Z is preferably a halogen atom, an alkoxy group, an aryloxy group, or an acyloxy group, more preferably an alkoxy group, more preferably a $C_1$ to $C_4$ alkoxy group, more preferably a $C_1$ to $C_2$ alkoxy group, and most preferably a $C_1$ alkoxy group.

The compound of Formula (7-1) can be synthesized by, for example, the process of Scheme 3. That is, the compound can be synthesized by a reaction of a compound of Formula (7a) with a compound of Formula (7b) under a solvent-free condition or in an organic solvent. The compounds represented by Formula (7a) and Formula (7b) may be commercially available products or may be synthesized by known processes. The reaction of a compound of Formula (7a) with a compound of Formula (7b) can be also preferably performed in the presence of a base. Examples of the usable organic solvent and the base are the same as those in the reaction in Scheme 1-1; and the reaction temperature and the reaction time are also the same as those in the above-described Schemes.

Scheme 3

[Chem. 151]

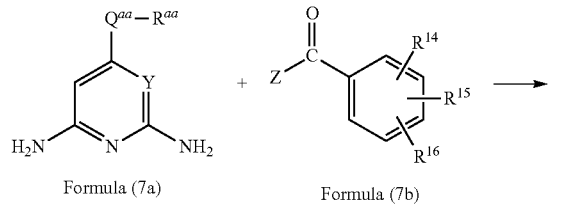

Formula (7a)    Formula (7b)

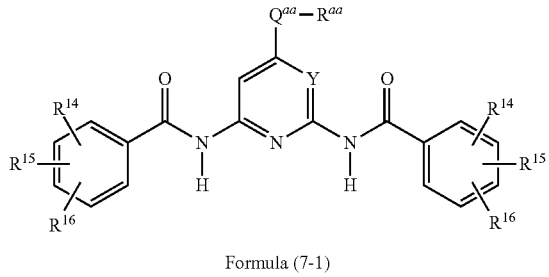

Formula (7-1)

The groups in Formulae (7a) and (7b) are each synonymous with those in Formula (7-1). Z is synonymous with that in Formula (1b) and is preferably a halogen atom, an alkoxy group, an aryloxy group, or an acyloxy group, more preferably an alkoxy group, more preferably a $C_1$ to $C_4$ alkoxy group, more preferably a $C_1$ to $C_2$ alkoxy group, and most preferably a $C_1$ alkoxy group.

The starting material, a diaminopyrimidine compound represented by Formula (7a), may be a commercially available product or may be synthesized by a known process. Alternatively, a compound of Formula (7a) synthesized from commercially available materials may be directly used without purification for the reaction.

Examples of the commercially available compound usable as a raw material in the synthesis examples of Schemes 1-1, 1-2, 2, and 3 include 2,4,6-trichloropyrimidine, 2-amino-4,6-dichloropyrimidine, 2,4-diamino-6-chloropyrimidine, 2,4-diamino-6-hydroxypyrimidine, and 2,4-diaminopyridine. The inventive compound can be synthesized from these materials by combining a nucleophilic substitution reaction and a condensation reaction, for example.

The compound of Formula (1) and a precursor thereof can also be synthesized by direct construction of a hetero ring (pyrimidine ring or pyridine ring) through a cyclization reaction. Thus, various known processes can be employed.

The compounds of Formulae (IIIe) and (IVe), which are compounds belonging to the compound group B, can be synthesized by, for example, the processes of Scheme II shown below. That is, the compounds of Formulae (IIIe) and (IVe) can be synthesized by a reaction of a compound of Formula (IIIe-a) with a compound of Formula (IIIe-b) and a reaction of a compound of Formula (IVe-a) with a compound of Formula (IVe-b), respectively, under a solvent-free condition or in an organic solvent. The compounds represented by Formulae (IIIe-a), (IVe-a), (IIIe-b), and (IVe-b) may be commercially available products or may be synthesized by known processes. Examples of the usable organic solvent and the base are the same as those in the reactions in Schemes 1-1 and 1-2; and the reaction temperature and the reaction time are also the same as those in the above-described Schemes.

The groups in Formulae (IIIe-a), (IVe-a), (IIIe-b), and (IVe-b) are each synonymous with those in Formulae (IIIe) and (IVe). Z is synonymous with that in Formula (1b) and is preferably a halogen atom, an alkoxy group, an aryloxy group, or an acyloxy group, and more preferably an alkoxy group.

Scheme II

[Chem. 152]

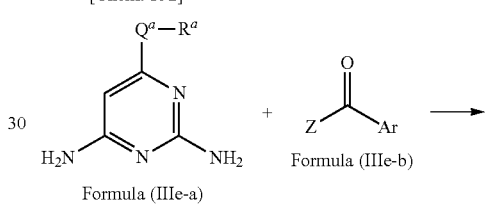

Formula (IIIe-a)    Formula (IIIe-b)

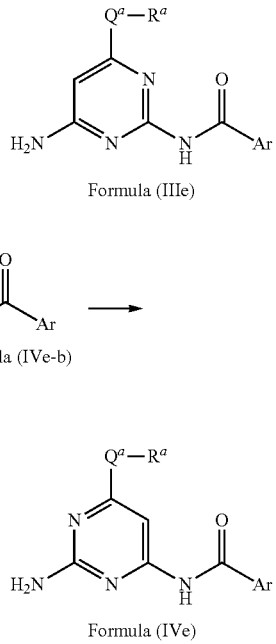

The compounds of Formulae (IIIe) and (IVe) can also be synthesized by, for example, the processes of Scheme III shown below. That is, the compounds can be synthesized by hydrolysis or solvolysis of a compound of Formula (IIIe-c) under a solvent-free condition or in an organic solvent in the presence of an acid or a base.

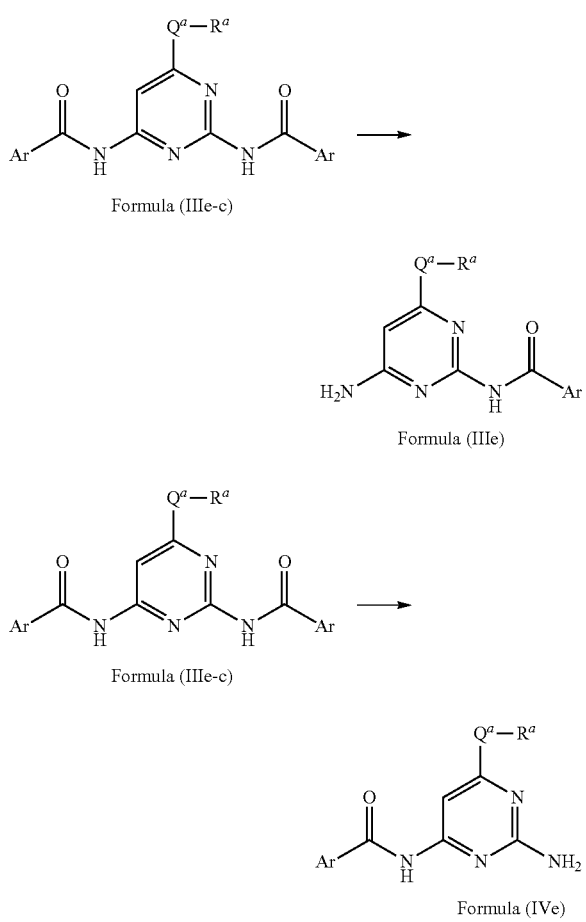

Scheme III
[Chem. 153]

Formula (IIIe-c)

Formula (IIIe)

Formula (IIIe-c)

Formula (IVe)

The inventive compound may be isolated by any common method and is preferably extracted in the form of crystals by crystallization. The crystallization can be performed using a common organic solvent or water. Isolation in a hydrate form by crystallization from water is also preferred.

(1-2) Polymer

The polymer film of the present invention contains, as a main component, one or more polymers selected from various polymer materials. Any polymer can be used, and examples of the usable polymer include polymers having hydroxyl groups. Examples of the hydroxyl group-containing polymer include polyvinyl alcohol, modified products thereof, and cellulose acylate resins. The examples of the hydroxyl group-containing polymer include derivatives in which the hydroxyl groups are substituted by other substituents and cellulose acylate resins in which all hydroxyl groups are substituted by acyl groups.

In one embodiment, the film of the present invention contains a cellulose acylate resin as the hydroxyl group-containing polymer. Cellulose has free hydroxyl groups at 2-, 3-, and 6-positions per β-1,4-bonding glucose unit. The film in this embodiment preferably contains the cellulose acylate resin as a main component. Herein, the term "contain as a main component" has the following meanings: when a cellulose acylate film contains a single cellulose acylate resin as the material of the film, the cellulose acylate resin is the main component; and when a cellulose acylate film contains multiple cellulose acylate resins, the cellulose acylate resin having the highest proportion is the main component.

The starting cellulose for the cellulose acylate includes cotton linter and wood pulp (hardwood pulp, softwood pulp), etc.; and any cellulose acylate obtained from any starting cellulose can be used herein. As the case may be, different starting celluloses may be mixed for use herein. The starting cellulose materials are described in detail, for example, in "Plastic Material Lecture (17), Cellulosic Resin" (written by Marusawa & Uda, published by Nikkan Kogyo Shinbun, 1970), and in Hatsumei Kyokai Disclosure Bulletin No. 2001-1745, pp. 7-8. Any cellulose material described in these can be used here with no specific limitation.

The cellulose acylate resin may contain any acyl group, but are not limited to, the acyl group is preferably an acetyl group, a propionyl group, or a butyryl group, and more preferably an acetyl group.

Specifically, the cellulose acylate resin preferably contains cellulose acylate simultaneously satisfying the following expressions (i) to (iii):

$2.0 \leq A+B \leq 3$,  Expression (i):

$1.0 \leq A \leq 3$, and  Expression (ii):

$0 \leq B \leq 1.0$.  Expression (iii):

In the expressions (i) to (iii), A represents the degree of acetyl substitution, and B represents the sum of the degree of propionyl substitution and the degree of butyryl substitution.

The degree of acyl substitution in the cellulose acylate resin more preferably simultaneously satisfies the following expressions (iv) to (vi):

$2.0 \leq A+B \leq 3$,  Expression (iv):

$1.5 \leq A \leq 3$, and  Expression (v):

$B=0$.  Expression (vi):

In the expressions (iv) to (vi), A represents the degree of acetyl substitution, and B represents the sum of the degree of propionyl substitution and the degree of butyryl substitution.

The degree of acetyl substitution, the degree of propionyl substitution, and the degree of butyryl substitution in a cellulose acylate resin respectively mean the proportions of acetylation and propionylation and/or butyrylation of three hydroxyl groups of a constituent unit ((β)-1,4-glycoside bonding glucose) of cellulose. Throughout the specification, the degrees of acetyl substitution, propionyl substitution, and butyryl substitution of a cellulose acylate resin can be calculated from the observed amount of the bonding fatty acid per the constituent unit mass of cellulose. The measurement is performed in accordance with "ASTM D817-91".

The cellulose acylate resin preferably has a degree of polymerization of 350 to 800 and more preferably 370 to 600. The cellulose acylate resin used in the present invention preferably has a number-average molecular weight of 70000 to 230000, more preferably 75000 to 230000, and most preferably 78000 to 120000.

The cellulose acylate resin can be synthesized using an acid anhydride or an acid chloride as the acylating agent. A most common synthesis on an industrial scale is as follows: Cellulose obtained from cotton linter or wood pulp is esterified with a mixed organic acid component containing organic acids (acetic acid, propionic acid, and butyric acid) corresponding to the acetyl group and the propionyl group and/or the butyryl group or acid anhydrides thereof (acetic anhydride, propionic anhydride, and butyric anhydride) to synthesize an intended cellulose acylate resin.

(1-3) Amount of Inventive Compound

The amount of a compound represented by Formula (1), i.e., a compound belonging to the compound group A, in a film of the present invention is preferably 30 parts by mass or less, more preferably 0.01 to 30 parts by mass, more preferably 0.01 to 20 parts by mass, and most preferably 0.1 to 15 parts by mass, based on 100 parts by mass of the main polymer component (e.g., a hydroxyl group-containing polymer).

The total content of additives (optionally including another additive together with the compound represented by Formula (1)) contained in the film of the present invention is preferably 55% by mass or less, more preferably 35% by mass or less, more preferably 30% by mass or less, and most preferably 20% by mass or less, based on 100 parts by mass of the main polymer component.

The compounds represented by Formula (1) may be used alone or in combination of two or more. A reaction mixture produced using two or more compounds represented by Formula (1b) or Formula (7b) in the process of Scheme 2-1 or 3-1 can be preferably used.

When two or more compounds represented by Formula (1) are used as described above, it is preferable that the total amount of the compounds represented by Formula (1) be within the preferred range mentioned above.

The compound represented by Formula (1) may be prepared in the form of a hydrate of the compound or a solvate of the compound, and such a hydrate or solvate may be directly used or may be used after removal of water or the solvent. If the water or the solvent of crystals prepared in the form of a hydrate or a solvate has been removed once, the content of the compound may vary by, for example, moisture adsorption. Accordingly, direct use of the crystals prepared in the form of a hydrate or a solvate is more preferred.

The amount of a compound represented by Formula (I), i.e., a compound belonging to the compound group B, in a film of the present invention is preferably 30 parts by mass or less, more preferably 0.01 to 30 parts by mass, more preferably 0.01 to 20 parts by mass, and most preferably 0.01 to 15 parts by mass, based on 100 parts by mass of the main polymer component (e.g., a hydroxyl group-containing polymer). In order to achieve higher Re and Rth in the use of the compound together with a compound represented by Formula (6) belonging to the compound group A, as described below, the amount of the inventive compound is preferably less than that of the compound of Formula (6). In such an embodiment, the amount of the compound represented by Formula (I) is preferably 0.001 to 5% by mass, more preferably 0.001 to 2% by mass, and most preferably 0.001 to 1% by mass, based on 100 parts by mass of the main polymer component.

The total content of additives (optionally including another additive together with the compound represented by Formula (I)) contained in the film of the present invention is preferably 55% by mass or less, more preferably 35% by mass or less, more preferably 30% by mass or less, and most preferably 20% by mass or less, based on 100 parts by mass of the main polymer component.

The compounds represented by Formula (I) may be used alone or in combination of two or more. A reaction mixture produced using two or more compounds represented by Formula (1b) or Formula (7b) in the process of Scheme 2-1 or 3-1 can be preferably used.

When two or more compounds represented by Formula (I) are used as described above, the total amount of the compounds represented by Formula (I) is within the preferred range mentioned above.

The compound represented by Formula (I) may be prepared in the form of a hydrate or a solvate, and such a hydrate or solvate may be directly used or may be used after removal of water or the solvent. If the water or the solvent of crystals prepared in the form of a hydrate or a solvate has been removed once, the content of the compound may vary by, for example, moisture adsorption. Accordingly, direct use of the crystals prepared in the form of a hydrate or solvate is more preferred.

As described above, in the present invention, a mixture of a compound represented by any of Formulae (I), (II), (III) to (IIIh), (IV) to (IVh), and (V) to (Vf) belonging to the compound group B and a compound represented by Formula (6) (preferably Formula (7)) belonging to the compound group A may be directly used as an additive for a polymer film. In this embodiment, the compound represented by any of Formulae (I), (II), (III) to (IIIh), (IV) to (IVh), and (V) to (Vf) and the compound represented by Formula (6) (preferably Formula (7)) may be mixed at any proportion (when each compound is a mixture of two or more compounds represented by any of Formulae (I), (II), (III) to (IIIh), (IV) to (IVh), and (V) to (Vf) or represented by Formula (6) (preferably Formula (7)), where the proportion is based on the total amount of the compounds). A higher proportion of the compound represented by Formula (6) (preferably Formula (7)) enhances the achievement of Re and Rth and is useful in application in which higher Re and Rth are preferred. On the contrary, a higher proportion of the compound represented by a formula according to the present invention such as Formula (I) is useful in application in which relatively low Re and Rth are preferred. In the former application, the proportion of the compound represented by a formula according to the present invention such as Formula (I) to the compound represented by Formula (6) (preferably Formula (7)) ranges preferably from 0.01 to 5% by mass, more preferably from 0.01 to 3% by mass, and most preferably from 0.01 to 2% by mass. In the latter embodiment, the proportion of the compound represented by Formula (6) (preferably Formula (7)) to the compound represented by a formula according to the present invention such as Formula (I) ranges preferably from 50% by mass or less, more preferably from 20% by mass or less, and most preferably from 10% by mass or less.

(1-4) Other Additives

The polymer film of the present invention may further contain an additive depending on the purpose, in addition to the compound represented by Formula (0). When the polymer film is produced by a solution-casting method, such an additive can be added to polymer resin dope, such as a cellulose acylate dope, at any timing. The additive is selected from agents that compatible (soluble in cellulose acylate dope in liquid film forming) with polymers (e.g., cellulose acylate). The additive is compounded to the polymer film for controlling the optical and other characteristics.

A polymer film according to an embodiment of the present invention contains a compound represented by Formula (1) belonging to the compound group A and at least one compound represented by any one of Formula (IIIe), (IVe), and (Ve) belonging to the compound group B. Symbols in these formulae are synonymous with those in formulae mentioned above, and the preferred ranges and preferred examples are also the same. Ar represents an aryl group and is synonymous with $Ar^1$ in Formula (5-1), and the preferred ranges are the same.

[Chem. 154]

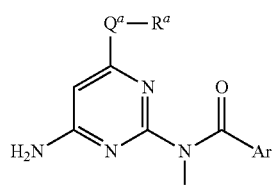

Formula (IIIe)

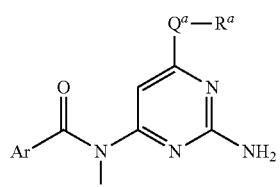

Formula (IVe)

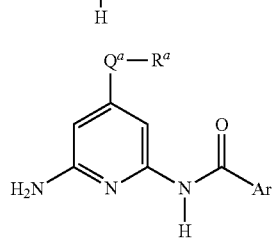

Formula (Ve)

These compounds may be obtained as by-products during synthesis of the compound represented by Formula (6).

The proportion of the amount of the compounds (IIIe), (IVe), and (Ve) to the compound represented by Formula (1) ranges preferably from 5% by mass or less, more preferably from 3% by mass or less, and most preferably from 2% by mass or less. The lower limit of each proportion of the compounds (IIIe), (IVe), and (Ve) is, for example, 0.01% by mass or more. In another embodiment, the polymer film may not contain the compounds (IIIe), (IVe), and (Ve).

The amount of the compounds (IIIe), (IVe), and (Ve) contained in the film of this embodiment is preferably 5 parts by mass or less, more preferably 2.5 parts by mass or less, and most preferably 1.5 parts by mass or less.

Specific examples of the compound represented by Formula (IIIe), (IVe), or (Ve) that is preferably used together with a compound belonging to the compound group A and specific examples of the combination of a compound of Formula (1) belonging to the compound group A and a compound represented by Formula (IIIe), (IVe), or (Ve) belonging to the compound group B are shown, but not limited thereto, below.

[Chem. 155]

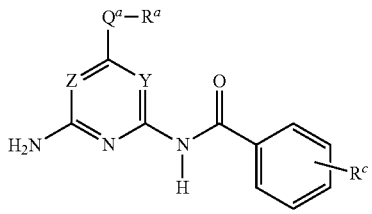

| Compound No. | Y | Z | —$Q^a$—$R^a$ | $R^c$ |
|---|---|---|---|---|
| M-1a | N | CH | CH$_3$ | H |
| M-2a | CH | N | CH$_3$ | H |
| M-3a | N | CH | CH$_3$ | m-CH$_3$ |
| M-4a | CH | N | CH$_3$ | m-CH$_3$ |
| M-5a | N | CH | OCH$_3$ | H |
| M-6a | CH | N | OCH$_3$ | H |
| M-7a | N | CH | OCH$_3$ | m-CH$_3$ |
| M-8a | CH | N | OCH$_3$ | m-CH$_3$ |
| M-9a | N | CH | Cl | H |
| M-10a | CH | N | Cl | H |
| M-11a | N | CH | NHCH$_3$ | m-CH$_3$ |
| M-12a | CH | N | NHCH$_3$ | m-CH$_3$ |
| M-13a | CH | CH | H | H |
| M-14a | CH | CH | H | m-CH$_3$ |

TABLE 1

| Mixture No. | Formula(1) Material | Formula(1) Amount (% by mass) | Formula(IIIe) or Formula(Ve) Material | Formula(IIIe) or Formula(Ve) Amount (% by mass) | Formula(IVe) Material | Formula(IVe) Amount (% by mass) |
|---|---|---|---|---|---|---|
| R-1 | (1-2) | 95 | M-1a | 2.5 | M-2a | 2.5 |
| R-2 | (1-9) | 95 | M-5a | 2.5 | M-6a | 2.5 |
| R-3 | (1-9) | 96 | M-5a | 2 | M-6a | 2 |
| R-4 | (1-9) | 97.5 | M-5a | 2.5 | M-6a | 0 |
| R-5 | (1-9) | 97.5 | M-5a | 0 | M-6a | 2.5 |
| R-6 | (1-9) | 98 | M-5a | 1 | M-6a | 1 |
| R-7 | (1-9) | 99.5 | M-5a | 0.1 | M-6a | 0.4 |
| R-8 | (2-2) | 96 | M-3a | 2 | M-4a | 2 |
| R-9 | (2-2) | 95 | M-3a | 2 | M-4a | 3 |
| R-10 | (2-2) | 95 | M-3a | 0 | M-4a | 5 |
| R-11 | (2-2) | 98.5 | M-3a | 0.5 | M-4a | 1 |
| R-12 | (2-2) | 99.5 | M-3a | 0.1 | M-4a | 0.4 |
| R-13 | (2-2) | 99.8 | M-3a | 0 | M-4a | 0.2 |
| R-14 | (6-16) | 98 | M-9a | 0 | M-10a | 2 |
| R-15 | (7-1) | 95 | M-13a | 5 | — | — |

(Plasticizer)

The polymer film of the present invention preferably contains a plasticizer for improving, for example, the film-forming properties. Use of a saccharide plasticizer selected from a compound group consisting of saccharides and derivatives thereof or an oligomer plasticizer selected from oligomers including polycondensation esters of dicarboxylic acids and diols and derivatives thereof preferably improves the environmental humidity resistance of polymer films. Specifically, the use can reduce the fluctuation in Rth depending on humidity. The effect of reducing the fluctuation in Rth depending on humidity is further enhanced by a combined use of the saccharide plasticizer and the oligomer plasticizer.

(Saccharide Plasticizer)

As described above, the polymer film of the present invention preferably contains at least one compound selected from the compound group consisting of saccharides and derivatives thereof. In particular, a compound selected from the compound group consisting of mono- to decasaccharides and derivatives thereof is a preferred plasticizer. Examples of such a compound include sugar derivatives in which a part or all of hydrogen atoms of hydroxyl groups of sugars such as glucose are substituted by acyl groups described in paragraphs [0042] to [0065] of International Publication No. WO2007/125764. The amount of the saccharide plasticizer is preferably 0.1% by mass or more and less than 20% by mass, more preferably 0.1% by mass or more and less than 10% by mass, and most preferably 0.1% by mass or more and less than 7% by mass based on the amount of the main polymer component (e.g., cellulose acylate).

(Oligomer Plasticizer)

As described above, the polymer film of the present invention preferably contains an oligomer plasticizer selected from the oligomers. Preferred examples of the oligomer plasticizer include polycondensation esters of a diol component and a dicarboxylic acid compound and derivatives thereof (hereinafter also referred to as "polycondensation ester based plasticizer"); and oligomers of methyl acrylate (MA) and derivatives thereof (hereinafter also referred to as "MA oligomer plasticizer").

The polycondensation ester is a polycondensation ester of a dicarboxylic acid ingredient and a diol ingredient. The dicarboxylic acid ingredient may consist of one dicarboxylic acid or any mixture of two or more dicarboxylic acids. Among these, the dicarboxylic acid ingredient containing at least one aromatic dicarboxylic acid and at least one aliphatic dicarboxylic acid is preferable. As well as the dicarboxylic acid ingredient, the diol ingredient may consist of one diol or any mixture of two or more diols. Among these, as the diol ingredient, ethylene glycol and/or aliphatic diol having the averaged number of carbon atoms of more than 2 and not more than 3.0 is preferable.

Regarding the ratio of the aromatic dicarboxylic acid to the aliphatic dicarboxylic acid contained in the dicarboxylic acid ingredient, the ratio of the aromatic dicarboxylic acid is preferably from 5 to 70 mol %. In the case that the ratio falls within the range, it is possible to reduce the environmental humidity-dependence and to prevent the bleeding-out from generating in the film formation process. The ratio of the aromatic dicarboxylic acid in the dicarboxylic acid ingredient is more preferably from 10 to 60 mol %, and even more preferably from 20 to 50 mol %.

Examples of the aromatic dicarboxylic acid include phthalic acid, terephthalic acid, isophthalic acid, 1,5-naphthalenedicarboxylic acid, 1,4-naphthalenedicarboxylic acid, 1,8-naphthalenedicarboxylic acid, 2,8-naphthalenedicarboxylic acid, 2,6-naphthalenedicarboxylic acid and the like are preferably used, and phthalic acid and terephthalic acid are more preferred. Examples of the aliphatic dicarboxylic acid that is preferably used in the present invention include oxalic acid, malonic acid, succinic acid, maleic acid, fumaric acid, glutaric acid, adipic acid, pimelic acid, suberic acid, azelaic acid, sebacic acid, dodecanedicarboxylic acid and 1,4-cyclohexanedicarboxylic acid, with succinic acid and adipic acid being preferred.

The diol ingredient is preferably ethylene glycol and/or aliphatic diol having the averaged number of carbon atoms of more than 2 and not more than 3.0. the ratio of ethylene glycol in the diol ingredient is preferably equal to or more than 50 mol %, or more preferably equal to or more than 75 mol %. The aliphatic diol includes alkyl diols and alicyclic diols, and examples thereof include ethylene glycol, 1,2-propanediol, 1,3-propanediol, 1,2-butanediol, 1,3-butanediol, 2-methyl-1,3-propanediol, 1,4-butanediol, 1,5-pentanediol, 2,2-dimethyl-1,3-propanediol (neopentyl glycol), 2,2-diethyl-1,3-propanediol (3,3-dimethylolpentane), 2-n-butyl-2-ethyl-1,3-propanediol (3,3-dimethylolheptane), 3-methyl-1,5-pentanediol, 1,6-hexanediol, 2,2,4-trimethyl-1,3-pentanediol, 2-ethyl-1,3-hexanediol, 2-methyl-1,8-octanediol, 1,9-nonanediol, 1,10-decanediol, 1,12-octadecanediol and diethylene glycol. One kind of or a mixture of two or more kinds of these aliphatic diols is preferably used together with ethanediol.

Among these aliphatic diols, ethylene glycol, 1,2-propanediol and 1,3-propanediol are preferred, and ethylene glycol and 1,2-propanediol are more preferred.

As the polycondensed ester-type plasticizer, the polycondensed ester having the terminal OH forming esters with a monocarboxylic acid are preferable. Preferred examples of the monocarboxylic acid used for capping include acetic acid, propionic acid and butenoic acid. Among these, acetic acid and propionic acid are more preferred, and acetic acid is most preferred. Preferred examples of the monoalcohols used for capping include methanol, ethanol, propanol, isopropanol, butanol and isobutanol, with methanol being most preferred. When the carbon number of monocarboxylic acids used for the terminal end of the polycondensed ester is 3 or less, the loss on heating of the compound is not increased and no surface failure is caused. And any mixture of two or more types of monocarboxylic acids may be used for capping. The polycondensed esters having, at the both ends, the terminal OH forming ester with acetic acid or propionic acid are preferable; and the polycondensed esters having, at the both ends, the terminal OH forming ester with acetic acid are more preferable.

The number average molecular weight of the polycondensed ester is preferably from 700 to 2,000, more preferably from 800 to 1,500, still more preferably from 900 to 1,200. The number average molecular weight of the polycondensed ester for use in the present invention can be measured and evaluated by gel permeation chromatography.

Specific examples of the polycondensed ester for use in the present invention are set forth in Table 1, but the present invention is not limited thereto.

TABLE 2

| | Dicarboxylic acid | | | Diol | | | | |
| --- | --- | --- | --- | --- | --- | --- | --- | --- |
| | Aromatic dicarboxylic acid | Aliphatic dicarboxylic acid | Ratio of dicarboxylic acid(s) (mol %) | Aliphatic diol(s) | Ratio of Aliphatic diol(s) (mol %) | Averaged numbers of carbon atoms in Aliphatic diol(s) (mol %) | Both terminals | Number-averaged molecular weight |
| P-1 | PA | AA | 10/90 | Ethylene glycol | 100 | 2.0 | acetyl ester residue | 1000 |
| P-2 | PA | AA | 25/75 | Ethylene glycol | 100 | 2.0 | acetyl ester residue | 1000 |

TABLE 2-continued

| | Dicarboxylic acid | | | Diol | | | | |
|---|---|---|---|---|---|---|---|---|
| | Aromatic dicarboxylic acid | Aliphatic dicarboxylic acid | Ratio of dicarboxylic acid(s) (mol %) | Aliphatic diol(s) | Ratio of Aliphatic diol(s) (mol %) | Averaged numbers of carbon atoms in Aliphatic diol(s) (mol %) | Both terminals | Number-averaged molecular weight |
| P-3 | PA | AA | 50/50 | Ethylene glycol | 100 | 2.0 | acetyl ester residue | 1000 |
| P-4 | PA | SA | 5/95 | Ethylene glycol | 100 | 2.0 | acetyl ester residue | 1000 |
| P-5 | PA | SA | 20/80 | Ethylene glycol | 100 | 2.0 | acetyl ester residue | 1000 |
| P-6 | TPA | AA | 15/85 | Ethylene glycol | 100 | 2.0 | acetyl ester residue | 1000 |
| P-7 | TPA | AA | 50/50 | Ethylene glycol | 100 | 2.0 | acetyl ester residue | 1000 |
| P-8 | TPA | SA | 5/95 | Ethylene glycol | 100 | 2.0 | acetyl ester residue | 1000 |
| P-9 | TPA | SA | 10/90 | Ethylene glycol | 100 | 2.0 | acetyl ester residue | 1000 |
| P-10 | TPA | SA | 15/85 | Ethylene glycol | 100 | 2.0 | acetyl ester residue | 1000 |
| P-11 | TPA | SA | 50/50 | Ethylene glycol | 100 | 2.0 | acetyl ester residue | 1000 |
| P-12 | TPA | SA | 70/30 | Ethylene glycol | 100 | 2.0 | acetyl ester residue | 1000 |
| P-13 | TPA/PA | AA | 10/10/80 | Ethylene glycol | 100 | 2.0 | acetyl ester residue | 1000 |
| P-14 | TPA/PA | AA | 20/20/60 | Ethylene glycol | 100 | 2.0 | acetyl ester residue | 1000 |
| P-15 | TPA/PA | AA/SA | 10/10/40/40 | Ethylene glycol | 100 | 2.0 | acetyl ester residue | 1000 |
| P16 | TPA | AA/SA | 10/30/60 | Ethylene glycol | 100 | 2.0 | acetyl ester residue | 1000 |
| P-17 | TPA | AA/SA | 10/30/60 | Ethylene glycol/ 1,2-propane diol | 50/50 | 2.5 | acetyl ester residue | 1000 |
| P-18 | TPA | AA/SA | 10/30/60 | 1,2-propane diol | 100 | 3.0 | acetyl ester residue | 1000 |
| P-19 | TPA | AA/SA | 10/30/60 | Ethylene glycol | 100 | 2.0 | acetyl ester residue | 700 |
| P-20 | TPA | AA/SA | 10/30/60 | Ethylene glycol | 100 | 2.0 | acetyl ester residue | 850 |
| P-21 | TPA | AA/SA | 10/30/60 | Ethylene glycol | 100 | 2.0 | acetyl ester residue | 1200 |
| P-22 | TPA | AA/SA | 10/30/60 | Ethylene glycol | 100 | 2.0 | acetyl ester residue | 1600 |
| P-23 | TPA | AA/SA | 10/30/60 | Ethylene glycol | 100 | 2.0 | acetyl ester residue | 2000 |
| P-24 | TPA | AA/SA | 10/30/60 | Ethylene glycol | 100 | 2.0 | propionyl ester residue | 1000 |
| P-25 | TPA | AA/SA | 10/30/60 | Ethylene glycol | 100 | 2.0 | butanoyl ester residue | 1000 |
| P-26 | TPA | AA/SA | 10/30/60 | Ethylene glycol | 100 | 2.0 | benzoyl ester residue | 1000 |
| P-27 | TPA | AA/SA | 20/40/40 | Ethylene glycol | 100 | 2.0 | acetyl ester residue | 1000 |
| P-28 | 2,6-NPA | AA/SA | 20/40/40 | Ethylene glycol | 100 | 2.0 | acetyl ester residue | 1200 |
| P-29 | 1,5-NPA | AA/SA | 20/40/40 | Ethylene glycol | 100 | 2.0 | acetyl ester residue | 1200 |
| P-30 | 1,4-NPA | AA/SA | 20/40/40 | Ethylene glycol | 100 | 2.0 | acetyl ester residue | 1200 |
| P-31 | 1,8-NPA- | AA/SA | 20/40/40 | Ethylene glycol | 100 | 2.0 | acetyl ester residue | 1200 |
| P-32 | 2,8-NPA | AA/SA | 20/40/40 | Ethylene glycol | 100 | 2.0 | acetyl ester residue | 1200 |

In Table, PA means phthalic acid; TPA means terephthalic acid; IPA means isophthalic acid; AA means adipic acid; SA means succinic acid; 2,6-NPA means 2,6-naphthalene dicarboxylic acid; 2,8-NPA means 2,8-naphthalene dicarboxylic acid; 1,5-NPA means 1,5-naphthalene dicarboxylic acid; 1,4-NPA means 1,4-naphthalene dicarboxylic acid; and 1,8-NPA means 1,8-naphthalene dicarboxylic acid.

As to the synthesis of the polycondensed ester for use in the present invention, the polycondensed ester can be easily synthesized in a usual manner either by a heat-melting condensation method using a polyesterification or transesterification reaction of the dicarboxylic acid, the diol and, if desired, a monocarboxylic acid or monoalcohol for end capping or by an interfacial condensation reaction of acid chlorides of these acids with glycols. Details of these polyester-based plasticizers are described in Koichi Murai (compiler), Kaso-zai Sono Riron to Oyo (Plasticizers, and Theory and Application Thereof) (Saiwai Shobo, 1st edition, published on Mar. 1, 1973). Furthermore, the materials described, for example, in JP-A-05-155809, JP-A-05-155810, JP-A-05-197073, JP-A-2006-259494, JP-A-07-330670, JP-A-2006-342227 and JP-A-2007-003679 can also be used.

The amount added of the polycondensed ester plasticizer for use in the present invention is preferably from 0.1 to 70 mass %, more preferably from 1 to 65 mass %, and most preferably from 3 to 60 mass %, based on the amount of the cellulose acylate.

The content of the starting materials and the side products in the polycondensation-ester plasticizer, concretely aliphatic diols, dicarboxylates, diol esters and others, that may be in the film is preferably less than 1%, more preferably less than 0.5%. The dicarboxylate includes dimethyl phthalate, di(hydroxyethyl) phthalate, dimethyl terephthalate, di(hydroxyethyl) terephthalate, di(hydroxyethyl) adipate, di(hydroxyethyl) succinate, etc. The diol ester includes ethylene diacetate, propylene diacetate, etc.

As the plasticizer for the polymer film of the invention, also preferred is a methyl methacrylate (MA) oligomer plasticizer. The MA oligomer plasticizer may be combined with the above-mentioned saccharide plasticizer for use herein. In the mode of combination use, the ratio by mass of the MA oligomer plasticizer to the saccharide plasticizer is preferably from ½ to ⅕, more preferably from ⅓ to ¼. Examples of the MA-oligomer plasticizer include oligomers having a repeating unit shown below.

[Chem. 156]

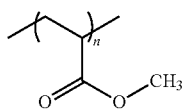

The weight-averaged molecular weight is preferably from about 500 to about 2000, more preferably from about 700 to about 1500; and more preferably from about 800 to about 1200.

Examples of the MA-oligomer plasticizer include both of oligomers of MA alone and oligomers having other repeating unit (s) along with the representing unit derived from MA. Examples of the other repeating unit (s) include any units derive from ethyl acrylate, i- or n-propyl acrylate, n-, s- or t-butyl acrylate, n-, i- or s-pentyl acrylate, n- or i-hexyl acrylate, n- or i-heptyl acrylate, n- or i-octyl acrylate, n- or i-nonyl acrylate, n- or i-myristyl acrylate, 2-ethylhexyl acrylate, ε-caprolactam acrylate, 2-hydroxyethyl acylate, 2-hydroxypropyl acrylate, 3-hydroxypropyl acrylate,4-hydroxybutyl acrylate, 2-hydroxybutyl acrylate, 2-methoxyethyl acrylate, 2-ethoxyethyl acrylate and methacrylates formed by replacing acrylic acid in the acrylates with methacrylic acid. Monomers having an aromatic ring(s) such as styrene, methyl styrene and hydroxy styrene may be used. As the other monomer(s), acrylate monomer(s) or methacrylate monomer(s), having no aromatic ring, are preferable.

The MA-oligomer plasticizer, having two or more repeating units derived from X which is a monomer having a hydrophilic group(s) and from Y which is a monomer having no hydrophilic group, may be used. Among such oligomers, those having a molar ratio of X to Y, X/Y, of from 1/1 to 1/99 are preferable.

The MA-oligomer may be prepared in reference to the method described in JP-A No. 2003-12859.

(Polymer Plasticizer)

The polymer film of the invention may contain any other polymer plasticizer along with or in place of any one of the above-mentioned saccharide plasticizer, polycondensate ester plasticizer and MA oligomer plasticizer. The other polymer plasticizer includes polyester-polyurethane plasticizers, aliphatic hydrocarbon polymers, alicyclic hydrocarbon polymers; vinylic polymers such as polyvinyl isobutyl ether, poly-N-pyrrolidone, etc.; styrenic polymers such as polystyrene, poly-4-hydroxystyrene, etc.; polyethers such as polyethylene oxide, polypropylene oxide, etc.; polyamides, polyurethanes, polyureas, phenol-formaldehyde condensates, urea-formaldehyde condensates, polyvinyl acetate, etc.

(Compound Having at Least Two Aromatic Rings)

The polymer film of the invention may contain a compound having at least 2 aromatic rings. The compound has an effect of controlling the optical properties of the cellulose ester film. For example, when the cellulose ester film of the invention is sued as an optical compensation film, it is effectively stretched for controlling the optical properties, especially Re thereof to be on a desired level. For increasing Re thereof, the in-plane refractive anisotropy of the film may be increased, for which one method comprises regulating the main chain orientation by stretching. As combined with stretching, a compound having a large refractivity anisotropy may be added to the film for further increasing the refractive anisotropy of the film. For example, when the film to which a compound having at least 2 aromatic ring is added as an additive thereto is stretched, the main chain of the polymer constituting the film is oriented, and with that, the compound itself becomes well orientable and the film may be controlled to have desired optical properties with ease.

The compound having at least 2 aromatic rings includes, for example, triazine compounds as in JP-A 2003-344655, rod-shaped compounds as in JP-A 2002-363343, crystalline compounds as in JP-A 2005-134884 and 2007-119737, etc. More preferred are triazine compounds and rod-shaped compounds. Two or more different types of compounds having at least 2 aromatic rings may be used, as combined. The molecular weight of the compound having at least 2 aromatic rings is preferably from 300 to 1200 or so, more preferably from 400 to 1000.

The mass percent of the compound having at least two aromatic rings to the cellulose acylate resin is preferably 0.05% to 10%, more preferably 0.5% to 8%, and most preferably 1% to 5%. The compound having two aromatic rings may also function as the compound represented by Formula (1) or (2) that is used in the present invention. However, if a compound having two aromatic rings has a 1,3,5-triazine ring structure but does not satisfy Formulae (1) and (2), the mass percent of the compound having two aromatic rings to the cellulose acylate resin ranges preferably from 0.05% to 10%, more preferably from 0.5% to 8%, and most preferably from 1% to 5%, from the viewpoint of reducing the humidity dependency.

(Optical Anisotropy-Controlling Agent)

An optical anisotropy-controlling agent may be added to the polymer film. For example, its examples include "Rth-reducing compounds" described in JP-A 2006-30937, pp. 23-72.

(Mat Agent Fine Particles)

The polymer film of the invention may contain fine particles as a mat agent. The fine particles usable in the invention are silicon dioxide, titanium dioxide, aluminium oxide, zirconium oxide, calcium carbonate, talc, clay, calcined kaolin, calcined calcium silicate, calcium silicate hydrate, aluminium silicate, magnesium silicate, and calcium phosphate. Preferably, the fine particles contain silicon as they are effective for reducing the haze of films. Especially preferably, they are silicon dioxide.

The silicon dioxide microparticles may be commercially available products such as Aerosils R972, R972V, R974, R812, 200, 200V, 300, R202, OX50, and TT600 (manufactured by Nippon Aerosil Co., Ltd.). Zirconium oxide microparticles that can be used are, for example, commercially available Aerosils R976 and R811 (manufactured by Nippon Aerosil Co., Ltd.).

A polymer film containing particles having a small average secondary particle diameter can be produced with a dispersion of microparticles. In a cellulose acylate film as an example, several processes are known for preparing a dispersion of microparticles. For example, a microparticle dispersion can be prepared by mixing a solvent and microparticles with stirring to prepare a microparticle dispersion in advance, adding this microparticle dispersion to a small amount of separately prepared cellulose acylate solution and stirring the mixture to prepare a solution, and further mixing the solution with a cellulose acylate dope solution as a main component. This process is preferable in that the dispersibility of silicon dioxide microparticles is high and that the silicon dioxide microparticles hardly re-aggregate. Alternatively, a microparticle dispersion can be prepared by adding a small amount of cellulose acylate to a solvent and stirring the mixture to prepare a solution, adding microparticles to the solution and dispersing the mixture with a disperser to prepare a microparticle-containing solution, and sufficiently mixing the microparticle-containing solution with a dope solution with an in-line mixer. Any of these processes can be employed, and any other process may be employed without limitation.

The solvent used in the preparation process described above can be lower alcohol. Preferred examples of the lower alcohol include methanol, ethanol, propanol, isopropanol, and butanol. Any other solvent can be used as well as lower alcohol, and preferred examples of the solvent are those used information of a film from cellulose acylate.

(Low-Molecular Plasticizer, Degradation Inhibitor, Release Agent)

Various additives (e.g., low-molecular plasticizer, UV inhibitor, degradation inhibitor, release agent, IR absorbent, etc.) may be added to the polymer film in the process of producing the film, depending on the applications of the film. The additives may be solid or oily, or that is, they are not specifically defined in point of their melting point and boiling point thereof. For example, for the additive, UV absorbents at 20 degrees Celsius or lower and at 20 degrees Celsius or higher may be mixed, or plasticizers may also be mixed in the same manner. For example, these are described in JP-A 201-151901. IR absorbent dyes are described in, for example, JP-A 2001-194522. The time at which the additive is added may be in any stage in the step of dope preparation; however, the additive may be added in the final stage of the dope preparation step. Not specifically defined, the amount of the material to be added may be any one capable expressing the function thereof. In case where the cellulose ester film is formed of plural layers, then the type and the amount of the additive to be added to the constitutive layers may differ. For example, as in JP-A 2001-151902, the related technique is known in the art. Regarding the details of the additives, the materials described in Hatsumei Kyokai Disclosure Bulletin No. 2001-1745 (published in Mar. 15, 2001 by Hatsumei Kyokai) in p.p. 16-22 are preferred for use in the invention.

(1-5) Production Method for Polymer Film:

The polymer film of the invention is preferably produced according to a solvent-casting method. According to a solvent-casting method, a dope prepared by dissolving a polymer in an organic solvent is cast onto the surface of a support of a metal or the like, and dried thereon to form a film. Next, the film is peeled away from the support surface, and stretched.

The cellulose acylate film is preferably produced according to a solvent-casting method. Examples of production of cellulose ester film according to a solvent-casting method are given in U.S. Pat. Nos. 2,336,310, 2,367,603, 2,492,078, 2,492,977, 2,492,978, 2,607,704, 2,739,069 and 2,739,070, British Patents 640731, 736892, JP-B 45-4554, 49-5614, and JPA Nos. syo 60-176834, syo 60-203430, and syo 62-115035, and their descriptions are referred to herein. The cellulose acylate film may be stretched. Regarding the method and condition for stretching treatment, for example, referred to are JPA Nos. syo 62-115035, hei 4-152125, hei 4-284511, hei 4-298310, and hei 11-48271.

(1-6) Characteristics of Polymer Film: (Re and Rth)

The preferred range of the optical characteristics of the polymer film of the invention changes depending on the use of the film. In an embodiment where the film is used in a VA-mode liquid-crystal display device, preferably, its Re(589) is from 30 nm to 200 nm, and its Rth(589) is from 70 nm to 400 mm; more preferably, its Re(589) is from 30 nm to 150 nm, and its Rth(589) is from 100 nm to 300 nm; even more preferably, its Re(589) is from 40 nm to 100 nm, and its Rth(589) is from 100 nm to 250 nm.

The Re and Rth of a film are measured after leaving the film under an environment of a temperature of 25° C. and a relative humidity of 60% for a sufficient time (more than 2 hours, e.g., 12 hours or 24 hours) at the same temperature and the same relative humidity, unless otherwise specified.

(Humidity Dependency of Re and Rth)

The polymer film of the present invention is characterized by a small fluctuation in Re and/or Rth depending on humidity, specifically, a small fluctuation between the Re (also referred to as Re [25° C., RH10%]) of a film humidified at a relative humidity of 10% at 25° C. for 2 hours and the Re (also referred to as Re [25° C., RH80%]) of the film humidified at a relative humidity of 80% at 25° C. for 2 hours and/or a small fluctuation between the Rth (also referred to as Rth [25° C., RH10%]) of the film humidified at a relative humidity of 10% at 25° C. for 2 hours and the Rth (also referred to as Rth [25° C., RH80%]) of the film humidified at a relative humidity of 80% at 25° C. for 2 hours. The film of the present invention has reduced humidity dependency of optical characteristics to suppress the fluctuations in Re and Rth even under a humidity-varying environment and thereby can have retardation in a preferred range.

In the polymer film of the present invention, the humidity dependency of Re ($\Delta Re=|Re [25° C., RH10\%]-Re [25° C., RH80\%]|$) is preferably 10 nm or less, more preferably 9 nm or less, and most preferably 8 nm or less.

In the polymer film of the present invention, the humidity dependency of Rth ($\Delta Rth=|Rth [25° C., RH10\%]-Rth [25° C., RH80\%]|$) is preferably 21 nm or less, more preferably 20 nm or less, and most preferably 19 nm or less.

(Film Thickness)

In an embodiment where the polymer film of the invention is used as a part in a device that is desired to have a thinned body, for example, as a part of a liquid-crystal display device or the like, the film is preferably thinner. However, if too thin, the film could not exhibit the optical characteristics necessary for the use. In an embodiment where the film of the invention is used as an optical compensatory film in a liquid-crystal display device, or as a protective film for a polarizer, the film thickness is preferably from 20 to 80 µm or so, more preferably from 25 to 70 µm or so, even more preferably from 30 to 60 µm or so.

3. Application of Polymer Film

The polymer film of the present invention can be used in various applications. For example, the polymer film can be used as a retardation film (hereinafter, also referred to as an optical compensation film) of a liquid crystal display or as a protective film of a polarizing plate.

(Retardation Film)

The polymer film of the present invention can be used as a retardation film. "A retardation film or an optical compensation film" is usually used in a display such as a liquid crystal display and is an optical material having optical anisotropy and is synonymous with, for example, an optically compensatory sheet. In a liquid crystal display, the optical compensation film is used for improving the contrast of the display screen or improving the viewing angle characteristics or the tint.

In order to obtain desired Re and Rth levels, a plurality of the polymer films of the present invention may be laminated, or the polymer film of the present invention may be laminated another film. The films can be laminated with an adhesive or a bonding agent.

(Polarizing Plate)

The polymer film of the invention may be used as a protective film for polarizing plate, and the invention provides a polarizing plate comprising the film. One example of the polarizing plate of the invention comprises a polarizing film and two protective films (transparent films) for protecting both surfaces of the polarizing film, in which the cellulose ester film of the invention is used as at least one of the polarizer-protective films. In an embodiment where the cellulose ester film of the invention is used as a support and an optically-anisotropic layer of a liquid-crystal composition is formed on the surface of the support, and where the cellulose ester film is used as a protective film for a polarizing plate, it is desirable that the back side (on which the optically-anisotropic layer is not formed) of the polymer film of the invention serving as a support is stuck to the surface of the polarizing film.

In case where the polymer film of the invention is used as a protective film for the polarizing plate, the polymer film of the invention is preferably hydrophilicated through the above-mentioned surface-treatment (e.g., as described in JP-A 6-94915 and 6-118232), and for example, the film is preferably processed for glow discharge treatment, corona discharge treatment, or alkali saponification. In particular, the surface treatment of the film is most preferably alkali saponification.

As the polarizing film, for example, usable is a film produced by dipping a polyvinyl alcohol film in an iodine solution and stretching it. In case where the polarizing film produced by dipping a polyvinyl alcohol film in an iodine solution and stretching it is used, the surface-treated surface of the transparent cellulose ester film of the invention may be directly stuck to both surfaces of the polarizing film with an adhesive. In the production method of the invention, it is desirable that the polymer film is directly stuck to the polarizing film in the manner as above. As the adhesive, usable is an aqueous solution of polyvinyl alcohol or poly-vinyl acetal (e.g., polyvinyl butyral) or a latex of a vinylic polymer (e.g., polybutyl acrylate). Especially preferred as the adhesive is an aqueous solution of a completely-saponified polyvinyl alcohol.

In general, in a liquid-crystal display device, a liquid-crystal cell is disposed between two polarizing plates. Therefore, the device has four polarizer-protective films. The polymer film of the invention may be used as any of those four polarizer-protective films, but the polymer film of the invention is especially useful as the protective film to be disposed between the polarizing film and the liquid-crystal layer (liquid-crystal cell) in the liquid-crystal display device. As the protective film to be disposed on the side of the polarizing film opposite to the side of the polymer film of the invention, a transparent hard coat layer, an antiglare layer, an antireflection layer or the like may be disposed, and in particular, the film of the invention is favorable as the polarizer-protective film to be disposed as the outermost surface layer on the display panel side of the liquid-crystal display device.

(Liquid-Crystal Display Device)

The polymer film of the invention and the optically-compensatory film and the polarizing plate comprising the film can be used in various display modes of liquid-crystal display devices. Various liquid-crystal modes where the film of the invention can be used are described. Above all, the polymer film of the invention and the optically-compensatory film and the polarizing plate comprising the film are favorably used in VA-mode liquid-crystal display devices. The liquid-crystal display devices may be any of transmission-mode, reflection-mode or semitransmission-mode devices.

FIG. 1 shows a schematic cross-sectional view of one example of a liquid-crystal display device of the invention. In FIG. 1, the upper side is a viewers' side (panel side), and the lower side is a backlight side.

The VA-mode liquid-crystal display device of in FIG. 1 comprises a liquid-crystal cell LC (comprising an upper substrate 1, a lower substrate 3 and a liquid-crystal layer 5), and a pair of an upper polarizing plate P1 and a lower polarizing plate P2 disposed to sandwich the liquid-crystal cell LC therebetween. In general, polarizing films are incorporated into the liquid-crystal display device as polarizing plates having a protective film on both surfaces thereof; however, in FIG. 1, the outer protective film of the polarizing film is omitted. The polarizing plates P1 and P2 each have a polarizing film 8a and 8b, respectively; and they are so disposed that the absorption axes 9a and 9b thereof are perpendicular to each other. The liquid-crystal cell LC is a VA-mode liquid-crystal cell, and at the time of black level of display, the liquid-crystal layer 5 is in homeotropic alignment as in FIG. 1. The upper substrate 1 and the lower substrate 3 each have an alignment film (not shown) and an electrode layer (not shown) on the inner surface thereof; and the substrate 1 has a color filter layer (not shown) on the viewers' side inner surface thereof.

Between the upper substrate 1 and the upper polarizing film 8a, and between the lower substrate 3 and the lower polarizing film 8b, disposed are retardation films 10a and 10b, respectively. The retardation films 10a and 10b are polymer films of the invention. The retardation films 10a and 10b are so disposed that the in-plane slow axes 11a and 11b thereof could be perpendicular to the absorption axes 9a and 9b of the upper polarizing film 8a and the lower polarizing film 8b, respectively. Specifically, the retardation films 10a and 10b are so disposed that their slow axes are perpendicular to each other. The retardations films 10a and 10b each comprising the polymer film of the invention contribute toward reducing the light leakage and the color shift that may occur in oblique directions at the time of black level of display.

(Hard Coat Film, Antiglare Film, Antireflection Film)

The polymer film of the invention may be applied to a hard coat film, an antiglare film, or an antireflection film, as the case may be. For the purpose of enhancing the visibility of flat panel displays such as LCD, PDP, CRT, EL and the like, any or all of a hard coat layer, an antiglare layer and an antireflection layer may be given to one or both surfaces of the transparent polymer film of the invention. Preferred embodiments of such antiglare film and antireflection film are described in detail in Hatsumei Kyokai Disclosure Bulletin (No. 2001-1745, published on Mar. 15, 2001 by Hatsumei Kyokai), pp. 54-57, and are favorably applicable to the cellulose ester film of the invention.

EXAMPLES

The characteristic features of the invention are described more concretely with reference to the following Examples and Comparative Examples. In these Examples, the material used, its amount and the ratio, the details of the treatment and the treatment process may be suitably modified or changed not overstepping the sprit and the scope of the invention. Accordingly, the invention should not be limitatively interpreted by the Examples mentioned below.

Example 1a

Synthetic Example of Compound in Compound Group A Represented by Formula (1)

Synthetic Example 1a-1

Synthesis-1 of Compound (1-2)

2,4-Diamino-6-methylpyrimidine was synthesized in accordance with the process described in Aust. J. Chem., 1984, vol. 37, pp. 1195-1201.

Guanidine hydrochloride (23.8 g) was added to methanol (50 mL) and a solution of sodium methoxide in 28% methanol (51 mL), followed by stirring at room temperature for 30 minutes. Subsequently, the precipitated salt was removed by filtration, followed by concentration under reduced pressure to give a guanidine-free product solution. Then, 3-amino crotononitrile (16.4 g) and 1-butanol (60 mL) were added to the solution. The reaction solution was stirred with heating at 110° C. for 10 hours under a nitrogen gas flow. After completion of the reaction, the precipitated salt was removed by hot filtration, and 100 mL of acetone was added to the remaining solution, followed by stirring under ice cooling for 30 minutes to give a crude product. The crude product was recrystallized from acetone to yield 10.5 g of 2,4-diamino-6-methylpyrimidine.

Methyl benzoate (23 g: 169 mmol) and sodium methoxide (22 g: 407 mmol) were added to a solution of 2,4-diamino-6-methylpyrimidine (10 g: 81 mmol) in N-ethylpyrrolidone (100 mL), followed by stirring with heating at 40° C. for 2 hours. The temperature of the reaction system was decreased to room temperature. The reaction solution was poured into a 1N aqueous hydrochloric acid solution, and the solid component was collected by filtration. The crude product was recrystallized from 2-propanol to yield compound (1-2).

The NMR spectrum of produced compound (1-2) is as follows.

$^1$H-NMR (solvent: d6-DMSO, standard: tetramethylsilane) δ (ppm) 2.50 (3H, s) 7.45-7.70 (6H, m) 7.90 (1H, s) 7.95-8.05 (4H, m) 10.88 (1H, s) 11.10 (1H, s)

Synthetic Example 1a-2

Synthesis-2 of Compound (1-2)

2,4-Diamino-6-methylpyrimidine (2 g: 16 mmol) and phenyl benzoate were mixed in xylene, followed by reflux heating for 6 hours. HPLC confirmed that the yield of compound (1-2) was 60%.

Synthetic Example 2a

Synthesis of Compound (1-8)

The compound was synthesized as in Synthetic example 1a-1 except that 2,4-diamino-6-hydroxypyrimidine was used as a starting material in place of 2,4-diamino-6-methylpyrimidine in Synthetic example 1a-1. The reaction solution was poured into an aqueous acetic acid solution, followed by adjusting the solution to pH 6. The precipitated solid was collected by filtration and was washed with acetonitrile and methanol with heating to yield compound (1-8).

The NMR spectrum of produced compound (1-8) is as follows.

$^1$H-NMR (solvent: d6-DMSO, standard: tetramethylsilane) δ (ppm) 6.88 (1H, s) 7.48-7.68 (4H, m) 7.92 (2H, d) 8.01 (2H, d) 10.36 (1H, s) 11.64 (1H, s) 12.11 (1H, s)

Synthetic Example 3a-1

Synthesis-1 of Compound (1-9)

The compound was synthesized as in Synthetic example 1a-1 except that 2, 4-diamino-6-methoxypyrimidine was used as a starting material in place of 2,4-diamino-6-methylpyrimidine in Synthetic example 1a-1 and that the following processes were performed.

2,4-Diamino-6-methoxypyrimidine was synthesized in accordance with the method described in J. Bioorg. Med. Chem., 1998, vol. 6, pp. 1057-1067 and was used without purification for the subsequent step.

2,4-Diamino-6-chloropyrimidine (21.9 g: 150 mmol) was added to methanol (20 mL) and toluene (80 mL) under a nitrogen gas flow, and a solution of sodium methoxide in 28% methanol (153 mL) was dropwise added thereto at room temperature. Subsequently, the mixture was refluxed in a hot water bath at 80° C. while the solvent was being distilled off by a Dean-Stark trap. During the reflux, toluene (60 mL) was added to the reaction solution, followed by refluxing. The reaction system was cooled to 50° C., and a mixture of N-ethylpyrrolidone (60 mL) and methyl benzoate (53 g: 485 mol) was added thereto, followed by stirring with heating at 45° C. for 3 hours. The temperature of the reaction system was decreased to room temperature, and then the reaction solution was added to a liquid mixture of toluene (200 mL), water (200 mL), and acetic acid (43 mL). The organic layer was separated, and 150 mL of 1N aqueous acetic acid solution was added thereto under heating for separation. This separation step was repeated twice, and water (200 mL) was added to the organic layer, followed by cooling to room temperature to precipitate the product. The crude product was recrystallized from acetonitrile to yield 30 g (yield: 57%) of compound (1-9).

The NMR spectrum of produced compound (1-9) is as follows.

$^1$H-NMR (solvent: d6-DMSO, standard: tetramethylsilane) δ (ppm) 3.90 (3H, s) 7.39 (1H, s) 7.45-7.70 (6H, m) 7.90-8.05 (4H, m) 10.78 (1H, s) 11.00 (1H, s)

Synthetic Example 3a-2

Synthesis-2 of Compound (1-9)

2,4-Diamino-6-chloropyrimidine (17.34 g: 120 mmol) and sodium methoxide (38.9 g) were sequentially added to t-butanol (60 mL) and N-ethylpyrrolidone (30 mL) under a nitrogen gas flow, followed by stirring with heating at 80° C. for 2 hours. The reaction solution was cooled to 60° C., and methyl benzoate (38.9 g: 288 mol) was dropwise added thereto, followed by stirring with heating at 60° C. for 2 hours. The reaction solution was added to a liquid mixture of iced water (130 mL) and concentrated hydrochloric acid (51 mL), followed by heating to 50° C. to completely dissolve the solid component. The organic layer was separated, and methanol (100 mL) and water (100 mL) were added thereto, followed by stirring under ice cooling for 1 hour. The precipitated product was collected by filtration, and the resulting crystals were washed with a poured methanol/water solvent mixture and then water. After ventilation drying at 50° C. for 13 hours, 38 g (yield: 85%) of compound (1-9) was yielded.

Synthetic Example 3a-3

Synthesis-3 of Compound (1-9)

The crystals (5 g) prepared in Synthetic example 3a-1 were dispersed in acetonitrile/water (30 mL/20 mL), followed by stirring at room temperature for 2 hours. The precipitated solid was collected by filtration to yield compound (1-9) having a different water content ratio.

Synthetic Example 3a-4

Synthesis-4 of Compound (1-9)

The crystals prepared in Synthetic example 3a-2 in a molten state were dried at 150° C. under reduced pressure for 3 hours, followed by quenching to yield amorphous compound (1-9). The water content ratio of the resulting compound immediately after the drying was less than 0.5%.

Synthetic Example 3a-5

Synthesis-5 of Compound (1-9)

The crystals (3.5 g) prepared in Synthetic example 3a-1 were dissolved in ethyl acetate (20 mL), and concentrated hydrochloric acid (1 mL) was added thereto, followed by stirring at room temperature for 1 hour. The precipitated hydrochloride was collected by filtration.

The NMR spectrum of produced compound (1-9) is as follows.

$^1$H-NMR (solvent: d6-DMSO, standard: tetramethylsilane) δ (ppm) 3.96 (3H, s) 6.8 (1H, br) 7.39 (1H, s) 7.50-7.68 (6H, m) 7.99 (2H, m) 8.08 (2H, m) 11.4 (1H, br) 11.6 (1H, br)

Synthetic Example 3a-6

Synthesis-6 of Compound (1-9)

The crystals prepared in Synthetic example 3a-1 were recrystallized from various solvents to yield crystals having different water content ratio and different solvent content ratio as shown in the following table.

TABLE 3

| Example of recrystallization | Recrystallization solvent | Water content ratio | Solvent content ratio | Collection rate |
|---|---|---|---|---|
| 1 | Methanol | 5.0% | Contain methanol | 57% |
| 2 | Heptane/isopropanol (2/1) | 3.1% | Contain isopropanol | 87% |
| 3 | t-Butanol | 0.4% | Contain t-butanol | 100% |

Synthetic Example 4a

Synthesis of Compound (2-1)

The compound was synthesized as in Synthetic example 1a-1 except that 2,4-diaminopyrimidine and methyl m-methylbenzoate were used as starting materials in place of 2,4-diamino-6-methylpyrimidine and methyl benzoate, respectively, in Synthetic example 1a-1.

The NMR spectrum of produced compound (2-1) is as follows.

$^1$H-NMR (solvent: d6-DMSO, standard: tetramethylsilane) δ (ppm) 2.38 (6H, s) 7.35-7.50 (4H, m) 7.74-7.90 (4H, m) 7.98 (1H, s) 8.67 (1H, s) 10.84 (1H, s) 11.10 (1H, s)

Synthetic Example 5a

Synthesis of Compound (2-2)

The compound was synthesized as in Synthetic example 1a-1 except that methyl m-methylbenzoate was used in place of methyl benzoate in Synthetic example 1a-1 and that the following processes were performed.

Methyl m-methylbenzoate (72.5 g: 485 mmol) and sodium methoxide (35 g: 650 mmol) were added to a solution of 2,4-diamino-6-methylpyrimidine (20 g: 161 mmol) in N-ethylpyrrolidone (140 mL), followed by stirring with heating at 40° C. for 3 hours. The temperature of the reaction system was decreased to room temperature, and the reaction solution was added to a liquid mixture of water (190 mL), concentrated hydrochloric acid (72.5 mL), and ethyl acetate (50 mL), under ice cooling. The resulting solid (hydrochloride of compound (2-2)) was collected by filtration. The hydrochloride was added to saturated aqueous sodium bicarbonate solution (160 mL) and ethyl acetate (150 mL), followed by stirring with heating for dissolution. The resulting solution was cooled to room temperature to precipitate the product. The crude product was collected by filtration and was recrystallized from acetonitrile to yield 47 g (yield: 81%) of compound (2-2).

The NMR spectrum of produced compound (2-2) is as follows.

$^1$H-NMR (solvent: d6-DMSO, standard: tetramethylsilane) δ (ppm) 2.38 (6H, s) 2.50 (3H, s) 7.36-7.47 (4H, m) 7.70-7.90 (5H, m) 10.77 (1H, s) 10.99 (1H, s)

Synthetic Example 5a-2

Synthesis-2 of Compound (2-2)

2,4-Diamino-6-methylpyrimidine (2.4 g: 20 mmol), triethylamine (6.97 mL), and THF (20 mL) were mixed, and m-methylbenzoyl chloride (7.7 g: 50 mmol) was dropwise added thereto at room temperature, followed by stirring with heating at 40° C. for 6 hours. After cooling, the product was extracted with ethyl acetate and was recrystallized from ethyl acetate/hexane to yield 2.1 g of compound (2-2).

Synthetic Example 6a

Synthesis of Compound (2-4)

The compound was synthesized as in Synthetic example 1a-1 except that 2,4-diamino-6-methylaminopyrimidine and methyl m-methylbenzoate were used as starting materials in place of 2,4-diamino-6-methylpyrimidine and methyl benzoate, respectively, in Synthetic example 1a-1.

The NMR spectrum of produced compound (2-4) is as follows.

$^1$H-NMR (solvent: d6-DMSO, standard: tetramethylsilane) δ (ppm) 2.35 (6H, s) 2.81 (3H, s) 7.15 (1H, s) 7.30-7.43 (5H, m) 7.65-7.85 (4H, m) 10.22 (1H, s) 10.38 (1H, s)

Synthetic Example 7a

Synthesis of Compound (2-8)

The compound was synthesized as in Synthetic example 1a-1 except that 2,4-diamino-6-hydroxypyrimidine and methyl m-methylbenzoate were used as starting materials in place of 2,4-diamino-6-methylpyrimidine and methyl benzoate, respectively, in Synthetic example 1a-1.

The NMR spectrum of produced compound (2-8) is as follows.

$^1$H-NMR (solvent: d6-DMSO, standard: tetramethylsilane) δ (ppm) 2.41 (6H, s) 6.89 (1H, s) 7.36-7.53 (4H, m) 7.70-7.88 (4H, m) 10.23 (1H, s) 11.54 (1H, s) 11.99 (1H, s)

Synthetic Example 8a

Synthesis of Compound (2-9)

The compound was synthesized as in Synthetic example 1a-1 except that 2,4-diamino-6-methoxypyrimidine and methyl m-methylbenzoate were used as starting materials in place of 2,4-diamino-6-methylpyrimidine and methyl benzoate, respectively, in Synthetic example 1a-1. The crude product was purified by silica gel column chromatography using ethyl acetate/n-hexane and recrystallized from ethyl acetate/n-hexane to yield compound (2-9).

The NMR spectrum of produced compound (2-9) is as follows.

$^1$H-NMR (solvent: d6-DMSO, standard: tetramethylsilane) δ (ppm) 2.40 (6H, s) 3.92 (3H, s) 7.35-7.45 (5H, m) 7.73-7.87 (4H, m) 10.67 (1H, s) 10.88 (1H, s)

Synthetic Example 8a-2

Synthesis-2 of Compound (2-9)

2,4-Diamino-6-methoxypyrimidine (2.2 g: 20 mmol) was mixed with m-methylbenzoyl chloride (4.56 g: 50 mmol) and sodium bicarbonate (4.2 g) in acetonitrile, followed by reflux heating for 6 hours. After cooling, the precipitated solid was collected by filtration, washed by dispersion in water, collected by filtration again, and washed with poured water and acetonitrile to yield 2.1 g of compound (2-9).

Synthetic Example 9a

Synthesis of compound (5-1), (5-2), (5-7), and (5-8)

Compounds (5-1), (5-2), (5-7), and (5-8) were prepared as in Synthetic example 1a-1 except that methyl p-methylbenzoate, methyl o-methylbenzoate, methyl m-methoxybenzoate, and methyl p-methoxybenzoate were respectively used as starting materials in place of methyl benzoate and that the reaction was performed using sodium methoxide. Purification was performed by silica gel column chromatography and recrystallization.

Synthetic Example 10a

Synthesis of Compound (6-13)

2-Amino-4-anilino-6-methoxypyrimidine was synthesized using 2-amino-4,6-dichloropyrimidine as a starting material through 2-amino-4-chloro-6-methoxypyrimidine. A solution of sodium methoxide in 28% methanol (43 mL) at an internal temperature of 20° C. or less was dropwise added to a mixture of 2-amino-4,6-dichloropyrimidine (32.8 g) and acetone (700 mL) under ice cooling. The reaction was further continued at an internal temperature of 40° C. for 4 hours, and the solution was concentrated under reduced pressure, followed by addition of 500 mL of water. The precipitated solid was collected by filtration and was used without purification for the subsequent step. The crude product of 2-amino-4-chloro-6-methoxypyrimidine, aniline (26.7 mL), methoxyethanol (150 mL), and hydrochloric acid (0.2 mL) were mixed, followed by stirring with heating at 120° C. for 3 hours. After cooling, the reaction solution was added to aqueous sodium bicarbonate (500 mL)/ethyl acetate under ice cooling to extract the product with ethyl acetate. After the concentration, purification by column chromatography (ethyl acetate/n-hexane) was performed to yield 14 g of 2-amino-4-anilino-6-methoxypyrimidine.

2-Amino-4-anilino-6-methoxypyrimidine was synthesized as in Synthetic example 1a-1 with methyl m-methylbenzoate and sodium methoxide. The crude product was purified by silica gel column chromatography using methylene chloride/methanol and was recrystallized from methylene chloride/n-hexane to yield compound (6-13).

The NMR spectrum of produced compound (6-13) is as follows.

$^1$H-NMR (solvent: d6-DMSO, standard: tetramethylsilane) δ (ppm) 2.39 (3H, s) 3.85 (3H, s) 5.87 (1H, s) 6.95 (1H, s) 7.23-7.30 (2H, m) 7.38-7.41 (2H, m) 7.72-7.85 (4H, m) 9.40 (1H, s) 9.46 (1H, s)

Synthetic Example 11a

Synthesis of Compound (6-14)

2-Amino-4-anilino-6-methylaminopyrimidine was synthesized, via 2-amino-4-chloro-6-methylaminopyrimidine, with 2-amino-4,6-dichloropyrimidine as a starting material. 2-Amino-4,6-dichloropyrimidine (32.8 g), a 40% aqueous methylamine solution (34.5 mL), and ethanol (300 mL) were mixed, followed by stirring at an internal temperature of 70°

C. for 4 hours. Subsequently, the solvent was concentrated under reduced pressure, and crystallization from acetonitrile was performed. The product was collected by filtration and was used without purification for the subsequent step. The crude product of 2-amino-4-chloro-6-methylaminopyrimidine, aniline (27.4 mL), methoxyethanol (100 mL), and hydrochloric acid (0.2 mL) were mixed, followed by stirring with heating at 120° C. for 3 hours. After cooling, the reaction solution was added to sodium bicarbonate water (500 mL)/ethyl acetate under ice cooling to extract the product with ethyl acetate. After concentration, purification by column chromatography (ethyl acetate/methanol) was performed to yield 18 g of 2-amino-4-anilino-6-methylaminopyrimidine. Synthesis was performed as in Synthetic example 1a-1 with 2-amino-4-anilino-6-methylaminopyrimidine, methyl m-methylbenzoate, and sodium methoxide. The product was purified by silica gel column chromatography using ethyl acetate/n-hexane and recrystallization from ethyl acetate/n-hexane to yield compound (6-14).

The NMR spectrum of produced compound (6-14) is as follows.

$^1$H-NMR (solvent: d6-DMSO, standard: tetramethylsilane) δ (ppm) 2.37 (3H, s) 2.75 (3H, d) 5.51 (1H, s) 6.87-6.91 (1H, m) 7.15-7.24 (2H, m) 7.34-7.38 (2H, m) 7.65-7.74 (4H, m) 8.95 (1H, s) 10.02 (1H, s)

Synthetic Example 12a

Synthesis of Compound (6-15)

The compound was synthesized as in Synthetic example 1a-1 except that 2,4-diamino-6-hydroxypyrimidine and methyl p-tert-butylbenzoate were used as starting materials in place of 2,4-diamino-6-methylpyrimidine and methyl benzoate, respectively, in Synthetic example 1a-1.

The NMR spectrum of produced compound (6-15) is as follows.

$^1$H-NMR (solvent: d6-DMSO, standard: tetramethylsilane) δ (ppm) 1.34 (18H, s) 7.87 (1H, s) 7.51-7.63 (4H, m) 7.85-7.95 (4H, m) 10.21 (1H, s) 11.57 (1H, s) 12.07 (1H, s)

Synthetic Example 13a

Synthesis of Compound (6-16)

The compound was synthesized as in Synthetic example 5a except that 2,4-diamino-6-chloropyrimidine and methyl benzoate were used as starting materials in place of 2,4-diamino-6-methylpyrimidine and methyl m-methylbenzoate, respectively, in Synthetic example 5a. The product extracted from aqueous sodium bicarbonate solution/ethyl acetate was collected by filtration, and no purification was performed.

The NMR spectrum of produced compound (6-16) is as follows.

$^1$H-NMR (solvent: d6-DMSO, standard: tetramethylsilane) δ (ppm) 1.34 (18H, s) 7.87 (1H, s) 7.51-7.63 (4H, m) 7.85-7.95 (4H, m) 10.21 (1H, s) 11.57 (1H, s) 12.07 (1H, s)

Synthetic Example 14a

Synthesis of Compound (7-1)

The compound was synthesized as in Synthetic example 1a-1 except that 2,6-diaminopyridine was used as a starting material in place of 2,4-diamino-6-methylpyrimidine in Synthetic example 1a-1.

The NMR spectrum of produced compound (7-1) is as follows.

$^1$H-NMR (solvent: d6-DMSO, standard: tetramethylsilane) δ (ppm) 7.45-7.66 (6H, m) 7.87-7.94 (3H, m) 7.95-8.10 (4H, m) 10.51 (2H, s)

Synthetic Example 15a

Synthesis of Compound (7-2)

The compound was synthesized as in Synthetic example 1a-1 except that 2,6-diaminopyridine and methyl m-methylbenzoate were used as starting materials in place of 2,4-diamino-6-methylpyrimidine and methyl benzoate, respectively, in Synthetic example 1a-1.

The NMR spectrum of produced compound (7-2) is as follows.

$^1$H-NMR (solvent: d6-DMSO, standard: tetramethylsilane) δ (ppm) 2.40 (6H, s) 7.37-7.45 (4H, m) 7.75-7.88 (7H, m) 10.40 (2H, s)

Synthetic Example 16a

Synthesis of Compound (8-1)

Dicyandiamide (18 g: 214 mmol) and nickel (II) acetate (52 g: 209 mmol) were added to a solution of N-(2,5-dimethoxyphenyl)-3-oxobutanamide (50 g: 211 mmol) in N-methylpyrrolidone (150 mL), followed by stirring with heating at 130° C. for 5 hours. The reaction solution was cooled to room temperature and was poured into saturated aqueous sodium bicarbonate, followed by extraction with ethyl acetate. The organic layer was dried over anhydrous sodium sulfate, and the solvent was distilled off with a rotary evaporator. The crude product was washed with 2-propanol to yield compound (8-1).

The NMR spectrum of produced compound (8-1) is as follows.

$^1$H-NMR (solvent: d6-DMSO, standard: tetramethylsilane) δ (ppm) 2.28 (3H, s) 2.71 (3H, s) 2.77 (3H, s) 6.22 (2H, s) 6.40 (2H, s) 6.67 (1H, d) 6.97 (1H, d) 7.59 (1H, s) 9.01 (1H, s)

Synthetic Example 17a

Synthesis of Compound (8-2)

Methyl m-methylbenzoate (17 g: 113 mmol) and sodium methoxide (11 g: 204 mmol) were added to a solution of 2-aminopyrimidine (10 g: 105 mmol) in N-ethylpyrrolidone (100 mL), followed by stirring with heating at 40° C. for 2 hours. The temperature of the reaction system was decreased to room temperature. The reaction solution was poured into a 1N aqueous hydrochloric acid solution, and the solid component was collected by filtration. The crude product was purified by silica gel column chromatography (eluent was methanol: dichloromethane=1:10) to yield compound (8-2).

The NMR spectrum of produced compound (8-2) is as follows.

$^1$H-NMR (solvent: d6-DMSO, standard: tetramethylsilane) δ (ppm) 2.40 (3H, s) 7.25 (1H, t) 7.35-7.44 (2H, m) 7.72-7.84 (2H, m) 8.74 (2H, d) 10.91 (1H, s)

Synthetic Example 18a

Synthesis of Compound (8-3)

The compound was synthesized as in Synthetic example 17a except that 2-amino-4,6-dimethylpyrimidine was used as a starting material in place of 2-aminopyrimidine in Synthetic example 17a.

The NMR spectrum of produced compound (8-3) is as follows.

$^1$H-NMR (solvent: d6-DMSO, standard: tetramethylsilane) δ (ppm) 2.35-2.45 (9H, m) 7.00 (1H, s) 7.35-7.40 (2H, m) 7.73-7.83 (2H, m) 10.72 (1H, s)

Synthetic Example 19a

Synthesis of Compound (8-4)

The compound was synthesized as in Synthetic example 17a except that 2-amino-4,6-dimethoxypyrimidine was used as a starting material in place of 2-aminopyrimidine in Synthetic example 17a.

The NMR spectrum of produced compound (8-4) is as follows.

$^1$H-NMR (solvent: d6-DMSO, standard: tetramethylsilane) δ (ppm) 2.38 (3H, s) 3.88 (6H, s) 5.98 (1H, s) 7.35-7.42 (2H, m) 7.67-7.78 (2H, m) 10.69 (1H, s)

Synthetic Example 20a

Synthesis of Compound (8-5)

Dimethyl isophthalate (7.2 g: 37 mmol) and sodium methoxide (10 g: 185 mmol) were added to a solution of 2-amino-4,6-dimethylpyrimidine (10 g: 81 mmol) in N-ethylpyrrolidone (75 mL), followed by stirring with heating at 40° C. for 2 hours. The temperature of the reaction system was decreased to room temperature. The reaction solution was poured into a 1N aqueous hydrochloric acid solution, and the solid component was collected by filtration. The crude product was recrystallized from acetonitrile to yield compound (8-5).

The NMR spectrum of produced compound (8-5) is as follows.

$^1$H-NMR (solvent: d6-DMSO, standard: tetramethylsilane) δ (ppm) 2.42 (12H, s) 7.04 (2H, s) 7.65 (1H, t) 8.11 (2H, d) 8.52 (1H, s) 10.80 (2H, s)

Synthetic Example 21a

Synthesis of Compound (8-6)

The compound was synthesized as in Synthetic example 1a-1 except that 2,4-diamino-5,6,7,8-tetrahydroquinazoline and methyl m-methylbenzoate were used as starting materials in place of 2,4-diamino-6-methylpyrimidine and methyl benzoate, respectively, in Synthetic example 1a-1.

The NMR spectrum of produced compound (8-6) is as follows.

$^1$H-NMR (solvent: d6-DMSO, standard: tetramethylsilane) δ (ppm) 1.65-1.75 (2H, m) 1.75-1.90 (2H, m) 2.40 (6H, s) 2.47-2.56 (2H, m) 2.80-2.87 (2H, m) 7.35-7.49 (4H, m) 7.71-7.88 (4H, m) 10.72 (1H, s) 10.78 (1H, s)

Synthetic Example 22a-1

Synthesis-1 of Mixture a Containing Compound (1-2), Compound (2-2), Compound (10-1), and Compound (10-2)

Synthesis was performed as in Synthetic example 5a except that a mixture of methyl benzoate and methyl m-methylbenzoate was used as a starting material in place of methyl m-methylbenzoate. Methyl m-methylbenzoate (21.7 g: 145 mmol), methyl benzoate (19.7 g: 145 mmol), and sodium methoxide (26.1 g: 483 mmol) were added to a solution of 2,4-diamino-6-methylpyrimidine (15 g: 121 mmol) in N-ethylpyrrolidone (105 mL), followed by stirring with heating at 40° C. for 3 hours. The temperature of the reaction system was decreased to room temperature. The reaction solution was poured into a liquid mixture of water (190 mL), concentrated hydrochloric acid (63 mL), and ethyl acetate (40 mL) under ice cooling, and the solid component was collected by filtration. The resulting hydrochloride was added to saturated aqueous sodium bicarbonate solution (120 mL) and ethyl acetate (300 mL), followed by stirring with heating for dissolution. The solution was cooled to room temperature to precipitate the product. The crude product was collected by filtration and was dried at 80° C. under reduced pressure for 8 hours to yield a mixture of compound (1-2), compound (2-2), compound (10-1), and compound (10-2) (product amount: 28 g, yield: 67%, water content: 3.0%).

Synthetic Example 22a-2

Synthesis-2 of Mixture A Containing Compound (1-2), Compound (2-2), Compound (10-1), and Compound (10-2)

The crystals prepared in Synthetic example 22a-1 were dried at 170° C. under reduced pressure for 3 hours to give amorphous mixture A. The water content ratio of the mixture immediately after the drying was less than 0.5%.

Synthetic Example 23a

Synthesis of mixture B containing Compound (1-2), Compound (2-2), Compound (10-1), and Compound (10-2)

A mixture of compound (1-2), compound (2-2), compound (10-1), and compound (10-2) was synthesized as in Synthetic example 1a-1 except that a mixture of methyl benzoate (9.3 g) and methyl m-methylbenzoate (15.2 g) was used as a starting material in place of methyl benzoate (23 g) in Synthetic example 1a-1. The content of compound (1-2) was decreased, and the content ratio of compound (2-2) was increased, compared to those in Synthetic example 22a-1.

Synthetic Example 24a

Synthesis of Mixture C 2,4-Diamino-6-chloropyrimidine (5.8 g: 40 mmol) and sodium methoxide (22.7 g) were sequentially added to t-butanol (51 mL) and methanol (9 mL) under a nitrogen gas flow, followed by stirring with heating at 80° C. for 0.5 hours. The reaction solution was cooled to 70° C., and methyl benzoate (19.6 g: 96 mol) was dropwise added thereto, followed by stirring with heating at 70° C. for 6 hours. The reaction solution was cooled to 40° C., and 1-methoxy-2-propanol (45 mL) was added thereto. This solution was added to a liquid mixture of water (68 mL) and acetic acid (25.22 g) cooled with ice. Furthermore, water (200 mL) added thereto, followed by stirring under ice cooling for 1 hour to precipitate the product. The precipitated product was collected by filtration and was washed with poured water to yield 8.3 g (yield: 60%) of the product. The product was identified as a mixture of compound (M-5a)/compound (M-6a)/compound (1-9) in a ratio of 1.5/3.5/95 (area ratio of HPLC) by HPLC.

Synthetic Example 25a

Synthesis of Mixture D 2,4-Diamino-6-methylpyrimidine (7.4 g: 60 mmol) and sodium methoxide (11.3 g) were sequentially added to N-ethylpyrrolidone (30 mL) under a nitrogen gas flow. Subsequently, methyl m-methylbenzoate (21.6 g: 144 mol) was dropwise added thereto, followed by stirring with heating at 40° C. for 3 hours. The reaction solution was added to a liquid mixture of ethyl acetate (30 mL), water (75 mL), and hydrochloric acid (17.5 mL) cooled with ice, and water (100 mL) was further added thereto, followed by stirring under ice cooling for 1 hour to precipitate the product. The precipitated product was collected by filtration and was washed with poured ethyl acetate, acetonitrile, and water to yield 15.1 g (yield: 71%) of the product. The product was identified as a mixture of compound (M-3a)/compound (M-4a)/compound (2-2) by HPLC.

Synthetic Example 26a

Synthesis of Compound (9-1)

The compound was synthesized in accordance with the method described in Bioorg. Med. Chem. Lett., vol. 13, p. 217, 2003.

Synthetic Example 27a

Synthesis of Compound (9-2)

The compound was synthesized in accordance with the method described in Bioorg. Med. Chem. Lett., vol. 13, p. 217, 2003.

Synthetic Example 28a

Synthesis of Compound (9-3)

The compound was synthesized in accordance with the method described in Journal of the Chemical Society, p. 41, 1947.

Synthetic Example 29a

Synthesis of Compound (9-4)

The compound was synthesized in accordance with the method described in Tetrahedron, vol. 57, p. 2787, 2001.

Synthetic Example 30a

Synthesis of Compound (9-5)

The compound was synthesized in accordance with the method described in Angewandte Chemie, vol. 111, p. 2170, 1999.

Synthetic Example 31a

Synthesis of Compound (9-13)

The compound was synthesized as in Synthetic example 1a-1 using compound (9-11) (commercial product) as a starting material in place of 2,4-diamino-6-methylpyrimidine in Synthetic example 1a-1.

Synthetic Example 32a

Synthesis of Compound (6-19)

The compound was synthesized as in Synthetic example 1a-1 except that 2,4-diamino-6-methoxypyrimidine and methyl acetate were used as starting materials in place of 2,4-diamino-6-methylpyrimidine and methyl benzoate, respectively, in Synthetic example 1a-1. The solution after the reaction was poured into an aqueous acetic acid solution, followed by adjusting the solution to pH 6. The precipitated solid was collected by filtration and was washed with poured MeOH/H$_2$O to yield compound (6-19).

The NMR spectrum of produced compound (6-19) is as follows. The NMR spectrum of produced compound (1-9) is as follows.

$^1$H-NMR (solvent: d6-DMSO, standard: tetramethylsilane) δ (ppm) 2.11 (3H, s) 2.26 (3H, s) 3.88 (3H, s) 7.10 (1H, s) 10.11 (1H, br) 10.50 (1H, br)

The water content ratios of the synthesized compounds were measured by a Karl-Fischer method.

Compound (1-2): water content ratio 3.8%
Compound (1-8): water content ratio 5.4%
Compound (1-9) (Synthetic example 3a-1): water content ratio 2.8%
Compound (1-9) (Synthetic example 3a-2): water content ratio 7.1%
Compound (1-9) (Synthetic example 3a-3): water content ratio 7.5%
Compound (1-9) (Synthetic example 3a-4): water content ratio <0.5%
Compound (2-1): water content ratio 5.5%
Compound (2-2): water content ratio 3.4%
Compound (2-4): water content ratio 1.3%
Compound (2-8): water content ratio 1.8%
Compound (2-9): water content ratio 3.2%
Compound (5-1): water content ratio 3.1%
Compound (5-2): water content ratio 0.8%
Compound (5-7): water content ratio 9.1%
Compound (5-8): water content ratio 3.1%
Compound (6-13): water content ratio 1.2%
Compound (6-15): water content ratio 2.7%
Compound (6-16): water content ratio 2.8%
Compound (6-19): water content ratio 0.7%
Compound (7-2): water content ratio 3.1%
Compound (8-2): water content ratio 1.0%
Compound (8-5): water content ratio 2.6%
Compound (8-6): water content ratio 3.1%

Example 2a-1

Production of Cellulose Acylate Film

Preparation of Cellulose Acylate Solution for Film Formation

The exemplary compounds shown in the table below were mixed with cellulose acylate resins having degrees of acetyl substitution in proportions based on 100 parts by mass of the cellulose acylate resins shown in the table, and the compounds were each dissolved in a solvent composed of 396 parts by mass of methylene chloride and 59 parts by mass of methanol to prepare a cellulose acylate (specifically, cellulose acetate) solution.

(Casting)

The cellulose acylate solutions prepared above were each casted with a glass plate casting machine, followed by drying with hot air having a charge air temperature of 70° C. for 6 minutes. The films were peeled off from the glass plates, were fixed to frames, and were dried with hot air having a charge air temperature of 100° C. for 10 minutes and then with hot air having a charge air temperature of 140° C. for 20 minutes to produce cellulose acylate films each having a thickness of 65 μm.

Subsequently, the resulting films were each stretched in cross-direction by an stretched ratio of 30% under conditions of a temperature of 200° C. and a drawing rate of 30%/min to produce cellulose acylate films each having a thickness of 50 μm.

An additive-free film was produced as a comparative example film. Separately, a comparative example film containing an additive of comparative compound 1 having a structure shown below was produced.

[Chem. 157]

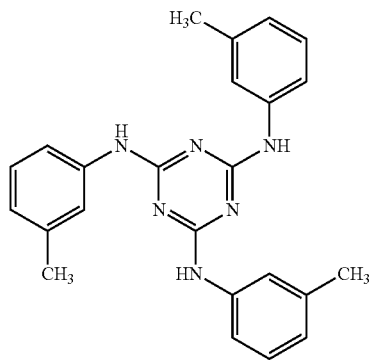

Comparative compound 1

(Evaluation of Optical Characteristics)

The prepared films of examples and comparative examples were each humidified at a relative humidity of 60% at 25° C. for 24 hours. Retardations at a wavelength of 590 nm were measured from the direction perpendicular to the film surface and the directions tilted from the film plane normal by 10° in the range from +50° to −50° using a slow axis as the rotation axis at a relative humidity of 60% at 25° C. with an automatic birefringence meter (KOBRA-21ADH: manufactured by Oji Scientific Instruments Co., Ltd.), and the in-plane retardation value (Re) and the thickness retardation value (Rth) were calculated.

The results are shown in the table below.

In order to evaluate the changes in the retardation value depending on humidity, the humidity dependency (ΔRe) of Re and the humidity dependency (ΔRth) of Rth were calculated from the Re and the Rth (Re [25° C., RH10%] and Rth [25° C., RH10%], respectively) determined as in above except that humidification was performed at a relative humidity of 10% at 25° C. for 2 hours and the Re and the Rth (Re [25° C., RH80%] and Rth [25° C., RH80%], respectively) determined as in above except that humidification was performed at a relative humidity of 80% at 25° C. for 12 hours.

The results are shown as ΔRe and ΔRth in the table below.

The humidity dependency was evaluated by the following evaluation criteria.

[Evaluation Criteria of ΔRe]

⊚: ΔRe<10

○: 10≤ΔRe<11

Δ: 11≤ΔRe<16 x: 16≤ΔRe

[Evaluation Criteria of ΔRth]

⊚: ΔRth<18

○: 18≤ΔRth<21

Δ: 21≤ΔRth<25 x: 25≤ΔRth

TABLE 4

| | Additive | | Cellulose acylate resin | Optical characteristics of film | | | | | | |
|---|---|---|---|---|---|---|---|---|---|---|
| Film No. | Compound | Amount [Parts by mass] | Degree of acetyl substitution | Re [nm] | Rth [nm] | Δ Re [nm] | Δ Rth [nm] | Δ Re Evaluation | Δ Rth Evaluation | Remarks |
| 101a | 1-1 | 4 | 2.42 | 65.1 | 160.3 | 6.7 | 13.1 | ⊚ | ⊚ | Example |
| 102a | 1-2 | 4 | 2.42 | 64.3 | 162.8 | 6.5 | 13.4 | ⊚ | ⊚ | Example |
| 103a | 1-3 | 4 | 2.42 | 67.3 | 164.9 | 7.1 | 13.9 | ⊚ | ⊚ | Example |
| 104a | 1-4 | 4 | 2.42 | 66.4 | 159.3 | 7.6 | 14.3 | ⊚ | ⊚ | Example |
| 105a | 1-5 | 4 | 2.42 | 65.9 | 161 | 8.1 | 15.7 | ⊚ | ⊚ | Example |
| 106a | 1-6 | 4 | 2.42 | 64.2 | 163.5 | 8.4 | 16.2 | ⊚ | ⊚ | Example |
| 107a | 1-7 | 4 | 2.42 | 67.1 | 165.3 | 8.9 | 17.5 | ⊚ | ⊚ | Example |
| 108a | 1-8 | 4 | 2.42 | 65.2 | 163.1 | 7.5 | 14.1 | ⊚ | ⊚ | Example |
| 109a | 1-9*1 | 4 | 2.42 | 62.9 | 161.4 | 6.8 | 13.0 | ⊚ | ⊚ | Example |

TABLE 4-continued

| Film No. | Additive Compound | Amount [Parts by mass] | Cellulose acylate resin Degree of acetyl substitution | Re [nm] | Rth [nm] | Δ Re [nm] | Δ Rth [nm] | Δ Re Evaluation | Δ Rth Evaluation | Remarks |
|---|---|---|---|---|---|---|---|---|---|---|
| 110a | 1-10 | 4 | 2.42 | 64.8 | 161.9 | 9.7 | 18.8 | ◎ | ◎ | Example |
| 111a | 1-11 | 4 | 2.42 | 67.3 | 167.2 | 8.2 | 16.2 | ◎ | ◎ | Example |
| 112a | 2-1 | 4 | 2.42 | 66.1 | 159.1 | 6.9 | 13.3 | ◎ | ◎ | Example |
| 113a | 2-2 | 4 | 2.42 | 52.9 | 142.1 | 6.6 | 12.8 | ◎ | ◎ | Example |
| 114a | 2-4 | 4 | 2.42 | 66.0 | 165.8 | 7.6 | 14.7 | ◎ | ◎ | Example |
| 115a | 2-8 | 4 | 2.42 | 71.2 | 186.0 | 9.7 | 19.6 | ◎ | ○ | Example |
| 116a | 2-9 | 4 | 2.42 | 63.9 | 162.7 | 7.2 | 15.9 | ◎ | ◎ | Example |
| 117a | 3-3 | 4 | 2.42 | 67.9 | 169.1 | 8.2 | 16.5 | ◎ | ◎ | Example |
| 118a | 3-8 | 4 | 2.42 | 66.8 | 164.3 | 7.9 | 15.1 | ◎ | ◎ | Example |
| 119a | 4-1 | 4 | 2.42 | 64.2 | 164.5 | 7.4 | 15.8 | ◎ | ◎ | Example |
| 120a | 4-8 | 4 | 2.42 | 65.3 | 166.4 | 7.8 | 16.2 | ◎ | ◎ | Example |
| 121a | 5-1 | 4 | 2.42 | 64.3 | 166.2 | 7.2 | 15.6 | ◎ | ◎ | Example |
| 122a | 5-8 | 4 | 2.42 | 67.2 | 167.1 | 7.8 | 16.3 | ◎ | ◎ | Example |
| 123a | 6-2 | 4 | 2.42 | 68.2 | 166.9 | 8.5 | 16.7 | ◎ | ◎ | Example |
| 124a | 6-4 | 4 | 2.42 | 64.5 | 164.8 | 8.4 | 16.3 | ◎ | ◎ | Example |
| 125a | 6-5 | 4 | 2.42 | 65.9 | 166.2 | 8.1 | 16.0 | ◎ | ◎ | Example |
| 126a | 6-6 | 4 | 2.42 | 62.0 | 162.5 | 10.1 | 19.7 | ○ | ○ | Example |
| 127a | 6-7 | 4 | 2.42 | 68.4 | 165.2 | 10.2 | 19.8 | ○ | ○ | Example |
| 128a | 6-13 | 4 | 2.42 | 73.5 | 167.0 | 10.8 | 20.3 | ○ | ○ | Example |
| 129a | 6-14 | 4 | 2.42 | 66.7 | 164.5 | 10.6 | 21.0 | ○ | Δ | Example |
| 130a | 6-16 | 4 | 2.42 | 64.2 | 160.1 | 7.4 | 15.6 | ◎ | ◎ | Example |
| 131a | 7-1 | 4 | 2.42 | 71.0 | 167.0 | 7.1 | 16.8 | ◎ | ◎ | Example |
| 132a | 7-2 | 4 | 2.42 | 68.8 | 176.7 | 8.6 | 17.7 | ◎ | ◎ | Example |
| 133a | 7-3 | 4 | 2.42 | 69.4 | 170.2 | 8.7 | 18.0 | ◎ | ○ | Example |
| 134a | 7-5 | 4 | 2.42 | 64.5 | 162.5 | 10.5 | 20.3 | ○ | ○ | Example |
| 135a | 7-7 | 4 | 2.42 | 69.1 | 165.7 | 7.4 | 16.5 | ◎ | ◎ | Example |
| 136a | 7-9 | 4 | 2.42 | 72.0 | 168.3 | 8.1 | 17.2 | ◎ | ◎ | Example |
| 137a | 8-1 | 4 | 2.42 | 60.4 | 144.6 | 10.3 | 21.6 | ○ | Δ | Example |
| 138a | 8-2 | 4 | 2.42 | 55.3 | 135.3 | 11.1 | 22.4 | Δ | Δ | Example |
| 139a | 8-3 | 4 | 2.42 | 56.5 | 142.9 | 10.4 | 21.3 | ○ | Δ | Example |
| 140a | 8-4 | 4 | 2.42 | 58.3 | 143.9 | 10.8 | 22.4 | ○ | Δ | Example |

*1: Compound 1-9 produced in Synthetic example 3a-1

TABLE 5

| Film No. | Additive Compound | Amount [Parts by mass] | Cellulose acylate resin Degree of acetyl substitution | Re [nm] | Rth [nm] | Δ Re [nm] | Δ Rth [nm] | Δ Re Evaluation | Δ Rth Evaluation | Remarks |
|---|---|---|---|---|---|---|---|---|---|---|
| 141a | 8-5 | 4 | 2.42 | 54.9 | 137.3 | 10.7 | 22.0 | ○ | Δ | Example |
| 142a | 8-6 | 4 | 2.42 | 59.2 | 132.2 | 11.5 | 22.0 | Δ | Δ | Example |
| 143a | 9-13 | 4 | 2.42 | 58.2 | 134.1 | 10.8 | 21.9 | Δ | Δ | Example |
| 144a | 1-2 / 2-2 | 2 / 2 | 2.42 | 64.4 | 161.1 | 6.8 | 13.3 | ◎ | ◎ | Example |
| 145a | Mixture A | 4 | 2.42 | 64 | 162.2 | 6.7 | 13.3 | ◎ | ◎ | Example |
| 146a | Mixture B | 4 | 2.42 | 63.8 | 161.4 | 6.8 | 13.4 | ◎ | ◎ | Example |
| 147a | Mixture C | 4 | 2.42 | 60.4 | 156.4 | 7.2 | 16.2 | ◎ | ◎ | Example |
| 148a | Mixture D | 4 | 2.42 | 59.2 | 152.6 | 7.3 | 17.1 | ◎ | ◎ | Example |
| 149a | 1-9*1 / 6-16 | 3.5 / 0.5 | 2.42 | 64.1 | 164.2 | 7.0 | 15.7 | ◎ | ◎ | Example |
| 150a | 2-9 / 6-17 | 3.8 / 0.2 | 2.42 | 62.2 | 161.1 | 7.3 | 16.7 | ◎ | ◎ | Example |
| 151a | 1-9*1 / 1-8 | 3.8 / 0.2 | 2.42 | 64.3 | 163.1 | 7.1 | 16.0 | ◎ | ◎ | Example |
| 152a | 1-9*1 | 6 | 2.42 | 67.2 | 166.1 | 4.8 | 12.1 | ◎ | ◎ | Example |
| 153a | 2-9 | 8 | 2.42 | 68.2 | 167.8 | 4.1 | 11.8 | ◎ | ◎ | Example |
| 154a | 2-9 | 12 | 2.42 | 71.0 | 172.3 | 3.6 | 8.8 | ◎ | ◎ | Example |
| 155a | Mixture B | 6 | 2.42 | 68.2 | 169.1 | 4.7 | 12.0 | ◎ | ◎ | Example |
| 156a | — | 0 | 2.42 | 44.7 | 126 | 16.8 | 26.4 | x | x | Comparative example |
| 157a | Comparative compound 1 | 4 | 2.42 | 94.2 | 201.3 | 11.8 | 22.6 | Δ | Δ | Comparative example |

*1: Compound 1-9 produced in Synthetic example 3a-1

The results shown in the tables above demonstrate that all polymer films of examples of the present invention have increased retardation by containing the compounds of Formula (1) and also have reduced humidity dependency of retardation compared to the comparative example film having increased retardation by containing a triazine ring compound.

It is demonstrated that the effect of reducing the humidity dependency of retardation is relatively low in compounds having a substituent at the 5-position of the pyrimidine ring so as to be sterically bulky and have low flatness, such as compounds (8-6) and (9-13).

Example 2a-2

Production of Cellulose Acylate Film

Cellulose acetate films were formed as in Example 2a-1 except that the stretching was performed at 180° C. instead of 200° C., and the optical characteristics were evaluated.

The humidity dependency was evaluated by the following evaluation criteria.

[Evaluation Criteria of ΔRe]
○: ΔRe<10
Δ: 10≤ΔRe<15
x: 15≤ΔRe

[Evaluation Criteria of ΔRth]
○: ΔRth<22
Δ: 22≤ΔRth<26
x: 26≤ΔRth

The exemplary compounds shown in the table below were mixed with cellulose acylate resins having degrees of acetyl substitution in proportions based on 100 parts by mass of the cellulose acylate resins shown in the table, and the compounds were each dissolved in a solvent composed of 396 parts by mass of methylene chloride and 59 parts by mass of methanol to prepare a cellulose acylate (specifically, cellulose acetate) solution.

(Casting)

The cellulose acylate solutions prepared above were each casted with a glass plate casting machine, followed by drying with hot air having a charge air temperature of 70° C. for 6 minutes. The films were peeled off from the glass plates, were fixed to frames, and were dried with hot air having a charge air temperature of 100° C. for 10 minutes and then with hot air having a charge air temperature of 140° C. for 20 minutes to produce cellulose acylate films each having a thickness of 55 μm.

An additive-free film was produced as a comparative example film. Separately, a comparative example film containing an additive of comparative compound 1 was produced.

(Evaluation of Optical Characteristics)

Optical characteristics were evaluated as in Example 2a-1, and the humidity dependency was evaluated by the following evaluation criteria.

TABLE 6

| Film No. | Additive Compound | Amount [Parts by mass] | Cellulose acylate resin Degree of acetyl substitution | Optical characteristics of film Re [nm] | Rth [nm] | Δ Re [nm] | Δ Rth [nm] | Δ Re Evaluation | Δ Rth Evaluation | Remarks |
|---|---|---|---|---|---|---|---|---|---|---|
| 201a | 1-1 | 2 | 2.86 | 5.2 | 44.3 | 11.2 | 24.1 | Δ | Δ | Example |
| 202a | 1-2 | 4 | 2.86 | 16.0 | 71.0 | 7.9 | 17.2 | ○ | ○ | Example |
| 203a | 2-1 | 4 | 2.86 | 15.3 | 68.1 | 8.1 | 15.4 | ○ | ○ | Example |
| 204a | 2-2 | 4 | 2.86 | 14.8 | 66.9 | 8.3 | 15.7 | ○ | ○ | Example |
| 205a | 2-4 | 4 | 2.86 | 11.0 | 65.2 | 7.9 | 17.1 | ○ | ○ | Example |
| 206a | 3-3 | 4 | 2.86 | 17.9 | 76.1 | 9.2 | 18.4 | ○ | ○ | Example |
| 207a | 3-9 | 4 | 2.86 | 17.5 | 67.9 | 8.9 | 19.0 | ○ | ○ | Example |
| 208a | 4-9 | 4 | 2.86 | 16.4 | 69.3 | 9.1 | 20.5 | ○ | ○ | Example |
| 209a | 5-11 | 4 | 2.86 | 17.6 | 68.4 | 9.2 | 21.1 | ○ | ○ | Example |
| 210a | 6-3 | 4 | 2.86 | 20.2 | 72.5 | 9.8 | 21.4 | ○ | ○ | Example |
| 211a | 7-2 | 4 | 2.86 | 19.4 | 81.8 | 8.6 | 18.2 | ○ | ○ | Example |
| 212a | — | 0 | 2.86 | −10.4 | 13.0 | 12.7 | 27.5 | Δ | x | Comparative example |
| 213a | Comparative compound 1 | 4 | 2.86 | 39.5 | 102.0 | 12.2 | 24.6 | Δ | Δ | Comparative example |

Example 2a-3

Production of Cellulose Acylate Film (Preparation of Cellulose Acylate Solution for Film Formation)

[Evaluation Criteria of ΔRth]
○: ΔRth<15
Δ: 15≤ΔRth<20
x: 20≤ΔRth

TABLE 7

| Film No. | Additive Compound | Amount [Parts by mass] | Cellulose acylate resin Degree of acetyl substitution | Optical characteristics of film Re [nm] | Rth [nm] | Δ Re [nm] | Δ Rth [nm] | Δ Rth Evaluation | Remarks |
|---|---|---|---|---|---|---|---|---|---|
| 301a | 1-9*1 | 6 | 2.86 | 2.4 | 90.3 | 0.7 | 13.1 | ○ | Example |
| 302a | 2-2 | 6 | 2.86 | 1.7 | 83.8 | 0.2 | 12.3 | ○ | Example |

TABLE 7-continued

| Film No. | Additive Compound | Additive Amount [Parts by mass] | Cellulose acylate resin Degree of acetyl substitution | Re [nm] | Rth [nm] | Δ Re [nm] | Δ Rth [nm] | Δ Rth Evaluation | Remarks |
|---|---|---|---|---|---|---|---|---|---|
| 303a | 2-9 | 6 | 2.86 | 1.6 | 89.7 | 0.3 | 13.4 | ○ | Example |
| 304a | 7-2 | 6 | 2.86 | 2.3 | 92.0 | 0.6 | 12.8 | ○ | Example |
| 305a | Mixture A | 6 | 2.86 | 2.4 | 91.1 | 0.5 | 12.7 | ○ | Example |
| 306a | — | 0 | 2.86 | 2.1 | 31.1 | 0.0 | 22.3 | x | Comparative example |
| 307a | Comparative compound 1 | 6 | 2.86 | 3.9 | 137.3 | 0.8 | 15.3 | Δ | Comparative example |

*1: Compound 1-9 produced in Synthetic example 3a-1

Example 2a-4

Production of Cellulose Acylate Film

Cellulose acetate films were produced as in Example 2a-1, and the optical characteristics were evaluated.

TABLE 8

| Film No. | Additive Compound | Additive Amount [Parts by mass] | Cellulose acylate resin Degree of acetyl substitution | Re [nm] | Rth [nm] | Δ Re [nm] | Δ Rth [nm] | Remarks |
|---|---|---|---|---|---|---|---|---|
| 401a | 9-1 | 2 | 2.42 | 47.3 | 136.4 | 11.2 | 23.6 | Example |
| 402a | 9-2 | 2 | 2.42 | 41.1 | 118.6 | 11.5 | 23.8 | Example |
| 403a | 9-3 | 2 | 2.42 | 39.4 | 112.6 | 11.7 | 23.4 | Example |
| 404a | 9-4 | 2 | 2.42 | 31.9 | 115.1 | 10.3 | 21.4 | Example |
| 405a | 9-5 | 2 | 2.42 | 36.1 | 113.8 | 10.4 | 22 | Example |
| 156a | — | 0 | 2.42 | 44.7 | 126 | 16.8 | 26.4 | Comparative example |
| 406a | Comparative compound 1 | 2 | 2.42 | 70.8 | 180.8 | 12 | 26.4 | Comparative example |

The results shown in the tables above demonstrate that all polymer films of examples of the present invention have increased retardation by containing the compounds of Formula (1) and also have reduced humidity dependency of retardation compared to the comparative example film having increased retardation by containing a triazine ring compound.

Example 2a-5

Production of Cellulose Acylate Film

Cellulose acetate films were produced as in Example 2a-1, and the optical characteristics were evaluated.

Films were produced as in Example 2a-1 except that the additive was each mixture E-1 and E-2 composed of exemplary compound (1-2) and a triazine compound shown below at a compositional ratio (mass ratio) of 1:1, and the optical characteristics were measured. The results are shown in the table below together with the results of film 102 of Example 2a-1 and film 156 of a comparative example.

[Chem. 158]

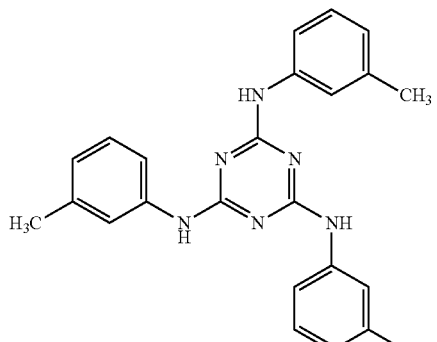

Mixture E-1

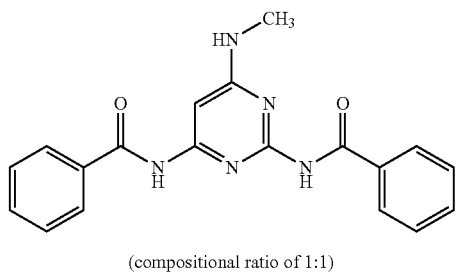

(compositional ratio of 1:1)

Mixture E-2

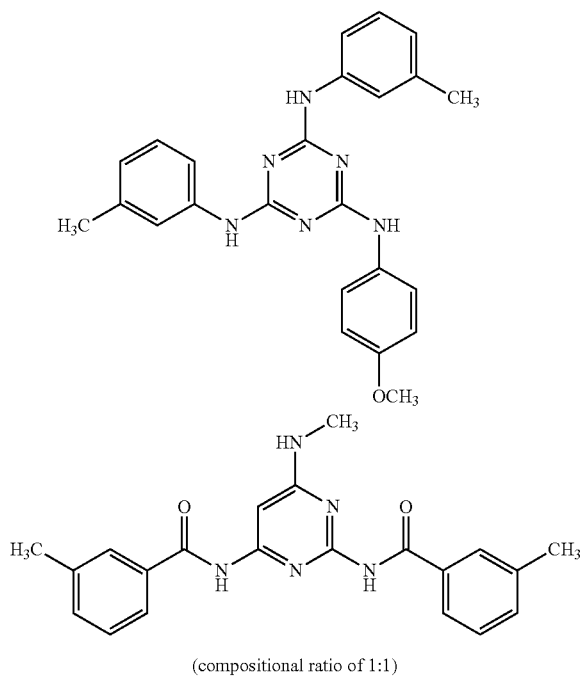

(compositional ratio of 1:1)

TABLE 9

| Film No. | Additive Compound | Amount [Parts by mass] | Cellulose acylate resin Degree of acetyl substitution | Re [nm] | Rth [nm] | Δ Re [nm] | Δ Rth [nm] | Remarks |
|---|---|---|---|---|---|---|---|---|
| 102a | 1-2 | 4 | 2.42 | 64.3 | 162.8 | 6.5 | 13.4 | Example |
| 501a | Mixture E-1 | 4 | 2.42 | 95.3 | 200.9 | 11.6 | 22.6 | Example |
| 502a | Mixture E-2 | 4 | 2.42 | 96.3 | 211.4 | 12.0 | 22.1 | Example |
| 156a | — | 0 | 2.42 | 44.7 | 126.0 | 16.8 | 26.4 | Comparative example |

The results shown in the table demonstrate that the use of a compound (exemplary compound (1-2)) represented by Formula (1) together with a triazine ring compound enhances the effect of increasing the retardation, but reduces the effect of reducing the humidity dependency of retardation. The results demonstrate that the effect of reducing the humidity dependency shown in Examples of the present invention cannot be achieved by a retardation enhancer composed of a molecular complex having a keto-enol tautomeric structure as a constituent element disclosed in Japanese Patent Laid-Open No. 2004-109410 (Patent Literature 1) and a retardation enhancer composed of a disk-shaped compound having a 1,3,5-triazine ring described in Japanese Patent Laid-Open No. 2001-166144 (Patent Literature 2) and Japanese Patent Laid-Open No. 2003-344655 (Patent Literature 3).

Example 3a

Production of Cellulose Acylate Film (Preparation of Cellulose Acylate Solution for Film Formation)

The composition shown below was put in a mixing tank, followed by stirring to dissolve each component to prepare a cellulose acylate solution 301.

TABLE 10

| Composition of cellulose acylate solution 301 | |
|---|---|
| Cellulose acetate having a degree of acetyl substitution of 2.43 and a degree of polymerization of 340: | 100.0 parts by mass |
| Compound (2-2): | 4.0 parts by mass |
| Methylene chloride (first solvent): | 402.0 parts by mass |
| Methanol (second solvent): | 60.0 parts by mass |

(Casting, Stretching)

The cellulose acylate solution 301 was casted with a band casting machine, followed by drying until the remaining solvent content reached 40%. The formed web film was peeled off from the band. When the remaining solvent content reached 20% under conditions of 140° C., the film was stretched in cross-direction by a stretch ratio of 30% with a tenter and was then maintained at 130° C. for 3 minutes. Subsequently, the clips holding the film were removed, and the film was dried at 130° C. for 30 minutes to produce a cellulose acylate film 301. The thickness of the film was 60 μm.

An additive-free film (cellulose acylate film 302) was produced as a comparative example film. Separately, a comparative example film (cellulose acylate film 303) containing an additive of comparative compound 1 was produced.

(Evaluation of Optical Characteristics)

The optical characteristics were evaluated as in Example 2a-1. In the cellulose acylate film 301 containing a compound of the present invention, the humidity dependency of retardation was reduced compared to those of cellulose acylate films 301 and 302.

Example 4a

Production of Cellulose Acylate Film

Cellulose acetate films containing a mixture (R-1), (R-2), and (R-3) as an additive were produced as in Example 2a-1, and the optical characteristics of the films were evaluated.

Cellulose acetate films were produced as in Example 2a-1 except that the degree of substitution of cellulose acylate, the type and amount of additive, the stretching temperature, the stretching ratio, and the thickness of each film were as shown in the following table.

Optical characteristics were evaluated as in Example 1a.

TABLE 11

| Film No. | Additive Mixture | Additive Amount [Parts by mass] | Other additive Compound | Other additive Amount [Parts by mass] | Cellulose acylate resin Degree of acetyl substitution | Cellulose acylate resin Stretching condition | Optical characteristics of film Re [nm] | Optical characteristics of film Rth [nm] | Optical characteristics of film Δ Re [nm] | Optical characteristics of film Δ Rth [nm] |
|---|---|---|---|---|---|---|---|---|---|---|
| 503a (Example) | R-1 | 4 | Polycondensation ester B | 10 | 2.42 | 180° C. 30% | 44 | 109 | 6.5 | 11.8 |
| 504a (Example) | R-3 | 4 | Polycondensation ester B | 10 | 2.42 | 180° C. 30% | 46 | 112 | 6.3 | 11.8 |
| 505a (Example) | R-6 | 4 | Polycondensation ester B | 10 | 2.42 | 180° C. 30% | 46 | 113 | 6.1 | 12 |
| 506a (Example) | R-7 | 4 | Polycondensation ester B | 10 | 2.42 | 180° C. 30% | 48 | 114 | 5.7 | 12 |
| 507a (Example) | R-9 | 4 | Polycondensation ester B | 10 | 2.42 | 180° C. 30% | 47 | 113 | 6 | 12.1 |
| 508a (Example) | — | 0 | Polycondensation ester B | 10 | 2.42 | 180° C. 30% | 35 | 99 | 9.3 | 22.7 |

In the table, polycondensation ester B is a copolymer of adipic acid/ethanediol in a ratio of 50/50.

The films containing mixtures (R-2), (R-4), (R-5), (R-8), (R-10), (R-11), and (R-12) to (R-15) and mixture C were similarly evaluated, and reductions in humidity dependency of retardation were confirmed.

Example 5a

Production of Cellulose Acylate Film

A cellulose acetate film was produced as in Example 2a-1 using the mixture (A) and compound (1-9) as additives.

Cellulose acylate films were produced as in Example 2a-1 except that the degree of substitution of cellulose acylate was 2.42 as a degree of acetyl substitution and the amount of each additive was 4% by mass, though the stretching temperature, the stretching ratio, and the thickness of each film were the same as those in Example 2a-1.

Several films were produced on different days and using mixture A and compound (1-9) different in lots.
(Evaluation of Optical Characteristics)

Optical characteristics were evaluated as in Example 2a-1.

The results shown in the table demonstrate that the optical characteristics of films highly variations when the films are formed using anhydrides of compound (1-9) and mixture A prepared by drying with heating under reduced pressure in Synthetic examples 3-4 and 22-2. This is believed that the compound (1-9) or each compound in the mixture A isolated in the anhydride form absorbs moisture during storage to vary the actual content ratio if an equal amount of anhydride is added for formation of films.

In contrast, the films formed using hydrates prepared in Synthetic examples 3-2 and 22-1 show small variations to indicate excellent stability of quality. This is believed that the water content ratio in crystals prepared in the hydrate form does not vary with the passage of time.

Example 6a

Evaluation in Change of Water Content Ratio

Each compound (0.5 g) shown in the following table was left in a thermostatic and humidifying chamber at 25° C. and 80% RH for 7 days, and then water content ratio was measured by a Karl-Fischer method.

TABLE 12

| Film No. | Additive Species | Additive Synthesis method | Additive Form (Water content ratio) | Sample number | Optical characteristics of film Re [nm] Average | Optical characteristics of film Δ Re [nm] Standard deviation | Optical characteristics of film Rth [nm] Average | Optical characteristics of film Δ Rth [nm] Standard deviation | Variation of optical characteristec |
|---|---|---|---|---|---|---|---|---|---|
| 509a (Example) | Mixture A | Synthetic example 22a-1 | Hydrate (3.0%) | 6 | 68.2 | 1.8 | 174.1 | 3.8 | ○ |
| 510a (Example) | Mixture A | Synthetic example 22a-2 | Amorphous (<0.5%) | 6 | 69.4 | 4.2 | 176.2 | 7.1 | Δ |
| 511a (Example) | Compound 1-9 | Synthetic example 3a-2 | Hydrate (7.1%) | 6 | 65.5 | 1.7 | 171.5 | 4.0 | ○ |
| 512a (Example) | Compound 1-9 | Synthetic example 3a-4 | Amorphous (<0.5%) | 6 | 65.4 | 5.0 | 173.4 | 8.5 | Δ |

"○" means a standard deviation of less than 5%, and "Δ" means a standard deviation of not less than 5%.

TABLE 13

| | Compound | Form | Synthesis method | Initial water content ratio | Water content ratio of at 25° C. and 80% RH for 7 days | Water content ratio of at 25° C. and 10% RH for 7 days |
|---|---|---|---|---|---|---|
| Example | (1-9) | Hydrate | Synthetic example 3a-1 | 2.8 | 2.9 | 2.7 |
| Example | (1-9) | Hydrate | Synthetic example 3a-2 | 7.1 | 7.2 | 7.2 |
| Example | (1-9) | Amorphous | Synthetic example 3a-4 | <0.5 | 6.6 | 1.0 |
| Example | (Mixture A) | Hydrate | Synthetic example 22a-1 | 3.1 | 3.4 | 3.3 |
| Example | (Mixture A) | Amorphous | Synthetic example 22a-2 | <0.5 | 6.5 | 1.3 |
| Example | (2-2) | Hydrate | Synthetic example 5a | 3.4 | 3.4 | 3.2 |
| Example | (2-2) | Amorphous | * | <0.5 | 3.1 | 1.2 |
| Example | (7-2) | Hydrate | Synthetic example 15a | 3.1 | 3.2 | 3.0 |
| Example | (7-2) | Amorphous | * | <0.5 | 2.8 | 0.9 |

* An amorphous compound was prepared as in Synthetic example 3a-4 by drying the compound through heating to the melting point or higher under reduced pressure and then quenching.

The results shown in the table demonstrate that the compound of the present invention in the hydrate form maintains a constant water ratio content regardless of a change in humidity and that the compound in the amorphous form absorbs moisture to vary the water content ratio depending on environmental humidity despite a low initial water content ratio of the amorphous form.

Example 7a

Evaluation of Solution Stability

Each compound (1 part by mass) shown in the following table was dissolved in methylene chloride (87 parts by mass) and methanol (13 parts by mass). The solution was left to stand in a pressure resistant vessel at 80° C. for 66 hours, and then the residual ratio of the compound was quantitatively measured by liquid chromatography. The results are shown in the following table.

TABLE 14

| | Compound | Residual ratio (%) |
|---|---|---|
| Example | (1-1) | >95 |
| Example | (1-2) | >95 |
| Example | (1-4) | >95 |
| Example | (1-9) | >95 |
| Example | (2-1) | >95 |
| Example | (2-2) | >95 |
| Example | (2-4) | >95 |
| Example | (2-9) | >95 |
| Comparative example | (A-1) | 58 |
| Comparative example | (A-2) | 54 |

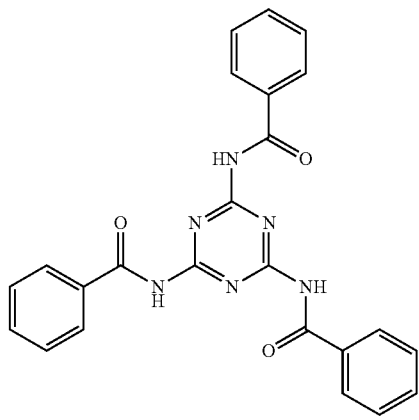 [SMILES: O=C(Nc1nc(NC(=O)c2ccccc2)nc(NC(=O)c2ccccc2)n1)c1ccccc1]

Comparative compound A-1: The compound was synthesized in accordance with the method described in Gazzetta Chimica Italiana (1935), 65, 566-88.

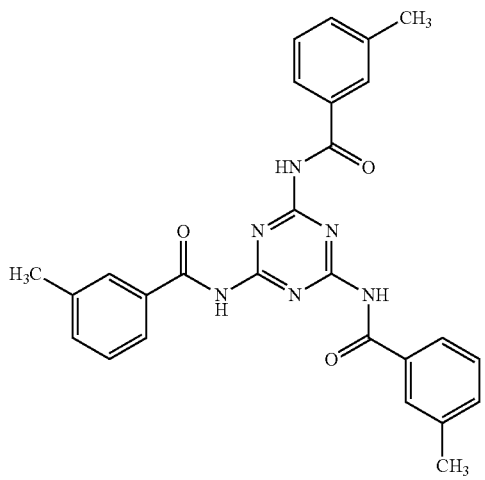 [SMILES: Cc1cccc(C(=O)Nc2nc(NC(=O)c3cccc(C)c3)nc(NC(=O)c3cccc(C)c3)n2)c1]

Comparative compound A-2: The compound is described in Japanese Patent Laid-Open No. 2007-138119 and was synthesized in accordance with the method described in Gazzetta Chimica Italiana (1935), 65, 566-88.

The results shown in the table demonstrate that the compound group A of the present invention shows high solution stability.

Example 1b

Synthetic Example of Compound in Compound Group B Represented by Formula (I)

Synthetic Example 1b

Synthesis of Compound (Ib-3)

Methyl m-methylbenzoate (10.7 g: 71 mmol) and sodium methoxide (7.7 g: 143 mmol) were added to a solution of 2,4-diaminopyrimidine (10 g: 71 mmol) in N-ethylpyrrolidone (70 mL), followed by stirring with heating at 40° C. for 1 hour. The temperature of the reaction system was decreased to room temperature. The reaction solution was poured in a diluted hydrochloric acid for neutralization, followed by extraction with ethyl acetate. The resulting organic layer was washed with saturated brine and was dried over anhydrous sodium sulfate. The desiccant was removed, and the solvent was distilled off. The crude product was purified by silica gel column chromatography (eluent: ethyl acetate) to yield compound (Ib-3). The NMR spectrum of produced compound (Ib-3) is as follows.

$^1$H-NMR (solvent: d6-DMSO, standard: tetramethylsilane) 10.02 (1H, s) 8.00 (1H, d) 7.75-7.68 (2H, m) 7.40-7.33 (2H, m) 6.84 (2H, br) 6.20 (1H, d) 2.35 (3H, s)

Synthetic Example 2b

Synthesis of Compound (Ib-9)

The compound was synthesized as in Synthetic example 1b except that 6-methyl-2,4-diaminopyrimidine and methyl benzoate were used as starting materials in place of 2,4-diaminopyrimidine and methyl m-methylbenzoate, respectively, in Synthetic example 1b. The NMR spectrum of produced compound (Ib-9) is as follows (water content ratio: 2.45%).

$^1$H-NMR (solvent: d6-DMSO, standard: tetramethylsilane) 10.27 (1H, br) 7.97-7.88 (2H, m) 7.60-7.44 (3H, m) 6.70 (2H, br) 6.07 (1H, s) 2.18 (3H, s)

Synthetic Example 3b

Synthesis of Compound (Ib-11)

The compound was synthesized as in Synthetic example 1b except that 6-methyl-2,4-diaminopyrimidine was used as a starting material in place of 2,4-diaminopyrimidine in Synthetic example 1b. The NMR spectrum of produced compound (Ib-11) is as follows (water content ratio: 2.8%).

$^1$H-NMR (solvent: CDCl$_3$, standard: tetramethylsilane) 7.90 (1H, s) 7.75-7.64 (2H, m) 7.34-7.27 (2H, m) 6.07 (1H, s) 5.80 (2H, br) 2.37 (3H, s) 2.21 (3H, s)

Synthetic Example 4b

Synthesis of Compound (Ib-25)

The compound was synthesized as in Synthetic example 1b except that 6-methoxy-2,4-diaminopyrimidine and methyl benzoate were used as starting materials in place of 2,4-diaminopyrimidine and methyl m-methylbenzoate in Synthetic example 1b. The NMR spectrum of produced compound (Ib-25) is as follows (water content ratio: 0.8%).

$^1$H-NMR (solvent: d6-DMSO, standard: tetramethylsilane) 10.29 (1H, s) 7.91-7.86 (2H, m) 7.60-7.25 (3H, m) 6.60 (2H, br) 5.51 (1H, s) 3.73 (3H, s)

Synthetic Example 5b

Synthesis of Compound (Ib-78)

Compound (Ib-78) was synthesized as in Synthetic example 1b. The NMR spectrum of produced compound (Ib-78) is as follows.

$^1$H-NMR (solvent: dimethyl sulfoxide, standard: tetramethylsilane) 10.39 (1H, s) 8.18 (1H, d) 7.83-7.75 (2H, m) 7.42-7.35 (3H, m) 6.39 (2H, br) 2.38 (3H, s)

Synthetic Example 6b

Synthesis of Compound (Ib-84)

Compound (Ib-84) was synthesized as in Synthetic example 2b. The NMR spectrum of produced compound (Ib-84) is as follows (water content ratio: 0.3%).

$^1$H-NMR (solvent: d6-DMSO, standard: tetramethylsilane) 10.46 (1H, s) 7.98 (2H, d) 7.64-7.48 (3H, m) 7.30 (1H, s) 6.29 (2H, br) 2.25 (3H, s)

Synthetic Example 7b

Synthesis of Compound (Ib-86)

Compound (Ib-86) was synthesized as in Synthetic example 3b. The NMR spectrum of produced compound (Ib-86) is as follows (water content ratio: 0.3%).

$^1$H-NMR (solvent: CDCl$_3$, standard: tetramethylsilane) 8.29 (1H, br) 7.70-7.63 (2H, M) 7.58 (1H, S) 7.40-7.35 (2H, M) 4.93 (2H, BR) 2.43 (3H, S) 2.39 (3H, S)

Synthetic Example 8b

Synthesis of Compound (Ib-100)

Compound (Ib-100) was synthesized as in Synthetic example 4b. The NMR spectrum of produced compound (Ib-100) is as follows (water content ratio: 2.0%).

$^1$H-NMR (solvent: d6-DMSO, standard: tetramethylsilane) 10.42 (1H, s) 7.96 (2H, d) 7.65-7.45 (3H, m) 6.85 (1H, s) 6.40 (2H, br) 3.82 (3H, s)

Synthetic Example 9b

Synthesis of Compound (Ib-159)

The compound was synthesized as in Synthetic example 4b except that 6-chloro-2,4-diaminopyrimidine was used as a starting material in place of 6-methoxy-2,4-diaminopyrimidine in Synthetic example 4b. The NMR spectrum of produced compound (Ib-159) is as follows.

$^1$H-NMR (solvent: d6-DMSO, standard: tetramethylsilane) 10.60 (1H, s) 7.92 (2H, d) 7.60-7.45 (3H, m) 7.20 (2H, br) 6.21 (1H, s)

Synthetic Example 10b

Synthesis of Compound (Ib-161)

The compound was synthesized as in Synthetic example 4b except that 6-chloro-2,4-diaminopyrimidine was used as a starting material in place of 6-methoxy-2,4-diaminopyrimidine in Synthetic example 4b. The NMR spectrum of produced compound (Ib-161) is as follows.

$^1$H-NMR (solvent: d6-DMSO, standard: tetramethylsilane) 10.88 (1H, s) 7.96 (2H, d) 7.63-7.48 (3H, m) 7.42 (1H, s) 6.90 (2H, br)

Synthetic Example 11b

Synthesis of Compound (IIb-6)

Compound (IIb-6) was synthesized by reference to the description in Organic and Biomolecular Chemistry, 2007, Vol. 5, No. 10, 1577-1585.

Synthetic Example 12b

Synthesis of Compound (IIb-9)

Compound (IIb-9) was synthesized by reference to the description in Yakugaku Zasshi, 1951, Vol. 71, 315-317.

Synthetic Example 13b

Synthesis of Compound (IIb-14)

Compound (IIb-14) was synthesized by reference to the description in Merck and Co., Inc., U.S. Pat. No. 4,144,338 A1, 1979.

Synthetic Example 14b

Synthesis of Compound (IIb-16)

Compound (IIb-16) was synthesized by reference to the description in Journal of the American Chemical Society, 1947, Vol. 69, 1147-1148.

Synthetic Example 15b

Synthesis of Compound (IIIb-1)

Compound (IIIb-1) was synthesized by reference to the description in Bioorganic and Medicinal Chemistry, 1998, Vol. 9, No. 6, 643-660.

Synthetic Example 16b

Synthesis of Compound (IIIb-6)

Compound (IIIb-6) was synthesized as in synthesis of compound (Ib-3) from diaminopyrimidine synthesized by reference to the description in Chemical & Pharmaceutical Bulletin, 1981, Vol. 29, No. 4, 948-954.

Synthetic Example 17b

Synthesis of Mixture b-A 2,4-Diamino-6-chloropyrimidine (5.8 g: 40 mmol) and sodium methoxide (22.7 g) were sequentially added to t-butanol (51 mL) and methanol (9 mL) under a nitrogen gas flow, followed by stirring with heating at 80° C. for 0.5 hours. The reaction solution was cooled to 70° C., and methyl benzoate (19.6 g: 96 mol) was dropwise added thereto, followed by stirring with heating at 70° C. for 6 hours. The reaction solution was cooled to 40° C., and 1-methoxy-2-propanol (45 mL) was added thereto. The solution was added to a liquid mixture of water (68 mL) and acetic acid (25.22 g) cooled with ice. Furthermore, water (200 mL) was added thereto, followed by stirring under ice cooling for 1 hour to precipitate the product. The precipitated product was collected by filtration and was washed with poured water to yield 8.3 g (yield: 60%) of the product. The product was identified as a mixture of compound (Ib-25)/compound (Ib-100)/reference compound (3) described below in a ratio of 6.5/5.5/88 by HPLC.

Example 1b

Preparation of Cellulose Acylate Solution for Film Formation (Preparation of Cellulose Acylate Solution for Film Formation)

The exemplary compounds shown in the table below were mixed with cellulose acylate resins having degrees of substitution with acetyl groups in proportions based on 100 parts by mass of the cellulose acylate resins shown in the table, and the compounds were each dissolved in a solvent composed of 396 parts by mass of methylene chloride and 59 parts by mass of methanol to prepare a cellulose acylate (specifically, cellulose acetate) solution.

(Casting)

The cellulose acylate solutions prepared above were each casted with a glass plate casting machine, followed by drying with hot air having a charge air temperature of 70° C. for 6 minutes. The films were peeled off from the glass plates, were fixed to frames, and were dried with hot air having a charge air temperature of 100° C. for 10 minutes and then with hot air having a charge air temperature of 140° C. for 20 minutes to produce cellulose acylate films each having a thickness of 65 μm.

Subsequently, the resulting films were each stretched in cross-direction by a stretch ratio of 30% under conditions of a temperature of 200° C. and a drawing rate of 30%/min to produce cellulose acylate films each having a thickness of 50 μm.

An additive-free film was produced as a comparative example film. Separately, a comparative example film containing an additive of comparative compound 1 having a structure shown below was produced.

[Chem. 161]

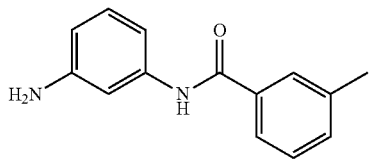

Comparative compound 1b

Films containing any one of exemplary compounds shown in the table below and any one of reference compounds 1 to 3 having structures shown below as additives were produced. The reference compounds can be represented by Formulae (6) and (7).

[Chem. 162]

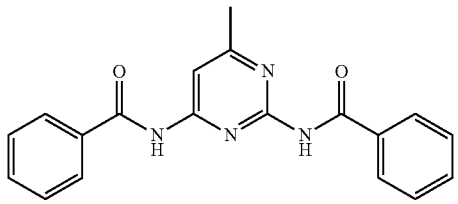

Reference compound 1

(compound example 1-2 in the compound group A)

[Chem. 163]

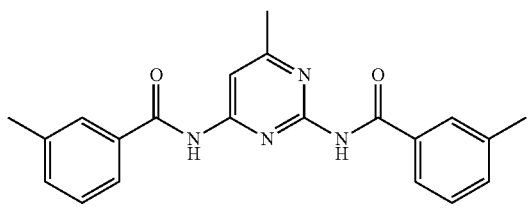

Reference compound 2

(compound example 2-2 in the compound group A)

[Chem. 164]

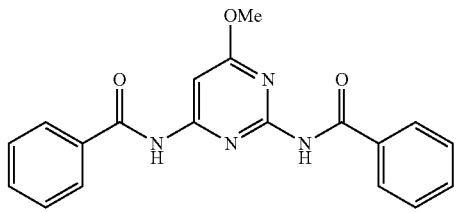

Reference compound 3

(compound example 1-9 in the compound group A)

(Evaluation of Optical Characteristics)

The prepared sample films were each humidified at a relative humidity of 60% at 25° C. for 24 hours. Retardation at a wavelength of 590 nm were measured from the direction perpendicular to the film surface and the directions tilted from the film plane normal by 10° in the range from +50° to −50° using a slow axis as the rotation axis at a relative humidity of 60% at 25° C. with an automatic birefringence meter (KOBRA-21ADH: manufactured by Oji Scientific Instruments Co., Ltd.), and the in-plane retardation value (Re) and the thickness retardation value (Rth) were calculated.

The results are shown in the table below.

In order to evaluate the changes in the retardation value depending on humidity, the humidity dependency (ΔRe) of Re and the humidity dependency (ΔRth) of Rth were calculated from the Re and the Rth (Re [25° C., RH10%] and Rth [25° C., RH10%], respectively) determined as in above except that humidification was performed at a relative humidity of 10% at 25° C. for 2 hours and the Re and the Rth (Re [25° C., RH80%] and Rth [25° C., RH80%], respectively) determined as in above except that humidification was performed at a relative humidity of 80% at 25° C. for 12 hours.

The results are shown as ΔRe and ΔRth in the tables below.

TABLE 15

| Film No. (Example/ Comparative example) | Additive | | Cellulose acylate resin | Optical characteristics of film | | | |
|---|---|---|---|---|---|---|---|
| | Compound | Amount [Parts by mass] | Degree of acetyl substitution | Re [nm] | Rth [nm] | Δ Re [nm] | Δ Rth [nm] |
| 101b (Example) | (Ib-1) | 4 | 2.42 | 55.3 | 135.3 | 9.2 | 17.9 |
| 102b (Example) | (Ib-76) | 4 | 2.42 | 54.1 | 129.8 | 9.2 | 17.6 |
| 103b (Example) | (Ib-9) | 4 | 2.42 | 53.2 | 130.8 | 9.3 | 18.1 |
| 104b (Example) | (Ib-84) | 4 | 2.42 | 49 | 131.2 | 9.3 | 18.3 |
| 105b (Example) | (Ib-11) | 4 | 2.42 | 58.2 | 136.5 | 9.4 | 18.5 |
| 106b (Example) | (Ib-86) | 4 | 2.42 | 49.3 | 134.2 | 9.5 | 18.6 |
| 107b (Example) | (Ib-3) | 4 | 2.42 | 51.2 | 132.6 | 9.7 | 19.2 |
| 108b (Example) | (Ib-78) | 4 | 2.42 | 50.8 | 134.5 | 9.7 | 19 |
| 109b (Example) | (Ib-25) | 4 | 2.42 | 53.6 | 132.1 | 9.8 | 19.1 |

TABLE 15-continued

| Film No. (Example/ Comparative example) | Additive Compound | Amount [Parts by mass] | Cellulose acylate resin Degree of acetyl substitution | Optical characteristics of film | | | |
|---|---|---|---|---|---|---|---|
| | | | | Re [nm] | Rth [nm] | Δ Re [nm] | Δ Rth [nm] |
| 110b (Example) | (Ib-100) | 4 | 2.42 | 55.8 | 130.9 | 9.7 | 19 |
| 111b (Example) | (Ib-27) | 4 | 2.42 | 51.9 | 138.4 | 9.6 | 19.2 |
| 112b (Example) | (Ib-102) | 4 | 2.42 | 47.6 | 132.6 | 9.6 | 19.4 |
| 113b (Example) | (Ib-49) | 4 | 2.42 | 55.4 | 128.6 | 9.7 | 19.4 |
| 114b (Example) | (Ib-124) | 4 | 2.42 | 54.2 | 135.5 | 9.7 | 19.5 |
| 115b (Example) | (Ib-36) | 4 | 2.42 | 49.8 | 137.8 | 10.9 | 21.2 |
| 116b (Example) | (Ib-111) | 4 | 2.42 | 52.7 | 134.2 | 10.8 | 21.3 |
| 117b (Example) | (Ib-29) | 4 | 2.42 | 56.3 | 133.9 | 10.9 | 21.3 |
| 118b (Example) | (Ib-104) | 4 | 2.42 | 45.9 | 134.1 | 10.7 | 21.7 |
| 119b (Example) | (Ib-31) | 4 | 2.42 | 56 | 135.9 | 10.7 | 21.6 |
| 120b (Example) | (Ib-106) | 4 | 2.42 | 58.3 | 136.1 | 10.7 | 21.9 |
| 121b (Example) | (Ib-6) | 4 | 2.42 | 57.4 | 135.5 | 11.1 | 21.4 |
| 122b (Example) | (Ib-81) | 4 | 2.42 | 56.5 | 132.9 | 11.2 | 21.5 |
| 123b (Example) | (Ib-75) | 4 | 2.42 | 55.9 | 133.7 | 11.2 | 21.7 |
| 124b (Example) | (Ib-150) | 4 | 2.42 | 54.2 | 134.8 | 11.2 | 21.9 |
| 125b (Example) | (Ib-41) | 4 | 2.42 | 55.1 | 131.5 | 11.4 | 22 |
| 126b (Example) | (Ib-116) | 4 | 2.42 | 54.9 | 130.7 | 11.3 | 22.2 |
| 127b (Example) | (Ib-67) | 4 | 2.42 | 53.2 | 137.2 | 11.5 | 22.3 |
| 128b (Example) | (Ib-142) | 4 | 2.42 | 49.8 | 133.6 | 11.6 | 22.1 |
| 129b (Example) | (Ib-24) | 4 | 2.42 | 48.4 | 134.2 | 11.7 | 22.4 |
| 130b (Example) | (Ib-99) | 4 | 2.42 | 50.6 | 136.4 | 11.8 | 22.5 |
| 131b (Example) | (Ib-151) | 4 | 2.42 | 52.1 | 135.1 | 11.8 | 22.6 |
| 132b (Example) | (Ib-153) | 4 | 2.42 | 54.3 | 137.3 | 11.8 | 22.5 |
| 133b (Example) | (Ib-73) | 4 | 2.42 | 55.7 | 137.6 | 12 | 22.7 |
| 134b (Example) | (Ib-148) | 4 | 2.42 | 54 | 136.5 | 12.2 | 22.7 |
| 135b (Example) | (Ib-74) | 4 | 2.42 | 48.5 | 138.1 | 12.2 | 22.8 |
| 136b (Example) | (Ib-149) | 4 | 2.42 | 49.2 | 137.3 | 12.4 | 23.1 |
| 137b (Example) | (IIIb-6) | 4 | 2.42 | 50.1 | 132.2 | 13.4 | 24 |
| 138b (Example) | (IIb-6) | 4 | 2.42 | 52.6 | 130.8 | 13.4 | 24.3 |
| 139b (Example) | (IIb-14) | 4 | 2.42 | 54.6 | 131.7 | 13.6 | 24.5 |
| 140b (Example) | (IIb-16) | 4 | 2.42 | 56.3 | 130.9 | 13.5 | 24.7 |
| 141b (Example) | (IIb-9) | 4 | 2.42 | 59.6 | 131.3 | 13.6 | 24.5 |
| 142b (Example) | (IIIb-1) | 4 | 2.42 | 51.9 | 129.7 | 13.7 | 24.6 |
| 143b (Example) | (IVb-1) | 4 | 2.42 | 53.6 | 138.5 | 13.8 | 24.8 |
| 144b Comparative example) | — | 0 | 2.42 | 44.7 | 126 | 16.8 | 26.4 |

TABLE 15-continued

| Film No. (Example/ Comparative example) | Additive Compound | Amount [Parts by mass] | Cellulose acylate resin Degree of acetyl substitution | Re [nm] | Rth [nm] | Δ Re [nm] | Δ Rth [nm] |
|---|---|---|---|---|---|---|---|
| 145b (Comparative example) | Comparative compound 1b | 4 | 2.42 | 60.2 | 140.3 | 14.5 | 26.1 |

TABLE 16

| Film No. (Example/ Comparative example) | Additive Compound | Amount [Parts by mass] | Cellulose acylate resin Degree of acetyl substitution | Re [nm] | Rth [nm] | Δ Re [nm] | Δ Rth [nm] |
|---|---|---|---|---|---|---|---|
| 146b (Example) | (Ib-3) | 4 | 2.86 | 7.6 | 22.8 | 9.7 | 20.1 |
| 147b (Example) | (Ib-78) | 4 | 2.86 | 5.1 | 24.7 | 9.8 | 21.3 |
| 148b (Example) | (Ib-9) | 4 | 2.86 | 8.9 | 21 | 9.5 | 20.5 |
| 149b (Example) | (Ib-84) | 4 | 2.86 | 5.7 | 11.8 | 9.4 | 19.9 |
| 150b (Example) | (Ib-11) | 4 | 2.86 | 10.2 | 26.8 | 9.5 | 21.4 |
| 151b (Example) | (Ib-86) | 4 | 2.86 | 7.6 | 27.1 | 9.7 | 22.3 |
| 152b (Example) | (Ib-25) | 4 | 2.86 | 9.7 | 26.1 | 9.8 | 22.7 |
| 153b (Example) | (Ib-100) | 4 | 2.86 | 10.7 | 24.3 | 9.7 | 21.3 |
| 154b (Example) | (Ib-151) | 4 | 2.86 | 7.6 | 28.6 | 11 | 23.5 |
| 155b (Comparative example) | — | 0 | 2.86 | −10.4 | 13 | 12.7 | 27.5 |
| 156b (Comparative example) | Comparative compound 1b | 4 | 2.86 | 10.2 | 25.4 | 12.5 | 26.4 |
| 157b (Example) | (Ib-9) (Ib-84) | 2 2 | 2.42 | 51.4 | 130.9 | 9.3 | 18.2 |
| 158b (Example) | (Ib-9) Reference compound 1 | 2 2 | 2.42 | 56.3 | 145.8 | 8.4 | 15.8 |
| 159b (Example) | (Ib-84) Reference compound 1 | 2 2 | 2.42 | 56.2 | 144.9 | 8.3 | 15.7 |
| 160b (Example) | (Ib-9) (Ib-84) Reference compound 1 | 1.8 1.8 0.4 | 2.42 | 52.3 | 132.1 | 8.8 | 16.5 |
| 161b (Example) | (Ib-9) (Ib-84) Reference compound 1 | 1 1 2 | 2.42 | 56.4 | 145.2 | 8.2 | 15.6 |
| 162b (Example) | (Ib-9) Reference compound 1 | 0.25 3.75 | 2.42 | 65.5 | 158.6 | 6.7 | 13.4 |
| 163b (Example) | (Ib-84) Reference compound 1 | 0.25 3.75 | 2.42 | 65.8 | 160.7 | 6.7 | 13.4 |
| 164b (Example) | (Ib-9) (Ib-84) Reference compound 1 | 0.2 0.2 3.6 | 2.42 | 64.1 | 159.2 | 6.5 | 13.5 |
| 165b (Example) | (Ib-11) (Ib-86) | 2 2 | 2.42 | 54.3 | 135.1 | 9.5 | 18.6 |

TABLE 17

| Film No. (Example/ Comparative example) | Additive Compound | Amount [Parts by mass] | Cellulose acylate resin Degree of acetyl substitution | Re [nm] | Rth [nm] | Δ Re [nm] | Δ Rth [nm] |
|---|---|---|---|---|---|---|---|
| 166b (Example) | (Ib-11) | 2 | 2.42 | 54.1 | 138.4 | 8.6 | 15.7 |
| | Reference compound 2 | 2 | | | | | |
| 167b (Example) | (Ib-86) | 2 | 2.42 | 53.8 | 139.2 | 8.5 | 15.7 |
| | Reference compound 2 | 2 | | | | | |
| 168b (Example) | (Ib-11) | 1.5 | 2.42 | 54.1 | 138.8 | 8.6 | 15.8 |
| | (Ib-86) | 1.5 | | | | | |
| | Reference compound 2 | 1 | | | | | |
| 169b (Example) | (Ib-11) | 1 | 2.42 | 54.7 | 138.7 | 8.5 | 15.6 |
| | (Ib-86) | 1 | | | | | |
| | Reference compound 2 | 2 | | | | | |
| 170b (Example) | (Ib-11) | 0.5 | 2.42 | 51.9 | 156.8 | 6.6 | 12.9 |
| | Reference compound 2 | 3.5 | | | | | |
| 171b (Example) | (Ib-86) | 0.5 | 2.42 | 51.7 | 156.5 | 6.6 | 12.8 |
| | Reference compound 2 | 3.5 | | | | | |
| 172b (Example) | (Ib-11) | 0.2 | 2.42 | 51.4 | 156.5 | 6.6 | 12.8 |
| | (Ib-86) | 0.2 | | | | | |
| | Reference compound 2 | 3.6 | | | | | |
| 173b (Example) | (Ib-25) | 2 | 2.42 | 54.5 | 131.4 | 9.8 | 19.0 |
| | (Ib-100) | 2 | | | | | |
| 174b (Example) | (Ib-25) | 2 | 2.42 | 58.4 | 146.7 | 8.3 | 16.1 |
| | Reference compound 3 | 2 | | | | | |
| 175b (Example) | (Ib-100) | 2 | 2.42 | 58.5 | 146.1 | 8.2 | 16.2 |
| | Reference compound 3 | 2 | | | | | |
| 176b (Example) | (Ib-25) | 1.5 | 2.42 | 58.1 | 146.5 | 8.1 | 16.1 |
| | (Ib-100) | 1.5 | | | | | |
| | Reference compound 3 | 1 | | | | | |
| 177b (Example) | (Ib-25) | 1 | 2.42 | 57.9 | 146.7 | 8.2 | 16.2 |
| | (Ib-100) | 1 | | | | | |
| | Reference compound 3 | 2 | | | | | |
| 178b (Example) | (Ib-25) | 0.2 | 2.42 | 62.8 | 161.8 | 6.8 | 13.1 |
| | Reference compound 3 | 3.8 | | | | | |
| 179b (Example) | (Ib-100) | 0.2 | 2.42 | 62.7 | 162.1 | 6.7 | 13.0 |
| | Reference compound 3 | 3.8 | | | | | |
| 180b (Example) | (Ib-25) | 0.2 | 2.42 | 62.3 | 161.1 | 6.8 | 13.0 |
| | (Ib-100) | 0.2 | | | | | |
| | Reference compound 3 | 3.6 | | | | | |
| 181b (Example) | Mixture b-A | 4 | 2.42 | 63.4 | 163.2 | 6.5 | 12.8 |
| 182b (Reference example) | Reference compound 1 | 4 | 2.42 | 64.3 | 162.8 | 6.5 | 13.4 |
| 183b (Reference example) | Reference compound 2 | 4 | 2.42 | 52.9 | 142.1 | 6.6 | 12.8 |
| 184b (Reference example) | Reference compound 3 | 4 | 2.42 | 62.9 | 161.4 | 6.8 | 13.0 |

The results shown in the tables above demonstrate that all polymer films of examples of the present invention have increased retardation by containing the compounds of Formula (I) and also have reduced humidity dependency of retardation compared to the comparative example film having increased retardation by containing comparative compound 1. It is demonstrated that the effects are synergistically enhanced by adding two or more compounds of Formula (I) to a film or by adding a reference compound represented by Formula (6) or (7) together with a compound of Formula (I) to a film.

Example 2b-1

Preparation of Cellulose Acylate Solution for Film Formation (Preparation of Cellulose Acylate Solution for Film Formation)

The exemplary compounds shown in the table below were mixed with cellulose acylate resins having degrees of acetyl substitution shown in the table based on 100 parts by mass of the cellulose acylate resins, and the compounds were each dissolved in a solvent composed of 396 parts by mass of methylene chloride and 59 parts by mass of methanol to prepare a cellulose acylate (specifically, cellulose acetate) solution.

(Casting)

The cellulose acylate solutions prepared above were each casted with a glass plate casting machine, followed by drying with hot air having a charge air temperature of 70° C. for 6 minutes. The films were peeled off from the glass plates, were fixed to frames, and were dried with hot air having a charge air temperature of 100° C. for 10 minutes and then with hot air having a charge air temperature of 140° C. for 20 minutes to produce cellulose acylate films each having a thickness of 55 μm.

An additive-free film was produced as a comparative example film. Separately, a comparative example film containing an additive of comparative compound 1 was produced.

Optical characteristics were evaluated as in Example 1b except that the change in retardation value depending on humidity was evaluated by humidification at a relative humidity of 30% at 25° C. and at a relative humidity of 80% at 25° C. for 12 hours.

TABLE 18

| Film No. (Example/ Comparative example) | Additive Compound | Amount [Parts by mass] | Cellulose acylate resin Degree of acetyl substitution | Re [nm] | Rth [nm] | Δ Re [nm] | Δ Rth [nm] |
|---|---|---|---|---|---|---|---|
| 185b (Example) | (Ib-100) | 6 | 2.86 | 1.5 | 67.2 | 0.4 | 16.4 |
| 186b (Comparative example) | — | 0 | 2.86 | 0.2 | 33.1 | 0.2 | 20.7 |
| 187b (Comparative example) | Comparative compound 1b | 6 | 2.86 | 1.7 | 65.4 | 0.4 | 18.7 |

The results shown in the tables above demonstrate that all polymer films of examples of the present invention have increased retardation by containing the compounds of Formula (I) and also have reduced humidity dependency of retardation compared to the film containing a comparative compound 1.

Example 2b-2

Preparation of Cellulose Acylate Solution for Film Formation

Cellulose acetate films were produced as in Example 2b-1 except that the degree of substitution of cellulose acylate, the type and amount of additive, the stretching temperature, the stretching ratio, and the thickness of each film were as shown in the following table.

Optical characteristics were evaluated as in Example 1b.

TABLE 19

| Film No. (Example/ Comparative example) | Additive Compound | Amount [Parts by mass] | Other additive Compound | Amount [Parts by mass] | Cellulose acylate resin Degree of acetyl substitution | Degree of propionyl substitution | Stretching condition | Thickness [μm] | Re [nm] | Rth [nm] | Δ Re [nm] | Δ Rth [nm] |
|---|---|---|---|---|---|---|---|---|---|---|---|---|
| 188b (Example) | (Ib-100) | 8 | Poly-condensation ester A | 15 | 2.42 | 0 | 180° C. 35% | 65 | 81 | 224 | 5.4 | 16 |
| 189b (Comparative example) | — | 0 | Poly-condensation ester A | 15 | 2.42 | 0 | 180° C. 35% | 65 | 66 | 168 | 9.9 | 26 |
| 190b (Example) | (Ib-100) | 6 | Saccharose benzoate | 6 | 1.5 | 0.85 | 135° C. 40% | 45 | 50 | 124 | 7.4 | 20 |
| 191b (Comparative example) | — | 0 | Saccharose benzoate | 6 | 1.5 | 0.85 | 135° C. 40% | 45 | 49 | 126 | 11 | 25 |
| 192b (Comparative example) | Comparative compound 1b | 8 | Poly-condensation ester A | 15 | 2.42 | 0 | 180° C. 35% | 65 | 84 | 232 | 9.5 | 26 |

In the table, polycondensation ester A is a copolymer of terephthalic acid/succinic acid/ethanediol/propanediol in a ratio of 55/45/50/50.

Example 3b

Production of Cellulose Acylate Film (Preparation of Cellulose Acylate Solution for Film Formation)

The composition shown below was put in a mixing tank, followed by stirring to dissolve each component to prepare a cellulose acylate solution 401.

TABLE 20

| Composition of cellulose acylate solution 401 | |
|---|---|
| Cellulose acetate having a degree of acetyl substitution of 2.43 and a degree of polymerization of 340: | 100.0 parts by mass |
| Compound (Ib-100): | 4.0 parts by mass |
| Methylene chloride (first solvent): | 402.0 parts by mass |
| Methanol (second solvent): | 60.0 parts by mass |

(Casting, Stretching)

The cellulose acylate solution 401 was casted with a band casting machine, followed by drying until the remaining solvent content reached 40%. The formed web film was peeled off from the band. When the remaining solvent content reached 20% under conditions of 140° C., the film was stretched in cross-direction by an elongation percentage of 30% with a tenter and was then maintained at 130° C. for 3 minutes. Subsequently, the clips holding the film were removed, and the film was dried at 130° C. for 30 minutes to produce a cellulose acylate film 401a. The film thickness was 60 μm.

An additive-free film (cellulose acylate film 402a) was produced as a comparative example film. Separately, a comparative example film (cellulose acylate film 403a) containing an additive of comparative compound 1 was produced.

(Evaluation of Optical Characteristics)

Optical characteristics were evaluated as in Example 1b.

In the cellulose acylate film 401a containing a compound of the present invention, the humidity dependency of retardation was reduced compared to those of cellulose acylate films 402a and 403a.

Example 4b

Evaluation of Solution Stability

Each compound (1 part by mass) shown in the following table was dissolved in methylene chloride (87 parts by mass) and methanol (13 parts by mass). The solution was left to stand in a pressure resistant vessel at 80° C. for 66 hours, and then the compound was quantitatively measured by liquid chromatography to calculate the residual percentage. The results are shown in the table.

TABLE 21

| | Compound | Residual ratio (%) |
|---|---|---|
| Example | (Ib-1) | >95 |
| Example | (Ib-3) | >95 |
| Example | (Ib-9) | >95 |
| Example | (Ib-11) | >95 |

TABLE 21-continued

| | Compound | Residual ratio (%) |
|---|---|---|
| Example | (Ib-25) | >95 |
| Example | (Ib-76) | >95 |
| Example | (Ib-78) | >95 |
| Example | (Ib-84) | >95 |
| Example | (Ib-86) | >95 |
| Example | (Ib-100) | >95 |
| Example | (Ib-151) | >95 |
| Example | (Ib-153) | >95 |
| Comparative example | (A-1) | 58 |
| Comparative example | (A-2) | 54 |

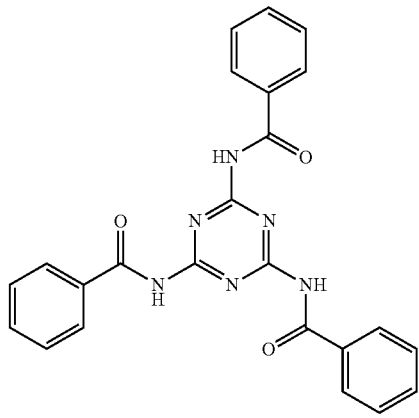 [SMILES: O=C(Nc1nc(NC(=O)c2ccccc2)nc(NC(=O)c2ccccc2)n1)c1ccccc1]

Comparative compound A-1: The compound was synthesized in accordance with the method described in Gazzetta Chimica Italiana (1935), 65, 566-88.

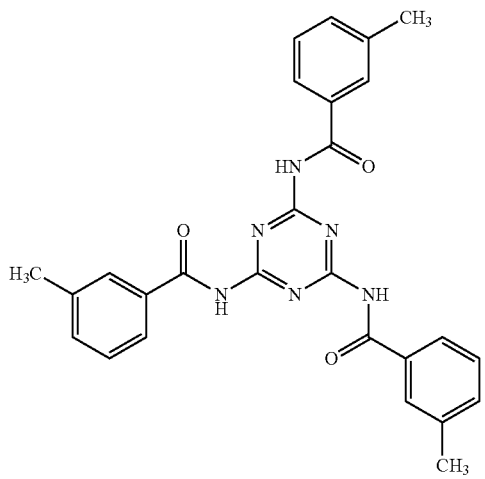 [SMILES: Cc1cccc(C(=O)Nc2nc(NC(=O)c3cccc(C)c3)nc(NC(=O)c3cccc(C)c3)n2)c1]

Comparative compound A-2: The compound is described in Japanese Patent Laid-Open No. 2007-138119 and was synthesized in accordance with the method described in Gazzetta Chimica Italiana (1935), 65, 566-88.

The results shown in the table demonstrate that the compound group B of the present invention shows high solution stability.

161

DESCRIPTION OF SYMBOLS

1 top substrate of liquid crystal cell
3 bottom substrate of liquid crystal cell
5 liquid crystal layer (liquid crystal molecules)
8a, 8b protective film of polarizing plate
9a, 9b absorption axis of protective film of polarizing plate
10a, 10b phase difference film (polymer film of the present invention)
11a, 11b absorption axis of phase difference film (polymer film of the present invention)
P1, P2 polarizing plate
LC liquid crystal cell

What is claimed is:

1. A compound represented by Formula (7-1) or a hydrate of the compound, a solvate of the compound, or a salt of the compound:

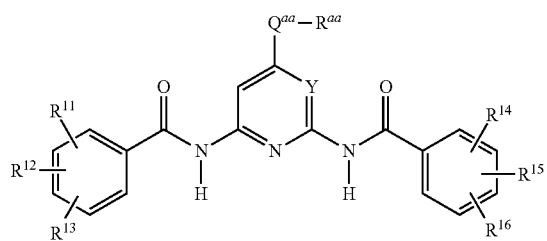

Formula (7-1)

wherein in Formula (7-1), Y represents —N; $Q^{aa}$ represents —O—, —S—, —NH—, or —N(R)—; wherein R is an alkyl group having 1 to 8 carbon atoms; $R^{aa}$ represents a halogen atom or an alkyl group having 1 to 8 carbon atoms, and $R^d$ and $R^{aa}$ are optionally bonded to each other to form a ring structure; and $R^{11}$, $R^{12}$, $R^{13}$, $R^{14}$, $R^{15}$, and $R^{16}$ each independently represent a hydrogen atom, a carbamoyl group, a sulfamoyl group, an alkyl group having 1 to 8 carbon atoms, or an alkoxy group having 1 to 8 carbon atoms.

2. The compound or a hydrate of the compound, a solvate of the compound, or a salt of the compound according to claim 1, the compound being represented by Formula (8), Formula (9), or Formula (10):

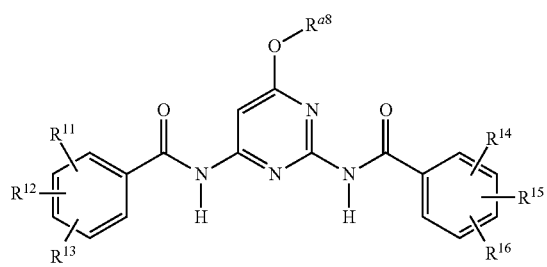

Formula (8)

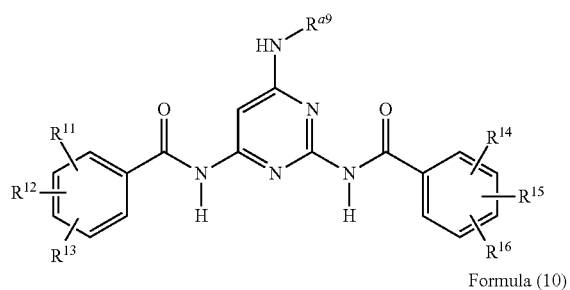

Formula (9)

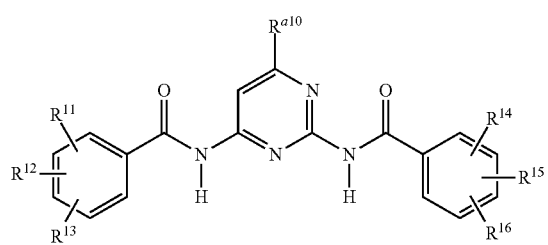

Formula (10)

wherein $R^{11}$, $R^{12}$, $R^{13}$, $R^{14}$, $R^{15}$, and $R^{16}$ each independently represent a hydrogen atom, a halogen atom, a carbamoyl group, a sulfamoyl group, an alkyl group having 1 to 8 carbon atoms, or an alkoxy group having 1 to 8 carbon atoms; and $R^{a8}$, $R^{a9}$, and $R^{a10}$ each independently represent an alkyl group having 1 to 8 carbon atoms.

3. The compound or a hydrate of the compound, a solvate of the compound, or a salt of the compound according to claim 2, $R^{a8}$, $R^{a9}$, and $R^{a10}$ each independently represent an alkyl group having 1 to 4 carbon atoms.

4. A hydrate of the compound or a solvate of the compound according to claim 1.

5. A hydrate of the compound according to claim 1.

6. A method of producing a compound represented by Formula (7-1) or a salt of the compound, a hydrate of the compound, or a solvate of the compound, which comprises
reacting with a compound represented by Formula (7a), a compound represented by a scheme, and represented by Formula (7b):

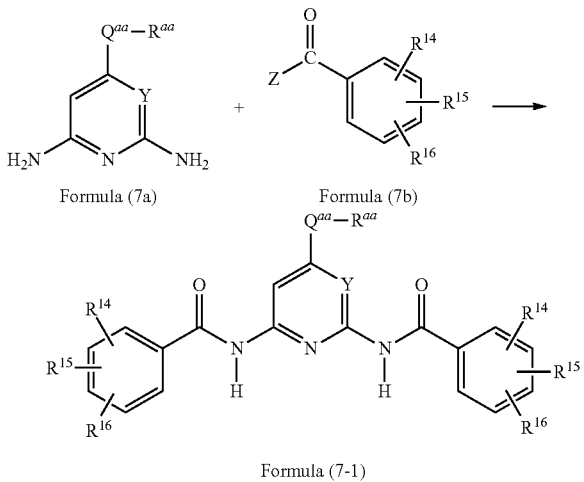

Formula (7a)    Formula (7b)

Formula (7-1)

wherein in Formula (7a) and Formula (7b), $Q^{aa}$ represents —O—, —S—, —NH—, or —N(R)—, wherein R is an alkyl group having 1 to 8 carbon atoms; $R^{aa}$ represents a halogen atom or an alkyl group having 1 to 8 carbon atoms; $R^{14}$, $R^{15}$, and $R^{16}$ each independently represent a hydrogen atom, a carbamoyl group, a sulfamoyl group, an alkyl group having 1 to 8 carbon atoms, or an alkoxy group having 1 to 8 carbon atoms; and Z represents a halogen atom, a hydroxy group, an alkoxy group, aryloxy group, or an acyloxy group.

7. The method according to claim 6, further comprising: crystallizing the compound represented by Formula (7-2) from water or an organic solvent to yield the hydrate of the compound represented by Formula (7-1) or solvate of the compound.

\* \* \* \* \*